(12) United States Patent
Corcoran et al.

(10) Patent No.: US 8,507,208 B2
(45) Date of Patent: Aug. 13, 2013

(54) METHODS AND COMPOSITIONS FOR DETECTION OF BIOLOGICAL MATERIALS USING MICROFLUIDIC DEVICES

(75) Inventors: Robert C. Corcoran, Laramie, WY (US); Debashis Dutta, Laramie, WY (US)

(73) Assignee: University of Wyoming, Laramie, WY (US)

( * ) Notice: Subject to any disclaimer, the term of this patent is extended or adjusted under 35 U.S.C. 154(b) by 3 days.

(21) Appl. No.: 12/842,526

(22) Filed: Jul. 23, 2010

(65) Prior Publication Data

US 2011/0177530 A1 Jul. 21, 2011

Related U.S. Application Data

(60) Provisional application No. 61/228,065, filed on Jul. 23, 2009.

(51) Int. Cl.
*G01N 33/53* (2006.01)
*G01N 33/573* (2006.01)
*G01N 33/561* (2006.01)

(52) U.S. Cl.
USPC ........... 435/7.1; 435/7.72; 435/7.92; 436/516

(58) Field of Classification Search
None
See application file for complete search history.

(56) References Cited

U.S. PATENT DOCUMENTS

| | | | |
|---|---|---|---|
| 6,027,890 A | 2/2000 | Ness et al. | |
| 6,342,347 B1 | 1/2002 | Bauer | |
| 6,444,461 B1 | 9/2002 | Knapp et al. | |
| 6,815,212 B2 | 11/2004 | Ness et al. | |
| 7,312,060 B2 | 12/2007 | Rothschild et al. | |
| 7,749,445 B2 | 7/2010 | Masters | |
| 2003/0094369 A1 | 5/2003 | Tolley et al. | |
| 2003/0153024 A1 | 8/2003 | Sullivan et al. | |
| 2004/0115709 A1 | 6/2004 | Morozov et al. | |
| 2004/0115838 A1 | 6/2004 | Quake et al. | |
| 2004/0202994 A1 | 10/2004 | Timperman | |
| 2005/0000811 A1 | 1/2005 | Luka | |
| 2005/0221385 A1* | 10/2005 | Nikiforov et al. | 435/7.1 |
| 2006/0105449 A1 | 5/2006 | Larmer et al. | |
| 2006/0207877 A1 | 9/2006 | Schmidt et al. | |
| 2006/0219557 A1* | 10/2006 | Nikiforov et al. | 204/451 |
| 2006/0252143 A1 | 11/2006 | Lo | |

(Continued)

FOREIGN PATENT DOCUMENTS

CN 101201350 6/2008
EP 0962464 12/1999

(Continued)

OTHER PUBLICATIONS

Choi et al. An integrated microfluidic biomedical detection system for protein analysis with magnetic bead-based sampling capabilities. Lab Chip, 2002, vol. 2, pp. 27-30.*

(Continued)

*Primary Examiner* — Shafiqul Haq
(74) *Attorney, Agent, or Firm* — Lathrop & Gage LLP

(57) ABSTRACT

Provided herein are microfluidic devices and methods useful for sensitive detection of analytes. The methods and devices described herein are also useful for detecting direct or indirect binding of enzymes or catalysts to a surface, for example a surface having analytes bound thereon. Methods disclosed herein include embodiments utilizing a pre-concentration scheme to improve signal levels of corresponding reporter moieties.

21 Claims, 7 Drawing Sheets

A "Elisa" Region
B microfluidic side channel
C semipermeable membrane
D electrode
E detection device
F waste channel
G electrode
H multipurpose reservoir
J downstream channel (optional)
K auxiliary channel (optional)

(56) References Cited

U.S. PATENT DOCUMENTS

| | | |
|---|---|---|
| 2007/0074972 A1 | 4/2007 | Nassef et al. |
| 2007/0111353 A1 | 5/2007 | McCaskill et al. |
| 2008/0012007 A1 | 1/2008 | Li et al. |
| 2008/0108095 A1 | 5/2008 | Li |
| 2008/0274493 A1 | 11/2008 | Quake et al. |
| 2009/0123336 A1 | 5/2009 | Yang et al. |
| 2009/0242429 A1 | 10/2009 | Sitdikov et al. |
| 2010/0075340 A1 | 3/2010 | Javanmard et al. |

FOREIGN PATENT DOCUMENTS

| | | |
|---|---|---|
| EP | 1199558 | 4/2002 |
| JP | 2004219103 | 8/2004 |
| WO | WO 2008/072153 | 6/2008 |
| WO | WO 2011/011669 | 1/2011 |

OTHER PUBLICATIONS

Albers (Oct. 2003) "Electrical biochip technology—a tool for microarrays and continuous monitoring" *Analytical and Bioanalytical Chemistry* 377(3):521-527.

Bothara et al. (Aug. 2008) "Nanomonitors: electrical immunoassays for protein biomarker profiling" *Nanomedicine* 3(4):423-436.

Cheow et al. (2010) "Increasing the Sensitivity of Enzyme-Linked Immunosorbent Assay Using Multiplexed Electrokinetic Concentrator," *Anal. Chem.* 82(8):3383-3388.

Deshpande (1996) "Enzymes and Signal Amplification Systems," In; *Enzyme Immunoassays: From Concept to Product Development*, Chapman and Hall eds, New York, pp. 155-359.

Dujols et al. (1997) "A Long-Wavelength Fluorescent Chemodosimeter Selective for Cu(II) Ion in Water," *J. Am. Chem. Soc.* 119:7386-7387.

Foote et al (Jan. 1, 2005) "Preconcentration of proteins on microfluidic devices using porous silica membranes" *Analyt. Chem.* 77(1):57-63.

Golnabi et al (2007) "Oxygen sensing based on the oxidation process in resorufin dye" *Sensors and Actuators B* 122:109-117.

He et al. (2009) "Design and testing of a microfluidic biochip for cytokine enzyme-linked immunosorbent assay" *Biomicrofluidics* 3(2):022401.

Herr et al. (Mar. 27 2007) "Microfluidic immunoassays as rapid saliva-based clinical diagnostics" *PNAS* 104(13):5268-5273.

Heyries et al. (Jul. 15, 2008) "Microfluidic biochip for chemiluminescent detection of allergen-specific antibodies" *Biosensors and Bioelectronics* 23(12):1812-1818.

Invitrogen (2006) "Amplex Red Hydrogen Peroxide/Peroxidase Assay Kit Revised: 2006." http://probes.invitrogen.com/media/pis/mp22189.pdf 1-7.

International Search Report and Written Opinion Corresponding to International Patent Application No. PCT/US10/43030 Mailed Nov. 23, 2010.

Khandurina et al (May 1,1999) "Microfabricated porous membrane structure for sample concentration and electrophoretic analysis" *Analyt. Chem.* 71(9):1815-1819.

Kovarik et al ( Feb 1, 2008) "Integrated nanopore/microchannel devices for ac electrokinetic trapping of particles" *Analytical Chemistry* 80(3):657-664.

Kraus et al (2011) "Quantitative measurement of human anti-HCV Core immunoglobulins on an electrical biochip platform" *Biosens. Bioelectron.* 26(5):1895-1901.

Kricka et al. (2005) "The Immunoassay Handbook," *in Chapter 11: Signal Generation and Detection Systems (Excluding Homogeneous Assays)* 192-211.

Lee et al. (May 1, 2008) "Increase of reaction rate and sensitivity of low-abundance enzyme assay using micro/nanofluidic preconcentration chip" *Analyt. Chem.* 80(9):3198-3204.

Liu et al. (2009) "Microchip-based ELISA strategy for the detection of low-level disease biomarker in serum" *Anal. Chim. Acta.* 650(1):77-82.

Myaguchi et al. (2009) "Rapid analysis of methamphetamine in hair by micropulverized extraction and microchip-based competitive ELISA" *Forensic Sci. Int.* 184(1-3):1-5.

Perich et al. (1987) "A New Convenient and Efficient General Procedure for the Conversion of Alcohols into Their Dibenxyl Phosphorotriesters Using N, N-Diethyl Dibenzyl Phosphoboramidite," *Tetrahedron Lett.* 28(1):101-102.

Reichmuth et al. (Aug. 2008) "Rapid microchip-based electrophoretic immunoassays for the detection of swine influenza virus" *Lab on a Chip* 8(8):1319-1324.

Reyes et al. (Jun. 15, 2002) "Micro Total Analysis Systems. 1. Introduction, Theory, and Technology," *Anal. Chem.* 74(12):2623-2636.

Ross et al. (1995) "Use of Bis[2-(trialkyllsiyl)ethyl] $N,N$-Dialkylphosphoramidites for the Syntheses of Phosphate Monoester," *J. Chem. Soc. Perkin Trans. 1* 421-426.

Schroeder et al. (Jul. 1978) "Chemiluminescence Yields and Detection Limits of Some Isoluminol Derivatives in Various Oxidation Systems," Anal. Chem 50(8):1114-1120.

Song et al. (Apr. 1, 2004) "Miniature biochip system for detection of *Escherichia coli* 0157:H7 based on antibody-immobilized capillary reactors and enzyme-linked immunosorbent assay" *Analytica Chimica Acta* 507(1):115-121.

Stratis-Cullum et al (Jul. 2008) "Intensified biochip system using chemiluminescence for the detection of *Bacillus globigii* spores" *Analytical and Bioanalytical Chemistry* 391(5):1655-1660.

Thomas et al. (2004) "Bead based electrochemical immunoassay for bacteriophage MS2" *Anal. Chem.* 76:2700-2707.

Treiber et al. (1997) "Chemical and Biological Oxidation of Thiophene: Preparation and Complete Characterization of Thiophene S-Oxide Dimers and Evidence for ThiopheneS $S$-Oxide as an Intermediate in Thiophene Metabolism in Vivo and in Vitro," *J. Am. Chem. Soc.* 119:1565-1571.

Wang et al. (2010) "Study on the kinetics of homogeneous enzyme reactions in a micro/nanofluidics device" *Lab on a Chip* 10(5):639-646.

Wang et al. (Jul. 15, 2005) "Million-Fold Preconcentration of Proteins and Peptides by Nanofluidic Filter" *Analytical Chemistry* 77(14):4293-4299.

Wang et al. (1997) "Low Temperature Bonding for Microfabrication of Chemical Analysis Devices," *Sens. Actuators B* 45:199-207.

Wu et al. (2009) "High speed nanofluidic protein accumulator" *Lab on a Chip* 9(13):1890-1896.

Yang et al. (2010) "Lab-on-a-chip for carbon nanotubes based immunoassay detection of *Staphylococcal* Enterotoxin B (SEB)" *Lab on a Chip* 10:1011-1017.

Yu et al. (Sep. 2008) "A simple, disposable microfluidic device for rapid protein concentration and purification via direct-printing" *Lab on a Chip* 8(9):1496-1501.

* cited by examiner

| | |
|---|---|
| A "Elisa" Region | F waste channel |
| B microfluidic side channel | G electrode |
| C semipermeable membrane | H multipurpose reservoir |
| D electrode | J downstream channel (optional) |
| E detection device | K auxiliary channel (optional) |

METHODS AND COMPOSITIONS FOR DETECTION OF BIOLOGICAL MATERIALS USING MICROFLUIDIC DEVICES

CROSS REFERENCE TO RELATED APPLICATION

This application claims the benefit of and priority to U.S. provisional application 61/228,065, filed Jul. 23, 2009. This application is hereby incorporated by reference in its entirety to the extent not inconsistent herewith.

BACKGROUND

This invention is in the fields of microfluidics and sensitive detection of analytes. This invention relates to methods and compositions providing rapid, sensitive and specific detection of molecules that are capable of forming strongly associated complexes with a binding molecule-enzyme conjugate.

Although this invention can be applied to both natural and unnatural (man-made and man-designed) products, it is especially useful for the detection of biomolecules. The detection of trace levels of biomolecules is of compelling importance for both scientific research and commercial reasons. The presence and concentration of a biomolecule may give important information with respect to the operation of biochemical pathways. From a practical standpoint, this type of information may have important implications with respect to the detection of certain conditions existing in the body (e.g., changes in hormone levels associated with pregnancy, or with the onset of a variety of metabolic disorders), as well as in the detection of diseases (e.g., by direct detection of a disease agent, or by detection of the presence of the body's response to the presence of a disease agent).

Depending on the particular application, different features may be of greater or lesser importance in a detection method (an assay) for a substance. At a gross level, assays may be divided into those that simply show the presence of a target compound (an analyte), and those that are capable of indicating the concentration of the analyte. Assays of the former type may be sufficient in many cases, one example being that of pregnancy tests: the presence of certain hormones are sufficient to establish that a person is pregnant, and varying concentrations (beyond a certain threshold) will not indicate a state of "more" or "less" pregnant. On the other hand, the ability to accurately quantify the amount of an analyte is critical for many applications in both research and diagnostics. For example, certain hormones (e.g., the thyroid hormones thyroxine and triiodothyronine) are always expected to be present in the human body at some level, but concentrations above or below "standard" levels may indicate some adverse condition (e.g., hypo- or hyperthyroidism). A feature of general desirability in all assays is a high level of sensitivity; the ability to detect a compound (quantitatively or not) at a low concentration. Even when the expected concentration range of a target analyte is much higher than the limit of detection, a more highly sensitive assay will generally be preferred, since it will usually be the case that the reliability of the concentrations determined will be greater than for a less sensitive assay. And, in research studies, a highly sensitive assay may allow data to be obtained over a period of time, making it possible to determine something about the rates of biochemical events.

A feature of assays that is gaining increasing importance as science progresses is the speed of the assay. In a research setting, an assay that is both sensitive and rapidly carried out may make it possible to examine and understand the rates of biochemical processes at a much higher level of detail and understanding. In a clinical setting, assays that are both sensitive and rapid are desirable because they may allow timely diagnosis of rapidly progressing diseases, or make possible so-called "point of care" diagnosis, in which a patient can receive an answer about his/her condition while still at a doctor's office. Of course, other desirable assay features include ease of use and low cost. From a financial standpoint, assays that are capable of determining the presence or concentrations of multiple compounds simultaneously are desirable, since they speed diagnosis for a multitude of potential disease markers.

A wide variety of analytical methods have been developed to meet the needs for the detection of biomolecules. These methods vary in their speed, sensitivity and suitability for use with complex biological samples. In most cases the principle deciding factor in the choice of an assay method is sensitivity. For this reason, two classes of assays have risen to particular prominence in biochemical and clinical applications: methods based on the polymerase chain reaction (PCR), and methods based on enzyme linked immunosorbant assays (ELISA). Both of these methods share a number of common features, the most prominent being that they both involve amplification of a signal by processes that result in an increase in number of detectable species over time. In a PCR assay, a target region of a DNA or RNA molecule is recognized by a complimentary probe molecule, and the sequences are replicated. The resulting copies are then replicated again to give new copies, which are in turn replicated, etc. to give a geometric increase in the number of daughter copies. A variety of strategies have been employed to allow for the specific detection of these daughter copies, but the principle strength of the method lies with the fact that the presence of the original analyte can be inferred (i.e., it is not being directly measured) on the basis of the presence the detectable signal resulting from a given number of amplification (replication) cycles. Although PCR methods appear to be unsurpassed in their sensitivity for the detection of nucleic acid analytes, these methods cannot be applied to non-nucleic acid targets. For the vast array of non-nucleic acid targets, it is the other signal amplification method, ELISA, that is of great use.

A different strategy for signal amplification is used in the ELISA method. There are many variants of this method, but the general theme can be illustrated by what has been termed a "sandwich" ELISA assay. In this variant of the method, an antibody is attached by some means to a surface. When exposed to a sample containing the antigen of the antibody (the analyte), it binds with a high association constant to the surface bound antibody to give the binary complex {surface-antibody}-antigen. After washing away excess sample, the system is exposed to an antibody-enzyme conjugate, wherein the antibody can also bind strongly to the antigen, thereby giving a {surface-antibody}-antibody-{antibody-enzyme} ternary complex. After again washing away unbound materials, the ternary complex is exposed to a solution having a substrate for the enzyme of the antibody-enzyme conjugate. The enzyme and substrate for these processes are chosen so that the substrate is rapidly converted to a detectable reaction product. Since a single enzyme is capable of catalyzing hundreds or thousands of such transformations per minute, signal associated with the presence of the enzyme is amplified accordingly. The amount of signal produced in a unit of time can be used to infer the presence of a certain amount of enzyme, and since (in a perfect world) the amount of enzyme is directly proportional to the amount of analyte/antigen, the amount of analyte can be further inferred. Many variants of this general method exist with respect to the enzyme and corresponding signal producing enzyme catalyzed reactions, as well as in the nature of the complexes formed. However, the methods can be summed up in a general way as involving associating an analyte in some way with a surface, followed by association of an enzyme to this analyte through one or more intervening molecules and/or complexes such that there is an enzyme for each molecule of analyte. Formation of this/these complexes is followed by an enzyme catalyzed reaction that produces some reporter molecule (a detectable ELISA product) that provides a signal that can be detected, with the amount of signal being produced proportional to both the time the reaction is allowed to proceed and the number of enzyme (and, by inference, analyte) molecules present.

The fact that essentially any molecule capable of being bound by one (and preferably in some cases, two) antibody(ies) can be detected with a high degree of sensitivity has led to the development of ELISA methods as the most important class of bioanalytical techniques in both research and clinical settings. Nevertheless, there are problems with the methods—or, at least, areas in which the assay could be dramatically improved to a level that would allow applications of the method that are currently impossible to implement. Two closely related aspects of ELISA methods that, if improved, would greatly increase the attractiveness of the methods, are speed and sensitivity. Because ELISA methods rely on a chemical reaction that produces a detectable product, assay speed and sensitivity are integrally related: if an assay is run for a short time, there will likely be relatively little detectable product that has formed, and as a result the limit of detection (LOD) for that time period will not be low. If one needs greater sensitivity, this can easily be attained by letting the assay run for a longer period of time, thereby providing for greater conversion of the enzyme substrate to detectable product. However, this greater sensitivity will come at the price of a longer assay time. It is not uncommon for ELISA methods to require times ranging from thirty minutes to many hours for the development of sufficient signal for a reliable inference regarding enzyme (and thus, analyte) concentration. This combination of time scale and sensitivity is satisfactory for many applications but not, for example, applications in which the kinetics of moderately rapid biological processes are of interest, or for the rapid sample throughput that would be desirable in point-of-care diagnostic applications. The fact is, it is virtually axiomatic that anything that is capable of increasing the speed or sensitivity of an assay method will be desirable.

The desire to improve the speed and/or sensitivity of ELISA methods has led to a number of innovations in this field. Most improvements of the ELISA method have involved improvements in the signal-to-noise ratio (S/N) in the assay. Improvements in S/N by traditional methods have centered around the construction of new ELISA substrates that will provide reporter products that are more readily detectable by virtue of increased extinction coefficient (for UV-based methods) or fluorescence intensity (for fluorescence based methods). However, the source of sensitivity increase in many of the most dramatically improved versions of ELISA methods lies with a remarkably prosaic source: the decrease, or near elimination of noise (background). In principle, if background noise in an assay could be reduced to nothing, then even a mediocre signal would provide infinite S/N, with an associated infinitely low limit of detection (LOD) for a target analyte. In practice, of course, it is not possible to reduce noise to zero; but it can be brought to very low levels by chemical or instrumental means, or both. Signal enhancement in ELISA by elimination of noise through chemical means can be exemplified by the use of chemiluminescent methods, in which an enzyme substrate is converted to a product that then emits light at a detectable wavelength. Since no other species in the mixture are capable of emitting light (and no incident radiation is applied in the assay) background noise is largely decreased to the point of noise associated with the instrument itself. Signal enhancement in ELISA by elimination of noise through principally instrumental/technological means can be seen in time-resolved fluorescence methods, in which an enzyme substrate is converted to a product that exhibits delayed fluorescence; after an initial burst of radiation, there is a short interval during which no observation takes while most "normal" compounds undergo rapid fluorescent decay. This is followed by an observation period during which only the delayed/long lived fluorescence of the desired reaction product is observed. The absence of even a minor fluorescence background leads to dramatic increases in S/N, and correspondingly large improvements in LOD. Though these methods provide dramatic increases in sensitivity, they do so at a cost. The number of bioluminescent systems that are suitable for generating signal by an enzyme catalyzed reaction are limited and often more costly in terms of synthesis. In many cases, these substrates may have to be stored under special conditions to avoid decomposition. Time-resolved fluorescence requires much more sophisticated instrumentation than that used in simpler methods, leading to analysis systems that are much more costly, and much less portable.

SUMMARY

Provided herein are microfluidic devices and methods useful for sensitive detection of analytes. The methods and devices described herein are also useful for detecting direct or indirect binding of enzymes or catalysts to a surface, for example a surface having analytes bound thereon. Methods disclosed herein include embodiments utilizing a pre-concentration scheme to improve signal levels of corresponding reporter moieties.

In a first aspect, methods are provided for detecting a target analyte. A method of this aspect comprises the steps of: providing a microfluidic device comprising a binding surface in fluid communication with a microfluidic trapping region and at least two electrodes; providing to the binding surface a first solution comprising target analyte molecules, wherein at least a portion of the target analyte molecules selectively bind to the binding surface; providing to the binding surface having bound target analyte molecules a second solution comprising catalyst molecules, wherein at least a portion of the catalyst molecules further binds directly or indirectly to target analyte molecules bound to the binding surface; providing to the binding surface having bound target analyte molecules and catalyst molecules a third solution comprising substrate molecules, wherein at least a portion of the substrate molecules undergo a catalytic chemical reaction with catalyst molecules bound directly or indirectly to target analyte molecules bound to the binding surface, thereby directly or indirectly producing reaction product molecules having an ionic charge different from an ionic charge of the substrate molecules; transporting at least a portion of the reaction product molecules into the microfluidic trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region; and detecting an amount of concentrated reaction product molecules in the microfluidic trapping region, for example at one or more time intervals.

In a specific method of this aspect, the microfluidic device further comprises a semi-permeable membrane positioned in the microfluidic trapping region. An embodiment of this aspect comprises the steps of providing a microfluidic device comprising a binding surface in fluid communication with a microfluidic trapping region and at least two electrodes, wherein the microfluidic trapping region comprises a semi-permeable membrane; providing to the binding surface a first solution comprising target analyte molecules, wherein at least a portion of the target analyte molecules selectively bind to the binding surface; providing to the binding surface having bound target analyte molecules a second solution comprising catalyst molecules, wherein at least a portion of the catalyst molecules further binds directly or indirectly to target analyte molecules bound to the binding surface; providing to the binding surface having bound target analyte molecules and catalyst molecules a third solution comprising substrate molecules, wherein at least a portion of the substrate molecules undergo a catalytic chemical reaction with catalyst molecules bound directly or indirectly to target analyte molecules bound to the binding surface, thereby directly or indirectly producing reaction product molecules having an ionic charge different from an ionic charge of the substrate molecules; transporting at least a portion of the reaction product molecules into the microfluidic trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region in front of, at a surface of and/or within the semi-permeable membrane; and detecting an amount of concentrated reaction product molecules in front of, at the surface of and/or within the semi-permeable membrane.

In certain embodiments, the step of detecting an amount of concentrated reaction product molecules comprises exposing the reaction product molecules to electromagnetic radiation and detecting the scattering, absorption or emission of radiation. Typical techniques for this type of detection include, but are not limited to ultraviolet-visible spectrometry, fluorescence spectrometry, Raman spectrometry (SERS), infrared spectrometry or detection of radioactive decay from radiolabeled materials. In embodiments, the step of detecting an amount of concentrated reaction product molecules comprises exposing the reaction product molecules to a reagent that induces chemiluminescence and detecting emitted electromagnetic radiation. In embodiments, the step of detecting an amount of concentrated reaction product molecules comprises measuring a voltage or current required to change the oxidation state (e.g., oxidize or reduce) of the reaction product molecules. Typical techniques for this type of detection include, but are not limited to amperometry and voltametry. In some embodiments where the amount of concentrated reaction product molecules is detected in front of a semi-permeable membrane, the detection device is optionally positioned at the anticipated signal maximum, such as to observe reaction product molecules positioned from between 0 and 1 mm of the surface of the semi-permeable membrane, for example positioned between 50 µm and 500 µm or between 100 µm and 300 µm of the surface of the semi-permeable membrane.

In specific embodiments, the amount of concentrated reaction product molecules is determined as a function of time or at or after one or more time intervals. In an exemplary embodiment, a method of this aspect further comprises the step of determining an amount of the catalyst molecules bound to the binding surface from the detected amount of the concentrated reaction product molecules after one or more time intervals. Optionally, an embodiment further comprises the step of determining an amount of the target analyte in the first solution from the determined amount of the catalyst molecules bound to the binding surface after one or more time intervals. An exemplary embodiment further comprises the step of measuring the rate at which the reaction product molecules are concentrated in the microfluidic trapping region. Optionally, the concentrating step comprises allowing time to pass, whereby unreacted substrate molecules continue to catalytically react with the catalyst molecules bound directly or indirectly to target analyte molecules bound to the binding surface to directly or indirectly produce reaction product molecules which concentrate in the microfluidic trapping region.

Analyte molecules useful with the methods and devices described herein include antigens, proteins, protein fragments, viruses, virus fragments, bacterium, bacterium fragments, hormones, illicit drugs, pharmaceuticals, lipids and any combination or metabolites of these.

In one specific embodiment, the binding surface comprises a surface bound antibody, the target analyte molecules comprise an antigen for the surface bound antibody and the catalyst molecules comprise an enzyme-antibody conjugate. In embodiments, the binding surface comprises molecules, materials or structures capable of binding with the target analyte molecules. In a specific embodiment the binding surface comprises an enzyme linked immunosorbant assay (ELISA) surface. In exemplary embodiments, the binding surface comprises antigens of antibodies, antibodies, biotin, streptavidin, aptamers, nucleic acids, peptide nucleic acids; conjugates between antigens of antibodies, antibodies, biotin, streptavidin, aptamers, nucleic acids, peptide nucleic acids; or any combination of these. In various embodiments, the catalyst molecules are covalently or non-covalently bound to the target analyte molecules bound to the binding surface. For example, in certain embodiments, the catalyst molecules covalently or non-covalently binds to binding molecules, and the binding molecules covalently or non-covalently bind to the target analyte molecules bound to the binding surface, thereby binding the catalyst molecules covalently or non-covalently to the target analyte molecules bound to the binding surface.

Useful catalyst molecules include enzyme-antibody, enzyme-antigen, enzyme-biotin, enzyme-streptavidin, enzyme-avidin, enzyme-protein, enzyme-nucleic acid, enzyme-protein nucleic acid, enzyme-pharmaceutical, enzyme-hormone, enzyme-illicit drug, enzyme-lipid, or enzyme-metabolite conjugates; or any combination of these. In specific embodiments, the catalyst molecules comprise a catalytically active group and antigens of antibodies, antibodies, biotin, streptavidin, aptamers, nucleic acids, peptide nucleic acids or any combination of these. Specifically useful catalyst molecules include those comprising alkaline phosphatase, acid phosphatase, horseradish peroxidase, beta-galactosidase, glucose oxidase, carboxypeptidase B, porcine liver esterase, rabbit esterase, lipase, butyryl cholinesterase, arginase, a catalyst for a bond cleavage reaction, a catalyst for a bond forming reaction, a catalyst for an oxidation reaction, a catalyst for a reduction reaction or any combination or derivative of these. In specific embodiments, the reaction of the substrate molecules at the catalyst is a bond forming reaction, a bond breaking reaction, an oxidation reaction or a reduction reaction.

Substrate molecules useful with the methods of this aspect include substrate molecules which are directly or indirectly converted into ionic product molecules upon and/or after reaction at the catalyst. For various embodiments, the substrate molecules are non-ionic; for other embodiments, the substrate molecules are ionic. In an exemplary embodiment, the substrate molecules and the reaction product molecules are ions having charges of opposite sign.

In a specific embodiment, a substrate molecule undergoes a bond breaking reaction at a catalyst. In a specific embodiment, a substrate molecule undergoes a bond forming reaction at a catalyst. Specifically useful substrate molecules include, but are not limited to Amplex Red®, o-nitrophenyl galactopyranoside (galactose-ONP), fluroescein phosphate,

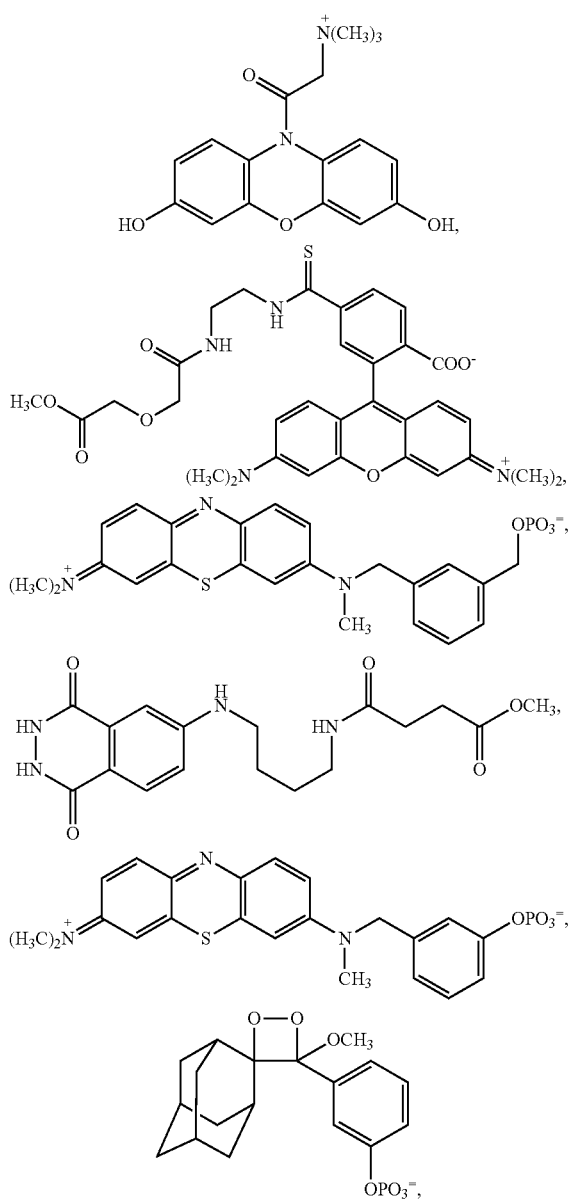

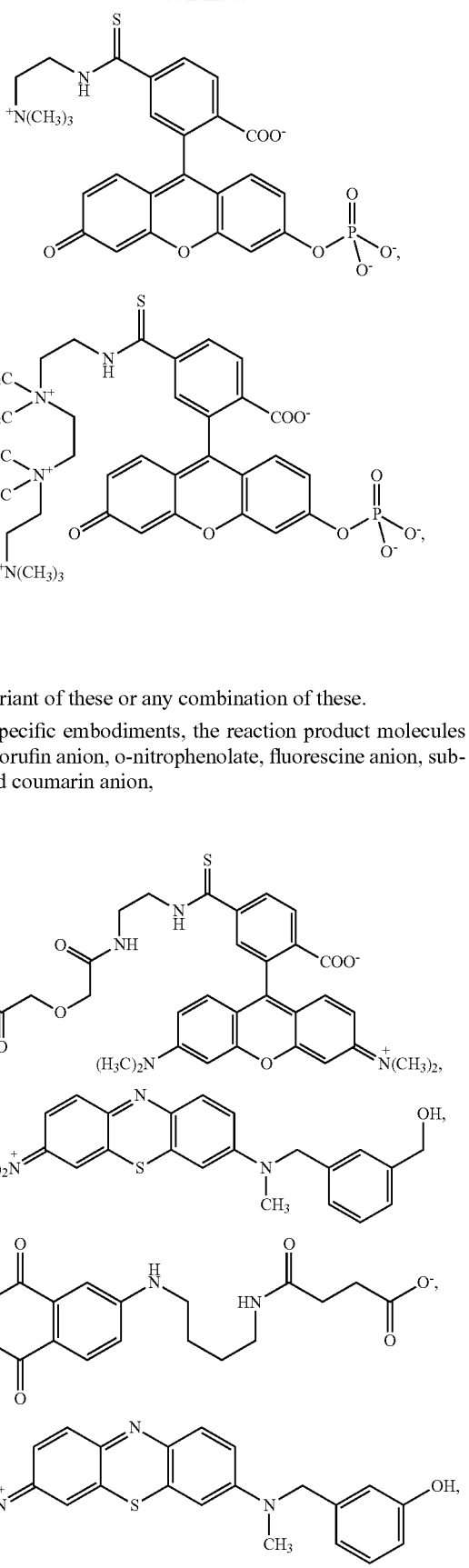

any variant of these or any combination of these.

In specific embodiments, the reaction product molecules are resorufin anion, o-nitrophenolate, fluorescine anion, substituted coumarin anion,

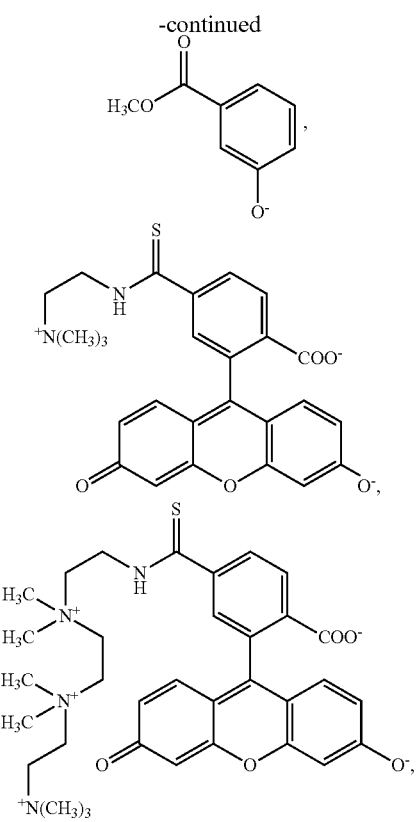

any variant of these or any combination of these. In embodiments, useful reaction product molecules include those which are detectable or include a detectable component, for example by optical detection or electrochemical detection.

In exemplary embodiments, the reaction product molecules comprise a detectable moiety, such as a chromophore or a moiety capable of undergoing a chemiluminescent reaction or a moiety capable of being reversibly oxidized/reduced between two oxidation states or any combination of these. Optionally, the substrate molecules comprise a chromophore and the reaction product molecules comprise the same chromophore or a substantially unaltered variant of the same chromophore. Useful chromophores include, but are not limited to an azo dye, a xanthene dye, an anthraquinone dye, an acridine dye, an oxazine dye, a thiazene dye, a triarylmehtane dye, a diarylmethane dye, a quinoline styryl dye, a phthalocyanine dye, a squarene dye, a polyalkene dye and any combination of these.

In a specific embodiment, the substrate molecules exhibit a first absorption spectrum and the reaction product molecules exhibit a second absorption spectrum at least partially overlapping the first absorption spectrum. In a specific embodiment, the substrate molecules exhibit a first emission spectrum and the reaction product molecules exhibit a second emission spectrum at least partially overlapping the first emission spectrum. In a specific embodiment, the substrate molecules exhibit a first fluorescence spectrum and the reaction product molecules exhibit a second fluorescence spectrum at least partially overlapping the first fluorescence spectrum. Optionally, the first and second absorption spectra are substantially identical; the first and second emission spectra are substantially identical; the first and second fluorescence spectra are substantially identical; or any combination of these.

For certain embodiments, the substrate molecules exhibit a first absorption spectrum and the reaction product molecules exhibit a second absorption spectrum non-overlapping the first absorption spectrum. For certain embodiments, the substrate molecules exhibit a first emission spectrum and the reaction product molecules exhibit a second emission spectrum non-overlapping the first emission spectrum. For certain embodiments, the substrate molecules exhibit a first fluorescence spectrum and the reaction product molecules exhibit a second fluorescence spectrum non-overlapping the first fluorescence spectrum.

In some embodiments, the microfluidic device further comprises a main microfluidic channel and a microfluidic side channel in fluid communication with the main microfluidic channel; optionally, the binding surface is positioned in the main microfluidic channel and the microfluidic trapping region is positioned in the microfluidic side channel. In some embodiments, the microfluidic device further comprises a main microfluidic channel and a microfluidic side channel in fluid communication with the main microfluidic channel, wherein the binding surface is positioned in the main microfluidic channel; optionally, the microfluidic trapping region is positioned in the microfluidic side channel and at least one of the two or more electrodes and the semi-permeable membrane, if present, are positioned in the microfluidic side channel. In certain of these and other embodiments, the microfluidic device further comprises one or more additional microfluidic side channels positioned in fluid communication with the main microfluidic channel. Optionally, a method of this aspect further comprises the step of providing one or more additional solutions to at least one of the one or more additional microfluidic side channels, at least one of the solutions comprising a reagent.

Reagents useful for methods of these aspects include reagents which react with the reaction product molecules to establish an ionic charge of the reaction product molecules or to provide the reaction product molecules with an ionic charge different from that of the substrate molecules. Exemplary reagents include, but are not limited to acids, bases, oxidizing agents and reducing agents. For example, useful reagents include a proton, a carboxylic acid, a phosphoric acid or mono- or di-ester of a phosphoric acid, bisulfate, a sulfonic acid, an ammonium or substituted ammonium, phenol or substituted phenol, hydroxide, a carboxylate anion, phosphate or mono- or di-ester of a phosphate, an amine or substituted amine, a borate or borate ester anionpersulfate, hypochlorite, hydroperoxide and any combination of these.

In certain embodiments, the reaction product molecules undergo a second or subsequent reaction to establish an ionic charge. In general, the reaction product molecules can undergo a second or subsequent reaction covalently bonding the direct reaction product of the catalytic reaction to one or more ionic atoms or molecules to establish the ionic charge of the reaction product molecules which are subsequently detected. Specific examples include protonation or deprotonation reactions.

In embodiments, the step of transporting comprises separating at least a portion of the reaction product molecules from unreacted substrate molecules. Electrical potentials useful with the methods described herein include, but are not limited to DC potentials, such as DC potentials selected over the range of 1 V to 5000 V, for example in the range of 50 V to 2000 V or in the range of 100 V to 1000 V. Optionally, the microfluidic device comprises three or more electrodes positioned in the microfluidic device, for example in fluid and/or electrostatic communication with one another.

A specific method of this aspect comprises the steps of providing a microfluidic device comprising a binding surface in fluid communication with a microfluidic trapping region and at least two electrodes, wherein the microfluidic trapping region includes a semi-permeable membrane; providing to the binding surface a first solution comprising target analyte molecules, wherein at least a portion of the target analyte molecules selectively bind to the binding surface, thereby creating an analyte activated binding surface; providing to the analyte activated binding surface a second solution comprising catalyst molecules, wherein at least a portion of the catalyst molecules further binds directly or indirectly to the analyte activated binding surface, thereby creating a catalytic binding surface; providing to the catalytic binding surface a third solution comprising substrate molecules, the substrate molecules comprising a chromophore, wherein at least a portion of the substrate molecules undergo a catalytic chemical reaction at the catalytic binding surface, thereby producing reaction product molecules, the reaction product molecules comprising the chromophore in the same or a substantially unaltered form as in the substrate molecules and wherein an ionic charge of the reaction product molecules is different from an ionic charge of the substrate molecules; transporting at least a portion of the reaction product molecules into the trapping region by applying an electrical potential between the at least two electrodes, wherein at least one electrode is positioned in the microfluidic trapping region and wherein the electrical potential provides a force attracting the reaction product molecules toward the microfluidic trapping region; concentrating reaction product molecules in the microfluidic trapping region in front of, at a surface of and/or within the semi-permeable membrane; and detecting an amount of concentrated reaction product molecules in front of, at a surface of and/or within the semi-permeable membrane. In a specific embodiment, the step of detecting an amount of concentrated reaction product molecules in front of, at a surface of and/or within the semi-permeable membrane comprises detecting an amount of concentrated reaction product molecules as a function of time or after one or more time intervals.

In another aspect, provided are microfluidic devices for detecting a target analyte. An embodiment of this aspect comprises a main microfluidic channel including a binding surface comprising the target analyte and a catalyst bound directly or indirectly to the target analyte; a solution in the microfluidic device, the solution comprising substrate molecules and ionic reaction product molecules, wherein the ionic reaction product molecules are reaction products of a catalytic bond cleavage reaction or a catalytic bond forming reaction of the substrate molecules at the binding surface or a catalytic reaction in which the substrate is oxidized or a catalytic reaction in which the substrate is reduced; two electrodes in fluid communication with the main microfluidic channel; a microfluidic trapping region in fluid communication with the main microfluidic channel, wherein one of the two electrodes is positioned in the microfluidic trapping region, and wherein a potential is applied between the two electrodes to attract the ionic reaction product molecules into the microfluidic trapping region; and a detector positioned to detect the ionic reaction product molecules positioned in the microfluidic trapping region.

Another embodiment of this aspect comprises a main microfluidic channel including a binding surface region comprising the target analyte and a catalyst bound directly or indirectly to the target analyte; a solution in the microfluidic device, the solution comprising substrate molecules and ionic reaction product molecules, wherein the ionic reaction product molecules are reaction products of a catalytic bond cleavage reaction or a catalytic bond forming reaction of the substrate molecules at the binding surface region or a catalytic reaction in which the substrate is oxidized or a catalytic reaction in which the substrate is reduced; two electrodes in fluid communication with the main microfluidic channel; a microfluidic trapping region in fluid communication with the main microfluidic channel, wherein one of the two electrodes is positioned in the microfluidic trapping region; and a detector positioned to detect the ionic reaction product molecules; characterized in that a first detection sensitivity for the ionic reaction product molecules in the microfluidic trapping region is less than or equal to a second detection sensitivity for the ionic reaction product molecules in the binding surface region when no potential is applied between the two electrodes; and a third detection sensitivity for the ionic reaction product molecules in the microfluidic trapping region is at least twenty times greater than a fourth detection sensitivity for the ionic reaction product molecules in the binding surface region when a potential is applied between the two electrodes to attract the ionic reaction product molecules into the microfluidic trapping region. Optionally, the third detection sensitivity is greater than the fourth detection sensitivity by a factor selected over the range of 20 to 50,000, such as a factor in the range of 100 to 5000.

Devices of this aspect optionally further comprise a semi-permeable membrane positioned in the microfluidic trapping region to impede transport of the ionic reaction product molecules toward the electrode positioned in the microfluidic trapping region. Optionally, more than two electrodes can be utilized. Optionally, the substrate molecules comprise a chromophore and the ionic reaction product molecules comprise the same chromophore. For particular embodiments, the detector detects absorption of light by the ionic reaction product molecules, emission of light from the ionic reaction product molecules or both and/or the detector detects the ionic reaction product molecules in the microfluidic trapping region electrochemically. For certain of the embodiments where the ionic reaction product molecules are detected electrochemically, the electrical potential is an AC potential with a DC bias.

Also provided, in an aspect, are systems for detecting a target analyte. A specific embodiment of this aspect comprises: a microfluidic device comprising: a main microfluidic channel and a plurality of microfluidic side channels positioned in fluid communication with the main microfluidic channel; a binding surface positioned in the main microfluidic channel; a semi-permeable membrane positioned in a first of the plurality of microfluidic side channels, the semi-permeable membrane having a surface oriented toward the main microfluidic channel; a first electrode positioned in the first of the plurality of microfluidic side channels, the first electrode positioned such that the semi-permeable membrane is positioned between the first electrode and the main microfluidic channel; a second electrode positioned in the main microfluidic channel or in a second of the plurality of microfluidic side channels; and a detector positioned to detect ionic molecules comprising a chromophore in front of, at the surface of, or within the semi-permeable membrane. A specific embodiment further comprises a voltage supply in electrical communication with the first and second electrodes, for example providing an electrical potential between the first and second electrodes, such that the ionic molecules comprising the chromophore are attracted toward the first electrode.

In embodiments, systems of this aspect further comprise a solution in the microfluidic device comprising the ionic molecules comprising the chromophore, substrate molecules comprising the chromophore or both. For example, in one embodiment, the ionic molecules comprising the chromophore are reaction products of a reaction of the substrate molecules comprising the chromophore at the binding surface.

For certain of the above described embodiments, the substrate molecules are non-ionic; in other embodiments, the substrate molecules and reaction product molecules are ions having charges of opposite sign. In exemplary embodiments, the semi-permeable membrane impedes the movement of the reaction product molecules toward the at least one electrode positioned in the microfluidic trapping region.

Optionally, for the above embodiments including a semi-permeable membrane, the semi-permeable membrane comprises a silicate; a polymer selected from the group consisting of polyacrylamide, polyester, polyamide, polyacrylate, polysiloxane, polyethylene glycol, polypropylene glycol, polysuccinate, polyglycidyl, polystyryl, polypyridyl and any combination or copolymer of these; or any combination of these. For the above embodiments including a semi-permeable membrane, the semi-permeable membrane is optionally positioned between the binding surface or main microfluidic channel and the electrode in the microfluidic trapping region. For the above embodiments including a semi-permeable membrane positioned in a microfluidic side channel, a surface of the semi-permeable membrane is positioned at a distance from the main microfluidic channel selected over the range of 0 to 1 cm, for example over the range of 10 μm to 2 mm or over the range of 100 μm to 1 mm.

Without wishing to be bound by any particular theory, there can be discussion herein of beliefs or understandings of underlying principles relating to the invention. It is recognized that regardless of the ultimate correctness of any mechanistic explanation or hypothesis, an embodiment of the invention can nonetheless be operative and useful.

DETAILED DESCRIPTION

Figure 1:
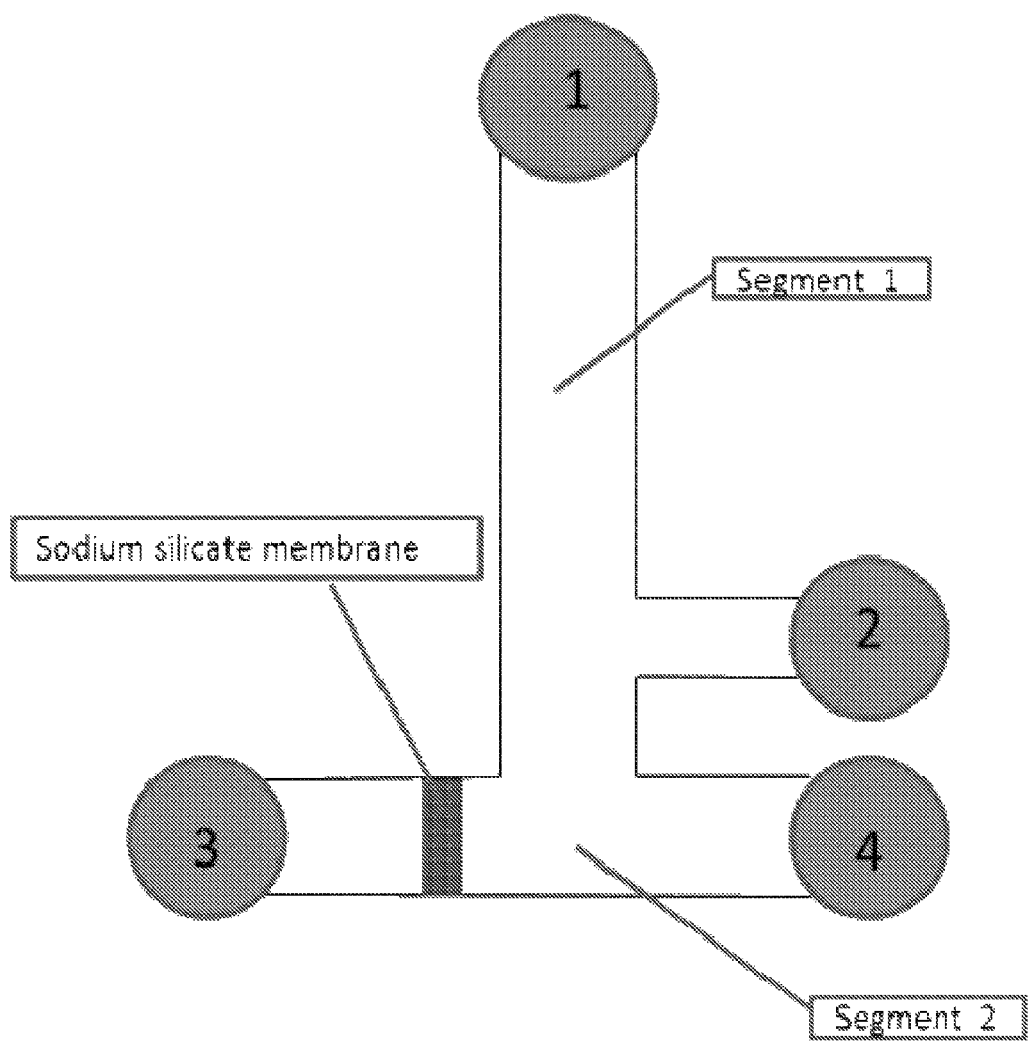
FIG. 1 provides a schematic illustration of an exemplary microfluidic device embodiment.

In general the terms and phrases used herein have their art-recognized meaning, which can be found by reference to standard texts, journal references and contexts known to those skilled in the art. The following definitions are provided to clarify their specific use in the context of the invention.

"Microfluidic device" refers to a system containing liquid constrained in at least one physical dimension generally of the order of nanometers to millimeters. In some embodiments, the liquid is constrained to a lateral dimension selected between 1 nm and 1 cm, such as a narrower lateral dimension (e.g., depth) selected over the range of 1 nm to 5 mm, 100 nm to 100 μm or 500 nm to 50 μm, and a wider lateral dimension (e.g., width) selected over the range of 1 nm to 1 cm, 10 μm to 2 mm or 1 μm to 10 mm. In embodiments, an axial (e.g., flow) direction in a microfluidic device can be long, for example on the order of meters, but will more commonly be 0.1 cm to 10 cm or 1 cm to 5 cm. Microfluidics are distinguished herein from macrofluidics.

"Main microfluidic channel" refers to a specific portion of a microfluidic device. In one embodiment, a main microfluidic channel is generally observed to contain the majority of fluid in a flowing system. In embodiments, a main microfluidic channel has a flow axis with one or more microfluidic side channels each having a flow axis which is non-parallel (e.g., perpendicular) to the flow axis of the main microfluidic channel. "Microfluidic side channel" refers to a specific portion of a microfluidic device. In one embodiment, a microfluidic side channel is generally observed to contain only a small amount of the total flow of fluid in a flowing system. In one embodiment, a microfluidic side channel in a flowing system does not exhibit flow as found in other parts of the corresponding flowing system, but may be characterized as having atoms, molecules or ions which move via diffusion or electrophoresis.

"Microfluidic trapping region" refers to a specific portion of a microfluidic device. In embodiments, a microfluidic trapping region is a portion of a microfluidic device which is used to collect or otherwise contain a specific molecule, ion or atom of interest.

The term "electrophoresis", as used herein, refers to the motion of particles or ions in a liquid by an electric field.

"Binding surface" refers to a portion of an object to which molecules or atoms bind. In some embodiments a binding surface is that part of an object which is functionalized or otherwise preferentially utilized to bind molecules or atoms.

"Bind" refers to a process in which an ion, atom or molecule is attached to a surface or otherwise held in the vicinity of a surface. "Selectively bind" refers to a process in which only a specific atom or molecule is induced to bind to a surface. Direct binding refers to a situation where a molecule, atom or ion binds to a surface with no intervening moiety; indirect binding refer to the binding of a molecule, atom or ion to other moieties attached to or otherwise bound to a surface.

"Fluid communication" refers to the relative orientation of two or more components such that an uninterrupted fluid path exists between the components.

"Electrostatic communication" refers to the relative orientation of two or more components such that an electric field is provided between the components, such as a uniform electric field.

"Electrical contact" and "electrical communication" refers to the arrangement of one or more objects such that an electric current (e.g., a flow of electrons or ions) flows from one object to another.

"Analyte" and "target analyte" refer to a molecule, compound, or species of interest which is present in a fluid. In certain embodiments, the presence and/or amount of an analyte or target analyte in a fluid is indicative of a condition in a system from which the fluid is obtained. Useful target analytes include, but are not limited to antigens, proteins, protein fragments, viruses, virus fragments, bacterium, bacterium fragments, hormones, illicit drugs, pharmaceuticals, lipids or any combination or metabolites of these The term "substrate" as used herein is intended to be consistent with the use of the term in relation to enzyme catalyzed reactions. A substrate is a molecule which undergoes a chemical reaction in the presence of a catalyst to form a detectable product.

"Catalyst" refers to a moiety which increases the rate of a chemical reaction. In some embodiments, a catalyst increases the rate of a single specific chemical reaction; in other embodiments, a catalyst increases the rate of multiple chemical reactions, for example a class of chemical reactions. "Enzyme" as used herein is intended to be consistent with use of the term in the fields of molecular biology and biochemistry. In general, an enzyme is a protein which increases the rate of a chemical reaction. In general, an enzyme is a catalyst. In some embodiments, a catalyst is an enzyme. "Catalytically active group" refers to a moiety which comprises a catalyst and can optionally comprise other components which do not impart catalytic activity.

A "catalytic chemical reaction" refers to a chemical reaction which takes place in the presence of a catalyst, thereby increasing the rate of reaction relative to that in which a catalyst is absent. "Bond cleavage reaction" and "bond breaking reaction" refer to a chemical reaction in which a bond between two atoms in a molecule is eliminated, for example resulting in a different chemical species where the two atoms have reduced interaction with or increased average distance from one another. A "bond forming reaction" refers to a chemical reaction in which a bond is added between two atoms, for example resulting in a different chemical species where the two atoms have increased interaction with or reduced average distance from one another. An "oxidation reaction" refers to a reaction in which the oxidation state of a specific molecular or atomic species is increased, for example by loss of electrons from the specific molecular or atomic species. A "reduction reaction" refers to a reaction in which the oxidation state of a specific molecular or atomic species is decreased, for example by addition of electrons to the specific molecular or atomic species.

"Directly producing" refers to forming a specific product molecule by means of a single chemical reaction. "Indirectly producing" refers to forming a specific product molecule by means of additional chemical reactions. In certain embodiments, an ionic species is directly produced from a catalytic chemical reaction. In certain embodiments, an ionic species is indirectly produced from a catalytic chemical reaction followed by another chemical reaction, such as a protonation or deprotonation reaction. In yet further embodiments, an ionic species may be indirectly produced from a catalytic chemical reaction followed by another chemical reaction such as oxidation, reduction, or covalent bond formation with a moiety possessing ionic charge (e.g., chemical derivitization).

The term "establishing an ionic charge" refers to a process in which an atomic or molecular species is provided with an ionic charge. In embodiments, a chemical reaction can establish an ionic charge of a reaction product.

"Reaction product" refers to an atomic or molecular species which is the result of a chemical reaction or a series of chemical reactions. In a specific embodiment, a "detectable reaction product" is a reaction product which has components which allow for the observation of the presence and/or number of reaction products. In embodiments, a detectable reaction product is observable by absorption of light, emission of light (e.g., fluorescence spectroscopy or chemiluminescence detection), electrochemical detection, and/or detection by surface enhanced Raman spectroscopy.

"Semi-permeable membrane" refers to a membrane which selectively permits specific chemical species to pass through while preventing or reducing the rate at which other chemical species pass through. In some embodiments, a semi-permeable membrane is size selective; that is, it permits chemical species having a size below a threshold size to pass through while preventing chemical species having a size above the threshold from passing through. In some embodiments, a semi-permeable membrane is molecular weight dependent; that is, it permits chemical species having a molecular weight below a threshold to pass through while preventing chemical species having a molecular weight above the threshold from passing through. In some embodiments, a semi-permeable membrane is chemically selective; that is, it permits only certain chemical species to pass through while preventing other chemical species from passing through or it prevents only certain chemical species from passing through while permitting other chemical species to pass through. In a specific embodiment, an electrically conductive semi-permeable membrane refers to a membrane which allows for electrical communication between electrodes positioned on opposite sides of the semi-permeable membrane, for example by passage of ions through the membrane. In certain embodiments, an electrically conductive semi-permeable membrane is itself composed of insulating (i.e., non-conducting) material, but has a structure allowing for the passage of ions and electrical communication through the membrane, for example by providing pores or passages capable of transmission of ions or solutions containing ions. In general, for most embodiments, semi-permeable membranes will always allow the passage of the small, charged molecules comprising a buffer (e.g., a molecular weight cutoff of >100 Daltons).

The term "antibody" as used herein is intended to be consistent with use of the term in the fields of biology, immunology, biochemistry, etc. The term antibody generally refers to a protein which selectively binds to a target analyte. "Antigen" refers to a chemical species or target analyte which binds to an antibody.

"Enzyme-antibody conjugate" refers to a molecule or chemical species comprising both an enzyme and an antibody, where both components retain at least a portion of their individual properties. In embodiments, for example, an enzyme-antibody conjugate binds to a specific antigen while also catalyzing a chemical reaction.

"Chromophore" refers to a portion of a molecule which absorbs light or is otherwise responsible for the color of the molecule.

"Chemiluminescent" refers to a chemical species which emits light as a product of a chemical reaction.

"Reagent" refers to an atomic or molecular species which takes part in a chemical reaction.

"Detection sensitivity" refers to the minimum signal that a detector or device is capable of distinguishing from noise. In embodiments, the detection sensitivity for a target analyte is the minimum concentration of target analyte in a solution which a system or device is capable of determining the presence of.

Systems and methods are described herein for detecting the catalytic reaction of an enzyme with a substrate, for example by directly detecting the catalytic reaction product. The detected reaction product can be used to infer the presence of the catalyst and if time dependent amounts of the reaction product are available, the amount of catalyst present in a system can also be inferred. Additionally, in systems where the catalyst binds to target analyte molecules, the presence and amount of target analyte in a system can also be inferred from the corresponding observation and amounts of catalyst.

The invention may be further understood by the following non-limiting examples.

EXAMPLE 1

Fabrication and Characterization of a Microfluidic Device

Device Fabrication. FIG. 1 illustrates an exemplary device embodiment in which the bottom substrates and cover plates were made from borosilicate glass, which were purchased from Telic (Valencia, Calif., USA). The bottom substrates were pre-coated with a thin layer of chromium followed by photoresist (protective layers). The channel design used for this study was patterned on a photomask, which was obtained from Fineline Imaging (Colorado Springs, Colo., USA). Standard photolithographic patterning was performed to transfer the channel design of the photomask onto the bottom substrates. Then, the photoresist layer was developed using MF-319 (Rohm and Haas) followed by etching the chromium layer using chromium etchant (Transene). All channel segments were initially etched to 2 μm using a solution of buffered oxide etchant purchased from Transene. In order to prevent further etching at the section of the membrane in the embodiment illustrated in FIG. 1, the portion was manually covered with a layer of photoresist. After the photoresist was dried out, the remaining channels were etched to 30 μm. Following this step, access holes were punched at the end of each channel segment using a micro-abrasive power blasting system (Vaniman). Then, the protective layers were removed using acetone followed by chromium etchant. The channels created on the bottom substrate were sealed with the cover plate using a sodium silicate solution (2.7% $SiO_2$, 1.4% NaOH by weight) as an adhesive layer. After applying pressure to these two plates, the excess sodium silicate solution in the channels was removed using a vacuum pump purchased from Thermo Fisher Scientific Inc. During this process, however, the solution still remained within the shallow region (2 μm) due to the larger capillary forces. Finally, the device was heated at 80° C. in a conventional oven at atmospheric pressure for 15 min. As a result, the sodium silicate solution in the shallow region formed a porous silica gel, which was used as a membrane that could trap resorufin. In order to enhance the plate bonding strength, the device was placed in the oven at 80° C. overnight.

Channel Coatings. First, sample reservoirs were attached to the end of each channel segment. Then, the channels were filled with 1 N NaOH for 60 min followed by rinsing with de-ionized water and acetone. The device was dried in the oven at 80° C. for 10 min. In this assay, reduction of the electroosmotic flow (EOF) in segment 2 of the embodiment shown in FIG. 1 was necessary, and this was done as follows: while a vacuum was applied at reservoir 2, solutions of N-(3-triethoxysilylpropyl)formamide and 3-aminopropyl triethoxysilane were introduced from reservoirs 4 and 1, respectively. The N-(3-ethoxysilylpropyl)formamide solution was prepared by mixing 1.8 mL of ethyl formate and 5.0 mL of 3-aminopropyl triethoxysilane followed by letting the mixture stand for 48 hours. Then, vacuum was removed and both solutions were allowed to flow by gravity for 45 min.

After rinsing the channels with methanol, segment 1 was ready for the ELISA coatings. To begin with, while vacuum was applied at reservoir 2, de-ionized water and 5% (w/v) glutaraldehyde were introduced from reservoirs 4 and 1, respectively. Vacuum was removed and these solutions allowed to flow by gravity for 45 min. Following this step, the solution in reservoir 1 was replaced with de-ionized water and vacuum was applied at reservoir 2 for a few seconds to rinse segment 1. The rest of the coatings shown in the following list were performed in the following manner: 100 mM (pH 7.4) phosphate buffer was used as the washing buffer in each of these steps unless otherwise stated.

1. 1% (w/v) bovin serum albumin (BSA) prepared with 100 mM (pH 9.4) carbonate buffer (60 min).
2. Wash the channel. Appropriate dilution of mouse anti-BSA solution prepared with 100 mM (pH 7.4) phosphate buffer (30 min). The mouse anti-BSA is the analyte in this assay.
3. Wash the channel. 40× dilution of biotinylated goat anti-mouse immunoglobulin (BioGenex, San Diego, Calif., USA) prepared with 100 mM (pH 7.4) phosphate buffer (10 min).
4. Wash the channel. 25× dilution of peroxidase conjugated streptavidin (BioGenex)/0.05% (v/v) Tween20 (10 min).
5. Wash the channel.

Device Operation. Initially, all channel segments were filled with 100 mM (pH 7.4) phosphate buffer. Then, the buffer in reservoir 1 of FIG. 1 was replaced with Amplex Red (10 μM)/$H_2O_2$ (5 μM) solution prepared with 10 mM (pH 7.4) phosphate buffer. Amplex Red was purchased from Invitrogen (Eugene, Oreg., USA). Reservoir 2 was filled with 100 mM sodium tetraborate. Vacuum was applied at reservoir 4 for a few seconds to obtain the initial flow profile of these two solutions. By removing the solution in reservoir 4, continuous pressure driven flow of Amplex Red/$H_2O_2$ and sodium tetraborate buffer was observed. After setting up the initial flow profile, the device was operated by applying voltages (e.g., 100 V-1000 V) at reservoir 3 and electrically grounding at reservoir 4 using an EMCO octo-channel high voltage system. In the ELISA region (segment 1), Amplex Red, which is a non-fluorescent dye, was converted to resorufin, which is a mixture of neutral resorufin and negatively charged resorufin anion at pH 7.4. The anionic form of resorufin is significantly more fluorescent than the neutral form. Introduction of the sodium tetraborate buffer from reservoir 2 converts all the resorufin to its fluorescent state, while at the same time enhancing its electrophoretic mobility. The dye molecules were visualized using a fluorescence microscope (Nikon, Japan). Due to the applied electric field, resorufin molecules were accumulated in front of the membrane, and the fluorescence signal around this region was collected using a CCD camera connected to the microscope. Finally, the fluorescence intensity was measured using Photoshop (Adobe Systems Incorporated) to quantitate the ELISA assay.

Figure 2A:
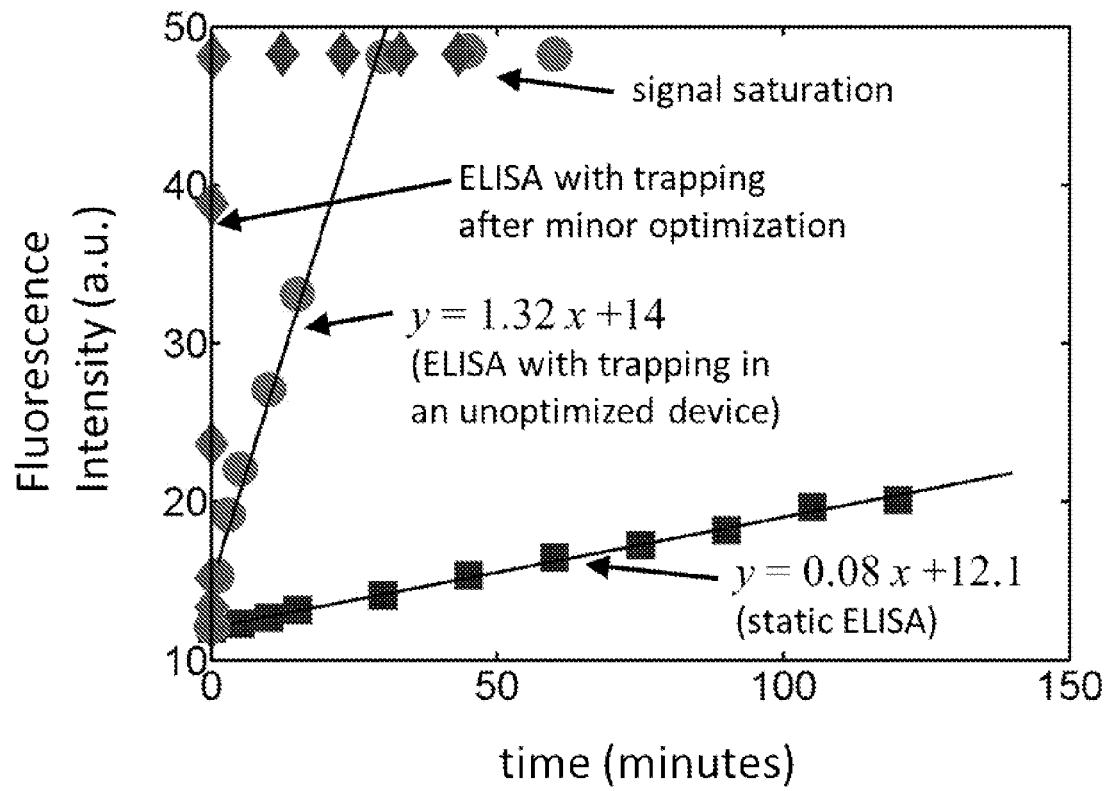
FIG. 2A provides data comparing achievable signal levels of static ELISA, an unoptimized device utilizing methods described herein, and an optimized device utilizing methods described herein.
Figure 2B:
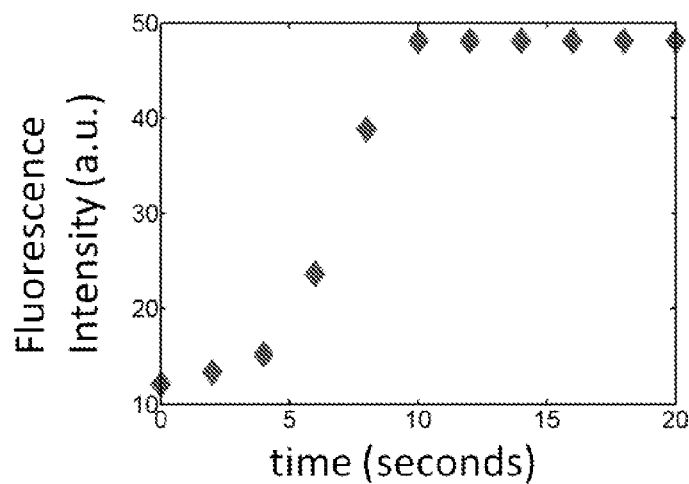
FIG. 2B is an expansion of the portion of FIG. 2A pertaining to signal levels achievable by an optimized device utilizing methods described herein.

The effects of the various variables (pre-concentration, pre-concentration with change in pH) are shown in FIG. 2A. Static ELISA data (squares) was obtained by observing fluorescence intensity directly in the ELISA region (segment 1). Simple application of a voltage while introducing pH 7.4 buffer through reservoir 2 (i.e., no pH change) with observation at the microfluidic trapping region immediately in front of the semi-permeable sodium silicate membrane produces a very significant increase in the rate of signal buildup (circles, "ELISA with trapping in an unoptimized device") associated with trapping anionic resorufin. The effect of combining pre-concentration with a pH change induced by introduction of pH 9.2 borate buffer through reservoir 2, is shown by the diamonds ("ELISA with trapping after minor optimization"); fluorescence saturation is achieved in <10 seconds, as shown in FIG. 2B, representing a ca. 3000× improvement in signal intensity over the static ELISA conditions.

EXAMPLE 2

Pre-Concentration Using a Microfluidic Device

This example describes a relatively simple method that allows the sensitivity of ELISA methods to be improved. The described methods for sensitivity enhancement that extend currently available detection methods are attractive, as they retain the versatility inherent in the variety of detection methods, while still improving them. This improvement dramatically increases the already high utility of ELISA methods, and opens up new possibilities for detection in research and clinical applications.

In the broadest sense, the present example provides methods and compositions for detecting and measuring the abundance of suitable molecules in a process that comprises the steps of establishing an ELISA surface in a microfluidic channel wherein an analyte can be bound and there is approximately one catalyst (e.g., enzyme) for each analyte, and then providing a flow of substrate solution for the catalyst, some portion of which is converted by the catalyst to a charged detectable reaction product having a different net charge than the substrate. Embodiments further comprise the step of providing a microfluidic side channel downstream from the analyte/catalyst region, wherein this microfluidic side channel is provided with a semi-permeable membrane that does not allow the passage of the detectable reaction product, as well as an electrode behind the semi-permeable membrane that is of opposite polarity relative to the net charge of the detectable reaction product, and is established at a potential sufficient to attract the detectable reaction product into the microfluidic side channel where it is trapped and thereby concentrated at or near the surface of the semi-permeable membrane. Additionally, an embodiment comprises the step of providing a means for detection of the detectable reaction product at or near the semi-permeable membrane, and the step of carrying out that detection after a predetermined time interval, or at a series of time intervals and recording the magnitude of the signal associated with the detectable reaction product.

When the methods described in this example are applied as summarized above and described in detail below, they result in the detection of suitable molecules of interest with much greater sensitivity and/or rapidity than current ELISA methods; increases of 100-fold are typical, and greater than 1000-fold increases are not uncommon. This increase in sensitivity and/or rapidity is a consequence of the concentration into a small volume the detectable product of the enzyme (or other catalyst) catalyzed reaction that occurs as an outcome of the operation of certain embodiments. It is an axiomatic principle of analytical chemistry that an increase in concentration will provide an increase in assay sensitivity, and the sensitivity of all assays are defined, in at least some respect, in terms of concentration. Concentrations may be described in a number of different fashions that vary according to the field of interest: in science, concentrations are most commonly given in molarity (moles per liter, or M), but it is not uncommon to encounter concentrations based on a weight per unit volume or weight per unit weight (e.g., mg/L or weight percentages, respectively). The origin of this effect has to do with signal-to-noise ratio (S/N). Assuming appropriate instrumentation, in the absence of noise, a microgram of a substance dissolved in a swimming pool (very low concentration) should be detected with the same sensitivity and fidelity as that same microgram dissolved in a microliter of solution (very high concentration): after all, the absolute amount of material is precisely the same in each instance. However, background noise associated with the large volume of the swimming pool sample matrix (or the cross sectional area of the interrogating radiation and accompanying detector) will result in noise that will obscure the signal coming from the target analyte.

It should be possible to increase the sensitivity of any assay by simply increasing concentration. For example, the solvent of a sample matrix (e.g., water) can be removed by evaporation, or the mixture filtered through a medium that allows passage of the solvent but not the materials dissolved in it. However, while these methods may improve S/N through removal of the noise associated with the solvent (and the accompanying noise associated with larger analysis volume), they do not remove another very important source of noise: the background noise associated with the other materials dissolved in the sample matrix. For example, if a sample from a typical ELISA assay were to be simply concentrated by evaporation, all of the salts, buffers, and ELISA substrate would still be present after the concentration process and provide interfering noise that would lessen the S/N with respect to the ELISA reaction product. The ELISA substrate, in particular, is expected to provide a particularly high level of background noise; while most reactions employed in ELISA methods involve a dramatic change in the signal associated with the reaction product vis-a-vis the substrate, it is nevertheless the case that the substrate has some measurable level of interfering signal associated with it. Filtration may be superior to simple concentration by evaporation, since it will usually be the case that salts and buffers will pass through the filtration medium, but it will generally be the case that the substrate for the ELISA reaction will be retained along with the product, leading to some level of noise obscuring the signal of the ELISA reaction product. Both of these methods of concentration suffer from the additional disadvantage of being inconvenient (requiring sample manipulation) and time consuming.

A technique that provides some of the advantages of sample concentration without the necessity of separate operations is to employ an ELISA reaction substrate that produces a product that precipitates from the reaction medium to give a coating on the surface of the assay apparatus; if a method of detection is available that allows for focusing at the surface at which the precipitation has occurred, this technique can provide high detection sensitivities. However, this method also has disadvantages. These include substantial limitations with respect to the range of enzymes and ELISA reactions that can be employed (since in addition to the usual requirements of ELISA methods, the catalyzed reaction must produce an insoluble product), the fact that the insoluble product formed is typically the result of bimolecular, or polymerization reactions requiring complex kinetics, leading to loss of potential signal-producing reaction product through side reactions. In addition, deposition of the reaction product cannot truly be confined to a narrowly defined area (due to diffusion of the initial reaction product intermediates and the precipitate), and some signal is likely lost because of some limited level of solubility of the reaction products in the medium. Finally, since the precipitated product is being viewed on a surface with intervening solution, there will be some level of background noise associated with the ELISA substrate and other assay components.

The methods and compositions described herein allow for concentrating ELISA (or other catalyst) reaction products while circumventing many of the problems associated with the concentrating methods described above. The concentrating effect of embodiments described herein relies on a combination of a number of factors. Foremost amongst these factors is the practicality of moving charged molecules through electrophoresis when they are in a microscale environment. For the operation of certain embodiments it will generally be the case that capillaries and micro-/nanofabricated channels with hydraulic diameters ranging from 1 centimeter to 10 nanometers will be useful for particular embodiments, with the most commonly used diameters being 1 mm to 100 nm. Although in principle, charged molecules can be moved electrophoretically in channels larger or smaller than this prescribed range, several practical issues may limit the ability to operate at those dimensions. For example, at the macro-scale the larger amount of electrical power required to accomplish the desired movements of molecular species may degrade the performance and/or reliability of the ELISA assays due to Joule heating effects, or in some instances lead to damage to the semipermable membrane. At the other extreme, i.e., for conduits smaller than 10 nanometers in diameter, there may be limited ability to control the channel features, e.g., membrane dimensions, as well as the strong surface interactions around them, which may hinder implementation of assays in a reproducible manner. On a practical basis, clogging of especially small channels may represent a significant problem, especially when dealing with biological samples.

Figures 3A, 3B:
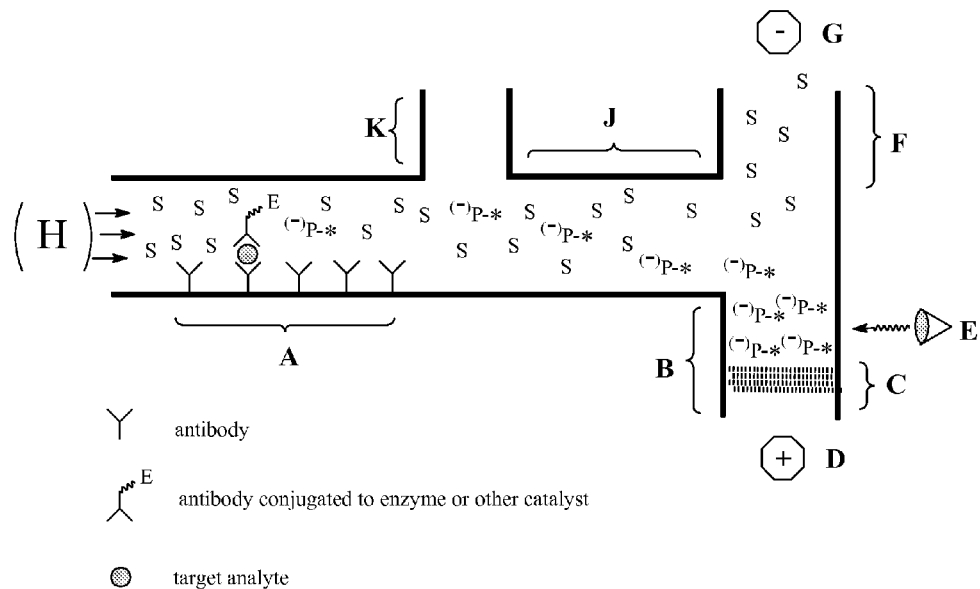
FIG. 3A provides a schematic illustration of an exemplary device embodiment.
FIG. 3B provides a legend for FIG. 3A.

The ability to effect the mobility of charged species, in combination with certain carefully chosen characteristics for a catalyzed substrate-to-detectable product reaction, in further combination with the presence of a semipermeable membrane capable of blocking the movement of the detectable reaction product, provides a means for very rapidly improving the sensitivity of an ELISA type assay. The operation of one embodiment can be illustrated using the same type of "sandwich"-type ELISA assay discussed in the Background, and is illustrated in FIG. 3A. FIG. 3B provides an additional legend for elements in FIG. 3A. As will be noted in the discussion that follows, FIG. 3A includes two elements that are not absolutely necessary for the practice of all embodiments, but which facilitate operation and would be included in specific embodiments; so as to make later explanations more readily understandable, these two optional elements are included in FIG. 3A.

The device described in this example comprises, at a minimum, two microfluidic channels. In FIG. 3A, one of the two channels (the main channel) includes regions A, optional region J, and region F, while the second of the two channels (the "trapping channel", also referred to herein as the "microfluidic trapping region") is labeled as B; as noted below, the two channels may be arranged in other geometries than that shown here. In the example given here, region A comprises what will be termed here an "ELISA region," but may be more broadly described as a binding region. In an assay, this region is formed by using methods known in the art to attach antibodies to the surface of the channel in region A, followed by a wash and subsequent exposure to a sample containing the target analyte of interest (delivered from reservoir H), wherein the analyte will bind to at least some of the antibodies. After a suitable incubation period, the channel is washed again (from reservoir H) to remove excess sample matrix, and then a second antibody, conjugated to an enzyme or other catalyst, is introduced so as to form a sandwich complex between the first antibody, the antigen/target analyte, and the antibody-enzyme conjugate. A final wash to remove excess antibody-enzyme conjugate will provide the ELISA region, A, in which there is bound analyte, and approximately one enzyme/catalyst for each analyte. Of course, this description is of a particular embodiment; implementation of different variants of the ELISA reaction known in the art would lead to different means of forming the ELISA surface.

A microfluidic side channel, B (the trapping channel), comprises a semipermeable membrane, C, that allows the passage of small ions such as inorganic buffer components, but that traps larger molecules such as the detectable ELISA reaction product $^{(-)}$P* in a detection zone that includes the face of the semipermeable membrane and extends out some small distance, though typically not as far as the main microfluidic channel. On the side of this membrane opposite to the main microfluidic channel (the rear, or back side) there is an electrode, D, the polarity of which is chosen to be opposite to that of the detectable ELISA reaction product. In the example given here, the detectable ELISA reaction has been arbitrarily assigned a negative charge, and thus the electrode D is set to a positive potential (high voltage). The potential at electrode D is sufficiently high that it can strongly attract the detectable ELISA reaction product $^{(-)}$P* even in opposition to a pressure driven flow passing from reservoir H through the waste channel F. In the example provided here, this is a ground. Microfluidic channel B is also provided with a detection system E that is placed so as to detect species at or near the surface of semi-permeable membrane C. The electrode complimentary to D is electrode G, shown in FIG. 3A at the end of waste channel F. A general purpose reservoir/entry portal is provided at H, which is used to supply the various components of the assay (e.g., the analyte containing sample, the antibody-enzyme conjugate, the various wash solutions, and the ELISA reaction substrate, etc.). Components J and K (a downstream channel and an auxiliary microfluidic channel) are not essential for the operation of all embodiments, but as will be discussed in detail below, will typically be included since they may be useful for the purpose of establishing the ELISA region, as well as for implementation of a variety of other useful embodiments. The choice of substrate, S, and ELISA reaction provides advantages of the methods and devices described herein, since separation from and concentration of the detectable ELISA reaction product $^{(-)}$P* is accomplished by a difference in net charge between the substrate and product of the catalyzed reaction.

Following establishment of the ELISA region as described above and washing to remove excess antibody-enzyme conjugate, a substrate for the enzyme is introduced by pumping or by simple hydrostatic pressure as a solution in an appropriate buffer for the reaction. The enzyme present will then convert some small fraction of the substrate to a detectable product having a different net charge. In the example given here, the substrate is neutral, while the product has a single negative charge. Both substrate and product will be carried through the microfluidic channel by pressure driven flow, but the negatively charged detectable ELISA reaction product will also experience an attractive force from electrode D that is at a positive potential and will thus be drawn towards semipermeable membrane C, where it will collect at, or near the membrane surface and be measured by detection device E. Since the substrate, S, is not charged, it will not be attracted to electrode D and instead will be carried with the bulk solution towards waste. Thus, through this process, the detectable ELISA reaction product is concentrated in a small volume (increasing the signal in the signal-to-noise ratio, S/N), while at the same time other assay components (most particularly the substrate S) are carried away from the detection region at the face of the semipermeable membrane (decreasing the noise in the signal-to-noise ratio, S/N). The combination of signal increase through concentration, with noise decrease through separation from the other assay components, leads to an enormous increase in S/N and a consequent dramatic improvement in the limit of detection for the analyte. Compared with a conventional ELISA method without this simultaneous separation and concentration, this method provides more sensitive detection and/or more rapid detection.

A specific example of one embodiment is the use of the commercially available ELISA substrate Amplex Red® for an ELISA reaction using horseradish peroxidase as the enzyme. Thus, the mouse antibody to BSA can be detected as follows. An ELISA surface is established in a microfluidic device of the form described in FIG. 3A, in which the regions J and F have been coated with N-(3-(triethoxysilyl)propyl) formamide to reduce electroosmotic flow. The semipermeable membrane C is comprised of silica, and the detection device used is a fluorescence microscope with a high-pressure mercury lamp as the excitation source (spectral range 184 nm to 577 nm). The fluorescence signal is collected in this set-up by exciting the analyte molecules with a light beam from the mercury lamp after passing it through a low pass optical filter (transmitted wavelengths <540 nm) and then collecting the fluorescence signal with a CCD camera that has a high pass optical filter (transmitted wavelengths >600 nm) placed in front of it. Solutions are provided to the device using a well, and flow is a result of simple hydrostatic pressure. The ELISA surface comprises a coating of BSA that has been bound to the glass surface by first reacting the cleaned glass surface with aminopropyltriethoxysilane, followed by aqueous glutaraldehyde (and a wash step), followed by BSA (and a wash step), followed by a basic solution of sodium borohydride (and a subsequent wash), to provide a surface in which the BSA is covalently bound to the surface. The thus formed BSA surface is exposed to a solution containing some amount of mouse anti-BSA antibody, the mixture allowed to incubate, after which it is washed with buffer to remove excess substrate solution. A solution of biotinylated goat anti-mouse antibody in buffer is then introduced, and after about thirty minutes of incubation, the channel washed with buffer. A solution of streptavidin-horseradish peroxidase in buffer is then introduced, the mixture allowed to incubate, and the channel then washed with buffer, thereby providing the ELISA surface of this embodiment, comprising a quaternary complex of (glass-linker-BSA)-(anti-BSA antibody analyte)-(goat anti-mouse/biotin conjugate)-(horseradish peroxidase/streptavidin conjugate). A solution having 10 µM Amplex Red® and 5 µM hydrogen peroxide in 0.1 M pH 7.4 phosphate buffer is then introduced while applying a positive potential at electrode D. As is known in the literature, horseradish peroxidase converts Amplex Red® to the fluorescent and readily detectable anion of the dye resorufin under these conditions, as illustrated in the below scheme:

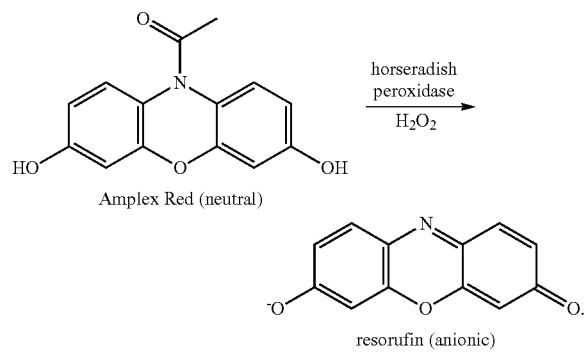

Amplex Red (neutral) → resorufin (anionic)

The anionic dye is selectively drawn towards the cathode D, where it is trapped and concentrated at membrane C; unreacted Amplex Red®, being uncharged, is not influenced by the electric field, and continues with the bulk of the solvent through regions J and F to waste. Signal is then detected at varying intervals at the face of the semi-permeable membrane. The signal so-produced by the separation/concentration effects is improved by >10-fold relative to that produced in control experiments in which the detectable ELISA reaction product is formed without the product separating/concentrating effect of the electric field and membrane present. In the context of a pH change embodiment, described below, dramatic signal enhancements of greater than 1000 fold are achievable.

The above-described embodiment represents a dramatic improvement over current ELISA methodology. Other embodiments may provide even greater advantages for some circumstances. In another embodiment, the substrate and detectable ELISA reaction product do not simply differ in net charge, but have differently signed charges. For example, use of a positively charged substrate that is converted in a catalyzed reaction to a negatively charged detectable ELISA reaction product ($^{(+)}S \rightarrow {}^{(-)}P^*$) will provide improvements in S/N relative to the originally described assay, and thus improve assay sensitivity and/or speed. The source of this improvement lies with a decrease in noise associated with the presence of substrate in the detection zone. In some embodiments, substrate is separated from detectable ELISA reaction product $^{(-)}P^*$ by a fairly passive process: it moves along with the rest of the material in the pressure driven flow directed out of the waste channel. However, just as debris may collect in inlets or cavities in a stream, substrate may also passively diffuse and be trapped in regions of stagnant flow, as in the detection zone for $^{(-)}P^*$, thereby increasing background noise. On the other hand, in the $^{(+)}S \rightarrow {}^{(-)}P^*$ embodiment described here, the positively charged substrate $^{(+)}S$ is actively repelled from the detection zone and attracted to the waste channel, thereby effecting a complete separation of substrate from the detectable ELISA reaction product. The complete absence of noise producing substrate from the detection zone leads to an improved S/N, and thus assay sensitivity. This embodiment can be readily implemented by a simple modification of the structure of Amplex Red® to provide the substrate shown in the below scheme; this substrate may be synthesized in a fashion similar to that reported in the literature (reduction of resorufin with zinc, then acetylation with acetyl chloride, followed by controlled hydrolysis), except that in place of acetyl chloride, the acid chloride of N,N-dimethylglycine would be employed, and the product methylated with dimethyl sulfate or iodomethane.

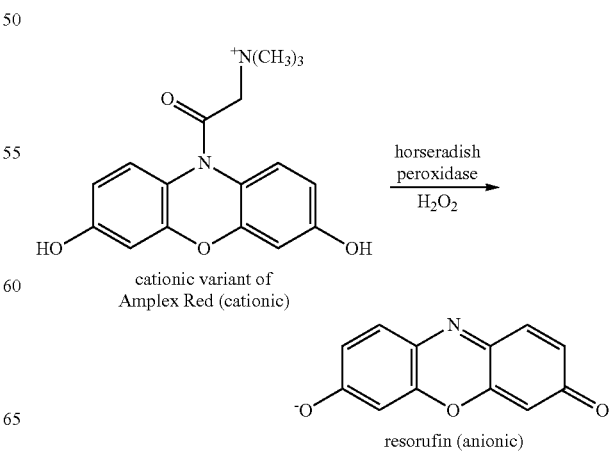

cationic variant of Amplex Red (cationic) → resorufin (anionic)

The methods and compositions of the present example include embodiments that further, and even more greatly, distinguish it from current ELISA methods. Thus, an embodiment comprises the use of ELISA substrates that contain highly detectable dye components that are not acted upon by the enzyme that is central to the ELISA method. Current ELISA methods rely on an enzyme catalyzed reaction in which a non- or poorly-detectable substrate is converted to a dye—a highly detectable species. This feature is necessary in current ELISA methodology because the assay is conducted in such a way that the substrate and detectable ELISA reaction product are in the same solution at the same time, and remain so throughout the assay. If a detectable dye were already present in the substrate, it would not be possible to distinguish between the substrate and the detectable ELISA reaction product, and there would be no way of telling that an enzyme catalyzed reaction had occurred; thus, the assay would not produce signal in a way that was related to the amount of enzyme (and by inference, substrate) present, and would be of no use. The requirement in current ELISA methodology that a non- or poorly-detectable substrate be converted by an enzyme to a highly detectable ELISA reaction product leads to a number of undesirable constraints and consequences for the methods. One of these is that the detectable component (typically, a dye) in the detectable ELISA reaction product is principally optimized not for its detectability, but rather the ability to be formed in an enzyme catalyzed reaction. This is a very logical constraint for current ELISA methodology: if the detectable dye can't be formed from a non- or poorly detectable substrate in an enzyme catalyzed reaction, it doesn't matter how good it is, since the assay will be doomed to failure for the reasons outlined above. Thus, there are dyes known that can be detected with fantastically high sensitivities, but these are not employed as the detectable component of the detectable ELISA reaction product because there isn't a reasonable/possible method for forming the dye from a non- or poorly-detectable substrate in an enzyme catalyzed reaction. It is useful to have an ELISA based method for detection that does not have this constraint with respect to dye structure. It should be noted that there have been reports of ELISA reactions that involve subsequent purification of the reaction products (e.g., by electrophoresis or HPLC), but these do not specifically rely on the charge changes necessary for certain embodiments; nor are these methods suitable for operation in a continuous mode that allows for repeated data collection. Since repeated/semi-continuous data collection provides data of greater precision and accuracy than obtained by single point measurements, the methods of the present example, that do allow for continuous separation, may be considered useful and novel.

Closely related to the constraints and consequences having to do with the detectable component of the detectable ELISA reaction product is the nature of the enzyme catalyzed reaction. The vast majority of ELISA assays involve reactions of two general types: oxidation reactions that convert non-dyes to dyes, and hydrolytic cleavage reactions that involve breaking a bond to an atom that is an integral component of the dye chromophore, or to an atom that allows a chemiluminescent reaction to proceed. Oxidation reactions may involve the combination of two or more subunits to give a colored (dye) product, or may involve the conversion of a single molecule to a dye (e.g., oxidation of a leuco dye). In the former case, dye formation may not be as efficient as desirable, since some of these processes typically involve an initial oxidation step to give a highly reactive intermediate that then has to encounter its reactive partner; if the highly reactive intermediate first encounters some other species capable of reaction, then a decreased (or no) signal for that oxidation reaction will be observed. If the oxidation involves conversion of a leuco dye (or leuco dye derivative) to a dye, there may often be stability problems in the substrate that lead to decreased S/N for the assay. Specifically, many leuco dyes (and leuco dye derivatives) will undergo non-catalyzed oxidation reactions to give dye products. This means that during the long time periods that are commonly required in ultra-trace analyses, signal will be produced that is not associated with the presence of enzyme (and by inference, analyte). The result is that a misleadingly high signal is produced, leading to an incorrect indication of analyte presence or concentration. While this problem can be dealt with to a certain extent by comparison to a control reaction, this nevertheless represents a serious problem for the analysis of samples having extremely low levels of analyte.

ELISA methods in which the enzyme catalyzed reaction involves a hydrolytic cleavage reaction generally require that the bond being cleaved be between an atom that is integral to the chromophore of the dye-to-be and a blocking group. Usually, this atom is oxygen. It is typically the case that the dyes produced in these reactions are of a type that show substantially different properties depending on the electron donating ability of the above mentioned atom. Examples of this are illustrated below for two very common ELISA reactions and substrates:

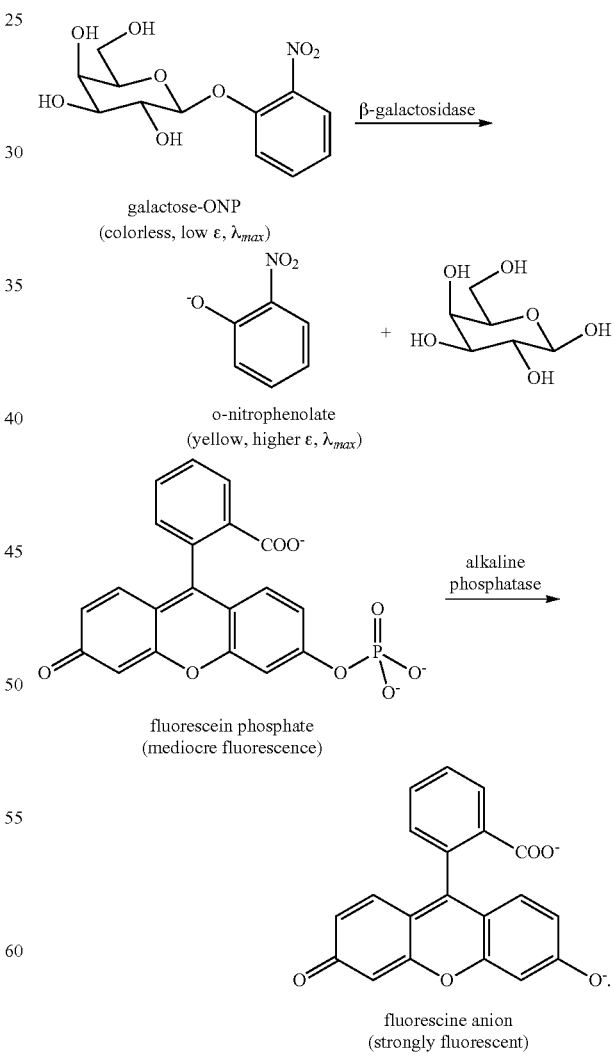

In the first of these examples the o-nitrophenyl acetal of β-galactose (galactose-ONP) is cleaved by the enzyme β-galactosidase to (under the conditions of the assay) the anion of o-nitrophenol. While neutral o-nitrophenol and its esters or acetals are colorless, with fairly low values of $\lambda$max (~354 nm), the corresponding anion is yellow, having a $\lambda$max that has shifted to much higher wavelengths (~432 nm), and with a larger extinction coefficient, $\epsilon$. Thus, when $\beta$-galactosidase is conjugated to an antibody, it can be used in ELISA methods employing galactose-ONP as the substrate producing a detectable ELISA reaction product o-nitrophenolate. A more sensitive assay involves the formation of a fluorescent detectable ELISA reaction product. The molecule fluorescein exhibits pH dependent fluorescence wherein fluorescence is significantly enhanced under basic conditions, where one of the oxygens of the aromatic ring is negatively charged (and thus a better electron donor). Blocking of one of the aromatic ring oxygens as an ester (a phosphate ester is shown, but other types of esters can be used depending on the enzyme and substrate employed in an ELISA method) provides an ELISA substrate that has only mediocre native fluorescence. However, when this ester is cleaved under basic conditions, the resulting fluorescein anion is produced, which has a much higher degree of fluorescence than the starting ester. This is the basis of a large number of ELISA assays that use fluorescein phosphate in conjunction with antibodies conjugated to the enzyme alkaline phosphatase. It is worth noting at this juncture that, while both of the reactions shown above involve taking substrate molecules and converting them to detectable ELISA reaction products, the nature of what makes them detectable is different than what makes them detectable according to the methods and practices described herein. In these examples of conventional ELISA methods, the net charge state relative to the substrate doesn't matter; rather, it is the change in electron donating ability by the oxygens that occurs in the hydrolytic cleavage process that leads to the increase in detectability. In certain embodiments described herein, while it is true that the products of these reactions will be more readily detectable, it is the fact that they differ in charge from their respective starting substrates that allow them to be selectively separated from the substrates and concentrated.

Although strategies of the type described above have led to a number of very impressive assays having excellent detection sensitivities, the fact that the signal producing reaction requires a hydrolytic cleavage involving a critical atom directly attached to the dye chromophore imposes a number of undesirable restrictions. In particular, this strategy leads to limitations in the types of dyes that can be used, as well as restrictions on the number and types of enzymatic reactions that can be employed. The preference for dyes that can be unmasked by hydrolytic cleavage of a C—O bond limits the designer of such assays to certain classes of dyes. In many cases, improvements to dyes have required substantial redesign of many aspects of the dye skeleton—at great effort and expense—while always keeping the crucial to-be-blocked oxygen untouched. In other words, the dye is being optimized with respect to its ability to be cleaved in a way that leads to an increase in signal, as opposed to being optimized with respect to its ease of detection by whatever method has been chosen. For example, some vendors have gone to great efforts to modify the fluorescein molecular skeleton so as to give higher excitation and emission maxima. While there are many dyes available that have fluorescent characteristics far superior to fluorescein (or its modified versions), they are not used because they are not well suited for incorporation into substrates in such a way that the enzyme catalyzed ELISA reaction leads to an unmasking of some critical atom, resulting in a large increase in fluorescence (or UV) intensity. It is preferable to optimize the detectable component of the detectable ELISA reaction product for the detection method, as opposed to optimizing it with respect to the enzyme catalyzed reaction. As will be discussed below, embodiments allow this detection-centered optimization.

A second disadvantage of relying on an atom-unmasking strategy for signal generation is that there are inherent limitations with respect to the types of enzyme reactions that can be employed for the ELISA process: not only must they involve cleavage of a bond between carbon and an atom integrally part of the chromophore (generally, cleavage of a C—O bond), but the enzyme must be able to tolerate functionality and steric effects on either side of this critical bond. In particular, the substrate must be able to tolerate what is generally a fairly large dye chromophore. A further practical limitation of certain current ELISA methods has to do with the kinetics of the enzyme reaction. Both of the most common enzymes used in certain current ELISA methods (alkaline phosphatase and horseradish peroxidase) have been characterized by some as near "perfect" enzymes due to their extremely high rates of signal producing substrate-to-product turnover. Assays using these enzymes often produce an acceptable level of assay sensitivity after 20-100 minutes. There are certainly other enzymes that will catalyze qualitatively similar bond cleavage and/or oxidation reactions producing large chromophoric changes, but they may do so at rates that are ten- to thousand-fold times slower. Implementation of such enzymes in ELISA assays would require the user to wait days or weeks for their results, and make such assays impractical and undesirable.

When one considers that current ELISA methods must proceed by an enzyme catalyzed reaction that requires either oxidation of a leuco dye, or cleavage of critical C—O bond in which the oxygen is attached to a dye chromophore in such a way that this cleavage results in a dramatic change in the detectable properties of the chromophore, and that the enzyme has to operate at a rate that provides a readily detectable signal in the space of tens of minutes to a few hours, it is actually surprising that there are even the three classes of enzymatically catalyzed reactions in common current use (reactions catalyzed by horseradish peroxidase, alkaline phosphatase, and $\beta$-galactosidase). Yet, there is a compelling reason for wanting to have a broader range of enzymatically catalyzed reactions available for ELISA assays: the possibility of analyzing for multiple analytes simultaneously. Since enzymes show very high selectivity with respect to the reactions they catalyze, it should be possible to have an ELISA based assay platform in which there are antibodies of multiple types binding analytes of multiple types; and, it should then be possible to introduce appropriate substrates for all of the enzymes involved in the multiple assay, thereby allowing for their simultaneous detection. Such a capability would be of particular value in the case of fundamental research, when either multiple biochemical pathways are being monitored simultaneously, or when multiple steps of a single pathway are being monitored.

Accordingly, the methods and practice described herein allow for embodiments in which it is possible to incorporate detectable components in the ELISA substrate that are substantially unaltered in the course of the ELISA reaction. In addition, there are embodiments in which the enzyme catalyzed reaction does not involve cleavage of bonds to the detectable component of the ELISA substrate. In addition, there are embodiments involving cleavage of bonds to the detectable component of the ELISA substrate by enzymes that catalyze such bond cleavages at rates that are much slower than the rates of bond cleavages involving commonly employed enzymes in ELISA assays. Further, there are embodiments that facilitate the operation of multiple ELISA assays in a simultaneous fashion in the same environment.

The ready separation (and concentration) of the detectable ELISA reaction product from the substrate for the reaction greatly widens the scope of enzymes and the corresponding reactions, as well as the substrates that can be employed in the ELISA component of certain embodiments. The only requirement (beyond those usually attendant on an enzyme in an ELISA reaction) is that the reaction catalyzed produce a net change in charge state between the substrate and the detectable ELISA reaction product, though as will be seen below in the Detailed Description, some changes in charge and absolute charge are likely to be more useful than others. Two embodiments that illustrate some advantages vis-á-vis current ELISA methodology are as follows. It should be noted that even with respect to the embodiments of the invention described to this point, a substantial broadening of the number of enzymes available for ELISA assays is achieved. The >10-fold improvement in detection sensitivity described above, and the >1000-fold improvement that is achieved using the pH change described below, means that enzymatically catalyzed reactions that proceed at rates much slower than those found with the near-perfect alkaline phosphatase will produce signal at a very acceptable rate, since this signal will be enhanced by the pre-concentrating effects of localizing the charged detectable ELISA reaction product in a trapping zone. For example, pig liver esterase (a.k.a. porcine liver esterase) and rabbit liver esterase have fairly broad substrate specificities and have been assayed using substrates that undergo a substantial chromophoric change on reaction. While these enzymes have not been commonly employed in ELISA reactions due to their relatively (compared to HRPase and APase enzymes) slow rates, concentration of charged product allow their use in a practical sense with the methods described herein. Indeed, possible candidate enzymes for use in the methods described herein will include virtually any enzyme for which a fluorescent assay has been described for characterizing its activity.

As noted above, workers in the field of immunoassays have spent considerable time and effort in altering dyes so as to improve the detectability of the ELISA reaction product, while still retaining an oxygen integral to the dye chromophore that plays a direct role in the enzyme catalyzed reaction. Often, the goal of these modifications is to increase the emission wavelength of the dye, so as to avoid background fluorescence from the sample. Fluorescein has an excitation maximum at 488 nm, with an emission at about 525 nm. Tetramethyl rhodamine isothiocyanate is a commercially available dye that is readily converted to a wide variety of derivatives due to the presence of the amine-reactive isothiocyanate group, and which has significantly superior fluorescence properties relative to fluorescein, with excitation and emission wavelengths of 557 nm and 576 nm, respectively. It does not appear to be in use in ELISA assays, presumably because it is not well suited for conventional enzyme catalyzed reactions, since it lacks an oxygen attached directly to the chromophore that can be phopshorylated or otherwise derivatized. However, as shown in the below scheme, an embodiment can readily make use of this inexpensive compound for detection of analytes:

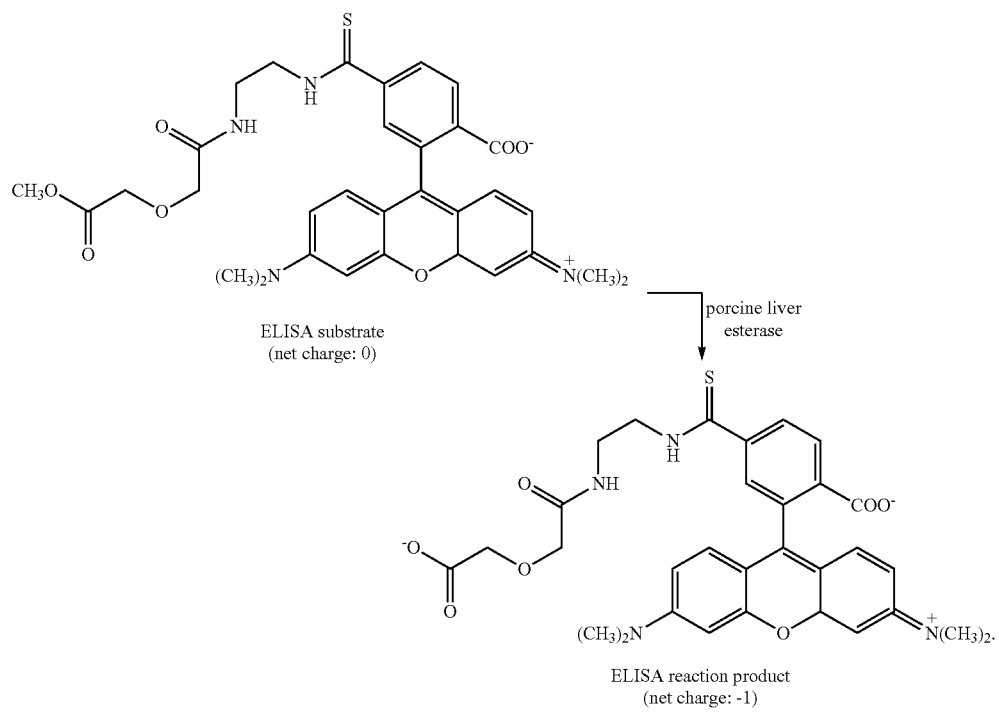

ELISA substrate
(net charge: 0)

porcine liver esterase

ELISA reaction product
(net charge: -1)

Thus, tetramethyl rhodoamine isothiocyanate (TRITC) can be converted to the ester derivative shown below by coupling it in the presence of diisopropylethylamine with an amino ester prepared by reacting glycolic anhydride with excess ethylenediamine, removing the excess diamine under high vacuum, and Fisher esterification of the amino acid using methanol/dry HCl.

The enzyme component of this embodiment of the assay is porcine liver esterase (PLEase), an enzyme having broad specificity and high reactivity for the cleavage of a variety of esters, and especially methyl esters, to the corresponding acid salts. The enzyme has also proven adaptable in the sense that it can be conjugated to other compounds (including surfaces) while retaining the bulk of its reactivity. In this embodiment, a substrate that is initially neutral overall is converted to a detectable ELISA reaction product that has a net negative charge, making it readily separated and concentrated as described above. Although well suited to the methods described herein, this substrate would not be appropriate for current ELISA methodology, since the enzyme catalyzed reaction does not occur at or near the detectable component of the substrate/product, nor is the detectable component altered in any significant fashion in the course of the enzyme reaction. Furthermore, as noted above, PLEase catalyzes reactions at a rate that is inconvenient for most assays. However, the pre-concentration aspect of the current assay removes this disadvantage, allowing good signal detection in a short period of time.

The above described embodiment illustrates the use of an enzyme in the ELISA component of the assay that is not typically employed in current ELISA methodology. It is also possible to make use of enzymes that are in use in current ELISA methods, yet which operate in a way that is not compatible with current ELISA methods, since they do not result in any significant change in chromophoric properties as a result of the enzyme catalyzed reaction. Instead, these embodiments rely on the ready separation/concentration of the ELISA reaction product. A substrate and enzyme catalyzed reaction for this embodiment are shown below:

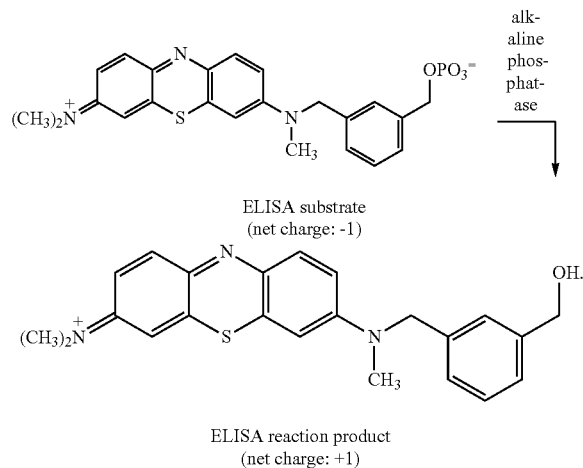

The ELISA substrate for this reaction may be prepared by alkylation of the commercially available dye Azure B with 1-acetoxymethyl-3-bromomethylbenzene (prepared by a statistical acetylation of commercially available benzene-1,3-dimethanol and reaction of the monoacetyl compound with phosphorous tribromide in pyridine/chloroform, followed by saponification of the acetoxy group and phosphorylation of the resulting hydroxyl group, e.g., by reaction with ((Me$_3$SiCH$_2$CH$_2$O)$_2$PN(iPr)$_2$/methyl tetrazole, then oxidation with hydrogen peroxide, then deprotection with HF(aq)/acetonitrile). The enzyme used in this embodiment is alkaline phosphatase, one of the most commonly employed enzymes in current ELISA methodology. In current ELISA methodology, this enzyme is used with phosphate monoesters of dyes in which the oxygen that is linked to the phosphorous is a critical component of the dye chromophore; this is necessary to achieve the dramatic change in chromophoric properties required by current ELISA methods. In fact, alkaline phosphatase shows extremely broad substrate tolerance, with alkyl and branched alkyl phosphate monoesters being hydrolyzed at rates comparable to phenolic phosphates. In this embodiment, alkaline phosphatase acts at a position remote from the chromophore, and without altering it. However, in the course of this transformation the substrate goes from a charge state of −1 to +1, corresponding to the very desirable situation described above in which the substrate is actively removed from the trapping zone. This is particularly desirable in the embodiment discussed here: since there is no difference in the chromophore in the ELISA product from that in the substrate, it is particularly desirable to employ an embodiment in which complete separation of the two can be expected.

Embodiments also exist that are well suited for the simultaneous measurement of two or more analytes in a process that provides extremely high sensitivity. In those applications in which two analytes are to be measured, the ELISA region comprises a mixture of antibodies corresponding to the analytes, and enzyme conjugates corresponding to the two analytes can be used as well. The enzymes used for the two different ELISA detection methods can be different, as can the substrates. The detectable component of the ELISA product may or may not be different, as described below. With respect to the separation and concentrating aspects, any of three broad strategies may prove advantageous. If the detectable ELISA reaction products from the two ELISA reactions have the same net charge, then it will be important that the detectable components in the two products be distinguishable. For example, the products should have different values of $\lambda_{max}$ for UV-Vis detection, different emission maxima for fluorescence detection, etc.—and ideally, the more different the spectral features, the better. In such applications, detection by surface enhanced Raman scattering (SERS) may be particularly advantageous, since Raman spectra are characterized by numerous narrow bands of varying intensities that provide many opportunities for distinguishing between compounds. In other embodiments, the detectable ELISA reaction products may have the same sign of charge, but the magnitude of that charge might allow for selective separation; this general strategy for separation (though in the context of substrate from ELISA product) is discussed more fully in the next example. One embodiment that is attractive when two analytes are to be measured is one in which the substrates for both ELISA reaction are overall neutral, and in which one of the ELISA reactions produces a net negatively charged ELISA product, while the product from the other ELISA reaction is net positively charged. In such applications it will be advantageous to include a second trapping channel with a semi-permeable membrane, along with an electrode having an opposite potential from the first. In this embodiment, the two ELISA products will be actively separated from one another (and concentrated in their respective trapping channels) by electrical forces, while the neutral unreacted substrates from the two reactions is carried along with bulk solvent to waste. In this embodiment, it is not necessary that there be any spectral difference at all between the two detectable ELISA reaction products, since they will be separated from each other on the basis of the ELISA reactions that led to them.

An extension of the above embodiment of measuring two analytes simultaneously is to measure more than two, most likely two to six analytes. In this case, a combination of the three strategies could be employed. In effect, this process would be similar to current ELISA methodology in which more than one analyte is measured, but the process is made considerably more practical in the methods described herein by the fact that many more enzymes are feasible, and because the possibility of separating compounds on the base of charges greater than zero from those with charges less than zero will halve the complexity of the problem of finding detectable components that can be distinguished from one another. That is, if two dyes can be distinguished, four analytes can likely be measured in a single device, since one can construct substrates with the two dyes for two different enzyme catalyzed reactions that produce positively charged products (directed/concentrated at an anode) and use the same two dyes with two further substrate types that are converted by yet another two enzymes to two negatively charged products (directed/ concentrated at a cathode).

A further method for accomplishing the detection of multiple analytes is accomplished by having two (or more) ELISA regions that feed into the same downstream channel, J. This embodiment provides for the possibility of making use of multiple ELISA reactions having strongly differing pH requirements, for example alkaline phosphatase (preferred pH of ~9.5) and horseradish peroxidase (preferred pH of 5-6). The concentration of the buffers in the two reactions may be adjusted in terms of their concentrations such that they combine to provide a medium that is compatible with the charge states desired for the detectable ELISA reaction products from each reaction, or the combined stream may be further modified by introduction of a pH changing agent through auxiliary channel K, as disclosed in the next example.

EXAMPLE 3

Methods for Enhancing ELISA Detection of Analytes

Throughout this example, and in the ELISA literature in general, reference is made to detecting and quantifying analytes of interest in biological and other systems. However, it should be stressed that while the presence and/or concentration of an analyte is what is ultimately of interest in the assays described here (and elsewhere), this is not what is being detected or quantified. Instead, the presence and/or concentration of enzyme conjugates is being inferred on the basis of the quantity of a detectable enzyme reaction product that is formed in a given time period. The amount of enzyme conjugate present—whether directly or explicitly calculated or not—is then used to infer the presence of an analyte, since the assays of certain embodiments (and all other ELISA methods) are designed so there a predictable correlation between the amount of enzyme conjugate and analyte. For the sake of convenience, and in order to phrase matters in a fashion that is commonly used by those familiar with the art, the methods and practices of the embodiments described herein are largely be described in terms of analyte detection and quantitation, but it should be understood that these are obtained by inferences based on enzyme concentrations, which in turn are determined by the rate of a catalyzed reaction.

The present example combines several different elements that, in particular combinations, provide methods for determining the concentration of analytes with levels of sensitivity and speed that are far superior to existing methodology. The methods of this example are strongly based on the ELISA method, but expand its scope to new enzymes and substrates. Of even greater importance, the methods and practice of the present example provide methods by which the sensitivity and speed of both existing and the newly described ELISA methods can be improved by orders of magnitude. These improvements are sufficiently profound that they will allow measurements to be made in research that currently are not possible, and furthermore will greatly expand the ease with which clinical diagnostics can be carried out.

One embodiment combines three main elements: a microfluidic ELISA platform, a method for rapidly and effectively separating (in a continuous fashion, and furthermore without the use of chromatographic media) the ELISA substrate from the detectable ELISA reaction product, and a method for concentrating that detectable product such that it is more readily detected. However, the means by which both the substrate/product separation occurs, as well as how the product concentration occurs are, in fact, closely related to a requirement for the enzyme catalyzed reaction in the ELISA component of the assay: that the ELISA substrate and the ELISA product have different net charges. In fact, this turns out to provide another non-obvious element, which is that if an enzyme substrate and the corresponding ELISA product can be readily separated on a continuous basis by electrical forces, this ultimately results in an expansion of the number of enzymes and enzyme reactions suitable for use in ELISA reactions, instead of restricting them. The scope and utility of these embodiments can be most fully understood by a consideration of the different elements that make it up, as detailed below.

The Microfluidic Chip. The use of micro-/nanofluidic devices provides an opportunity to realize very large increases in both the speed and sensitivity of the ELISA methods described herein. A micro-/nano-fluidic device typically comprises of a network of micro-/nanometer scale channels (micro-/nano-channels) connecting different circular wells created on a glass, silicon or a plastic (e.g., PMMA, PDMS, polycarbonate) plate. Chemical and biological analyses may be performed on this platform by moving fluid and analyte samples through the closed conduits, while the circular wells act as control ports for guiding this transport process. This above described design for micro-/nanofluidic systems offers a unique set of advantages over conventional instrumentation. The smaller size of these units, for example, reduces the reagent costs and allows their easier automation. It also permits precise dynamic temperature control of these systems due to their smaller thermal mass. In addition, their architecture allows easier integration of multiple operations, e.g., sample preparation, derivatization, sample pre-concentration, separation, all on a single device that further simplifies the analytical procedures. Moreover, such integration minimizes the number of manual sample handling steps, improving the accuracy and the reproducibility of assays, while at the same time reducing operator exposure to potential biohazardous waste. And, because these devices can be manufactured using inexpensive methods, it permits their customization for a specific biological assay in a time and cost effective way.

The above described virtues of microfluidic devices apply to a wide range of chemical and biological analyses. There is at least one further general advantage that certain microfluidic ELISA devices may have over microwell and other format ELISA systems: decreased background associated with non-catalyzed reactions. In ultra-trace analyses performed in microwell platforms a serious concern is that substrate to detectable product conversion may occur adventitiously by non-enzyme catalyzed reactions. Of course, product formed in this way is indistinguishable from product formed in the enzyme catalyzed reaction, and will lead to misleadingly high estimates of the amount of analyte present. Such difficulties arise in the very circumstances they are least desired: when extremely small amounts of analytes are present, when very long reaction times are necessary to generate detectable signal. The microfluidic detection methods of the types described in embodiments operate as flow systems; substrate is introduced and then rapidly leaves the system through a waste channel, while the detectable ELISA product is separated and concentrated. This mode of operation means that the substrate(s) of the reaction can be kept in a state in which no non-catalyzed conversion to product will occur (e.g., at a different pH than will be used in the enzyme reaction, or at a much lower temperature, or isolated from co-reactants), and only supplied/combined just prior to entering the ELISA region of the device. The result is an inherent advantage of microfluidic devices of the type described here over most current ELISA methods, especially in the case of ultra-trace analyses.

The described micro-/nano-fluidic devices can be fabricated using standard micro/nano-fabrication techniques or other methods known to those skilled in the art. Briefly, the fabrication process begins by first defining an interconnected network of micro-/nano-channels onto a plate using standard photolithographic techniques. The substrate is then subjected to a wet or a dry etching procedure to realize the actual conduits or the master pattern that is be later used to create the analysis channels, for example via stamping. Following this, holes aligned with the microstructures on the device are drilled to allow access to the conduits before sealing them off using a cover plate. It is possible to practice the embodiments in conduits with hydraulic diameters ranging from 1 centimeter (cm) to 10 nanometers (nm). The term "hydraulic diameter", as used herein, is being used in a broad fashion, and should be understood to include conduits/channels having some combination of this width range with some combination of depth that may or may not be same. Note that while working with analysis columns larger than a centimeter in diameter may allow greater detection sensitivity as a result of the longer optical path length in the system, the requirement of larger sample volumes as well as the slowing down of reaction kinetics due to diffusion limitations may make it unattractive to work under these conditions. Moreover, the large amount of electrical power necessary to actuate such macro-scale units may cause a variety of problems, including Joule heating, which in addition to affecting the reaction kinetics and the fluorescence characteristics of the chemical species involved in the assay, can introduce spatial variations in the temperature of the analysis column. Further, large power levels may lead to accelerated breakdown of the membranes used in these devices. Any such variation at this length scale has the tendency to generate gravity induced flow circulations which in turn can significantly deteriorate the concentration of the reporter molecules at the membrane interface. Finally, the integration of the ELISA method to the concentration sub-unit (the trapping region) is likely to become increasingly challenging as the size of these devices is scaled-up, adversely affecting the portability of the system. With analysis columns smaller than 10 nm, on the other hand, it is the limited ability to control the channel features, as well as the fluid/analyte transport within them that is likely to make reproducible assays more difficult to accomplish. Such limitations are also likely to pose problems in the fabrication of the membrane, as well as the creation of the ELISA region. Moreover, the lower detection sensitivity at this length scale coupled with greater non-specific adsorption of the chemical species to the channel surface (due to a larger surface area to volume ratio) may overcome benefits obtained through the concentration process itself. It is important to point out that although it may be possible to practice the methods described herein in channels with hydraulic diameters between 1 cm and 10 nm, 1 mm-100 nm are a useful range for this geometric parameter, where a reasonable trade-off is expected to be arrived at between the advantages and disadvantages of device scale-up versus miniaturization.

A component of the microfluidic device to be used in embodiments is an integrated electrically conducting semipermeable membrane that traps the reporter molecules at its interface. Broadly speaking, the membrane structure for a region of the micro-/nanofluidic network is selected using two different strategies. In the first strategy, one selectively retains precursor material in a region of the microchip device and then provides to it a suitable physical/chemical treatment to transform it into a membrane structure. In the second broad strategy, one fills up the entire channel network with a membrane precursor material and then provides the desired physical/chemical treatment only to a chosen region of the device. The former strategy can be implemented, for example, by creating a shallow channel segment in the region where the membrane is to be fabricated. This is optionally followed by filling up the entire micro-/nano-fluidic network (including the shallower region) with the precursor material. Upon application of a pressure drop across these conduits the precursor material are then driven-off the deeper channels. If the pressure-drop used in this process is carefully chosen, the precursor solution within the shallower region will not escape due to the larger capillary forces, allowing its selective retention in the region where the membrane is to be fabricated. Finally, this material is provided a suitable physical/chemical treatment to transform it into a nanoporous network. Implementation of the second strategy utilizes selectively exposing a chosen region of the microfluidic network (that is entirely filled with the precursor material) to the desired physical/chemical treatment. This is optionally accomplished either by using a mask or a focused source of energy (e.g., a LASER beam) that selectively transforms the precursor material into the membrane structure only in the chosen region of the device. An example of this second strategy is the formation of polymeric membranes through photo-initiated polymerization. For example, such a membrane can be fabricated by filling up an entire microfluidic network with 22% (15.7:1) acrylamide/bisacrylamide containing 0.2% (w/v) VA-086 (Wako Chemicals, Richmond, Va., USA) photo-initiator. A chosen region of this network can then be exposed to 355 nm LASER radiation for 15 seconds to polymerize the precursor solution in it. Following this, the unpolymerized solution in the remaining channel segments can be purged by applying a mild pressure drop across the fluidic network. Such polymer membranes may be homopolymers, but it may be desirable in some instances to combine a mixture of monomers for the polymerization reaction to provide a polymer membrane having some combination of desirable features.

A wide variety of precursor materials may be used in the membrane fabrication processes described above, ranging from inorganic siliceous chemicals to organic polymeric solutions. However, because silicate based membranes are known to have a molecular weight cut-off down to 100 Daltons (e.g., a silica-zirconia membrane), they are preferred for certain embodiments over polymeric membranes which usually have a molecular weight cut-off of about a few kiloDaltons (e.g., polyacrylamide based membranes). For example, in one embodiment a precursor solution containing 13.5% $SiO2$ and 5% $Na_2O$ in water selectively retained in a shallow channel segment was treated at 110° C. in a conventional oven at atmospheric pressure for 15 minutes to realize silicate based semipermeable membrane. This structure was observed to completely trap resorufin anions (molecular weight 212 Daltons) at its interface upon application of a suitable voltage drop at electrode D in FIG. 1. On the other hand, polyacrylamide membranes fabricated in microchannels using the procedure described in the previous paragraph have been reported to have a molecular weight cut-off of 6 kiloDaltons.

Optionally, membranes are constructed in what may be considered a hybrid strategy of the general two approaches described above. Formation of membranes according the first of the two strategies described above typically gives a molecular weight cut-off that will commonly be desirable for certain embodiments, but may for example require a higher level of technical skill to produce. On the other hand, the process by which the polymer membranes of the second strategy are formed is more readily carried out, but gives a molecular weight cut-off that will less commonly be desirable. Thus, an embodiment utilizes membranes that combine the ease of synthesis of polymer membranes with the desirable molecular weight cut-off characteristics of inorganic membranes. Formation of these hybrid membranes is accomplished, for example, by simply flowing silica particles that are substantially smaller than the dimensions of the channel towards a polymer membrane that has been formed as described above. More commonly, it is preferable to make a polymer or copolymer that includes chemical groups (silanols or trialkoxysilanes) known to have a high affinity for silicates, and then providing a source of silicate (e.g., sodium silicate solution) or extremely small silicate particles, whereby silicate structures may span the spaces between the groups having high affinity for silicates. In effect, this process comprises establishing a porous polymer network having silicate anchor points, and then filling in the pores in an effectively irreversible fashion with silicates. Introduction of the groups having high affinity for silicates may occur either at the stage of monomers (e.g., by inclusion of triethoxysilylpropyl methacrylate monomer with acrylamide, a cross linker and initiator), or by modifying a polymer or copolymer after it is formed (e.g., by reacting a poly(acrylamide-co-maleic anhydride or poly(acrylamide-co-maleimide) polymer in a microchannel with aminopropyl triethoxysilane, and optionally heating).

It is important to point out that the embodiments described herein are optionally practiced by trapping reporter molecules (detectable ELISA products) within a membrane rather than at its interface with the free solution as described above. When trapping within a membrane the restrictions regarding molecular weight cut-off will become less stringent, because trapping will result from chemical/physical interactions between the detectable ELISA reaction products and the membrane structure. The use of larger pore sizes in the within-membrane trapping strategy will also allow the application of lower electrical voltages in the trapping process, thereby reducing Joule heating in the system. Moreover, this approach is realized by somewhat less stringent membrane fabrication conditions, in addition to having a greater choice for the membrane precursor material. However, this strategy for trapping/concentration may lead to a less sensitive detection due to a shorter optical path length, greater background noise and smaller trapping efficiency for the reporter molecules. In a further variant of this within-membrane trapping, it is optional to include functional groups within the membrane that can react with appropriate functional groups on the detectable ELISA reaction product. For example, the membrane may include thiol or disulfide groups capable of chemically reacting with a thiol or disulfide group of the detectable ELISA reaction product, thereby providing covalent attachment of the reaction product to the membrane. This may provide much greater trapping efficiencies, as well as a more narrowly defined trapping range within the membrane. Other examples of "paired" functional groups on the polymer and ELISA reaction product may be thiol and maleimide, or amine and N-hyroxysuccinimidoyl ester. A conceptually and practically simpler mode of trapping detectable ELISA reaction products is the use of ion exchange elements. For example, a membrane produced by co-polymerization of polyacrylamide and maleic (or fumaric) acid can be produced, followed by treatment with heat or chemical dehydrating agent (e.g., acetic anhydride) to produce a membrane having chemically reactive anhydride groups. Such a membrane can then be reacted with a moiety comprising a reactive primary or secondary amine and a charged group, to provide an ion exchange membrane. For example, reaction with 3-trimethylammonium-1-propane amine (produced by reacting commercially available N,N-dimethylamino-1,3-propanediamine with di-tert-butyldicarbonate, then quaternizing with iodomethane, then removal of the BOC protecting group by stirring overnight with formic acid and removal of solvent and basifying) provides an anion exchange membrane that will show some degree of selective binding of anionic detectable ELISA reaction products. Alternatively, reaction of the anhydride membrane with commercially available 3-aminopropanesulfonic acid/iPr$_2$NEt will provide a strong cation exchanger that will show some degree of selective binding of cationic detectable ELISA reaction products. Obviously, the other affinity elements mentioned above could be incorporated by a similar strategy.

Although the use of an electrically conducting membrane as proposed herein may be one preferred approach for enriching the reporter molecules, it is important to note that such trapping is optionally accomplished in free solution using a combination of hydrodynamic, electrical and magnetic forces. Moreover, it is also possible to employ a metal electrode (micro-patterned or free-standing) for accomplishing the trapping process provided one is able to circumvent any issues arising from the electrochemical reactions occurring at its surface, e.g., bubble generation, pH drifts, unwanted reduction or oxidation of the chemical species involved in the assay, etc. Finally, it may not be necessary to implement embodiments in a flow-through system as described in FIG. 3A. Stationary chambers (e.g., micro-well arrays) with integrated membranes or electrodes can also be used in practicing particular embodiments, although such designs may have a larger limit of detection due to the greater background noise arising from the unwanted non-enzymatic conversion of the substrate to the detectable reaction product (reporter) in the solution phase.

Further, for a flow-through ELISA system with an integrated membrane (as shown in FIG. 3A), it is possible that the concentrated zone of reaction product at or near the membrane interface reaches a steady state after a certain period of operation. For example, a balance will ultimately be established between the number of reporter molecules that are drawn in towards the membrane by the electrokinetic force field and the number of reporter molecules that diffuse out of the concentrated zone and are carried away by the flowing buffer stream. In this situation, it is desirable to have the time scale (T) for approaching such a steady state to be several times larger than the assay time itself. While this may be accomplished by strengthening the electrokientic force field used to trap the reaction product and/or weakening the fluid flow in the system, device architectures that have a large value of T for a chosen magnitude of the electric field and fluid flow velocity will typically offer the most benefit. One simple way to realize such device architectures is to create a no-flow, or stagnant region (that is, the region in the microfluidic trapping channel B that is between the main microfluidic channel and the semi-permeable membrane C) around the membrane interface that can significantly increase the number of trappable reporter molecules before a steady state is reached, which in turn can enhance the sensitivity of the ELISA device embodiments. Although it may be possible to trap more reporter molecules at the membrane interface using designs that have larger stagnant regions, a benefit from this aspect of the design is optionally realized only when the dimensions of this region are comparable to the size of the membrane. For example, there may be practical difficulties in operating devices with large stagnant regions. For example, such designs will inherently lead to the creation of air pockets in such no-flow zones when the fluidic network is initially filled with a liquid. Although such air pockets can be driven out of the stagnant region using electrical forces, this aspect can make the operation of the ELISA device embodiments somewhat inconvenient. Moreover, the quality of any surface coating, e.g., for minimizing non-specific adsorption, is likely to be inferior around these no-flow zones due to limited fluidic access to these areas.

The trapping efficiency of embodiments described herein are optionally enhanced by introducing a flow stream that will focus the reporter molecules closer to the concentration region. In the case of the embodiment shown in FIG. 3A, for example, this may be accomplished by flowing in a stream from segment K. Moreover, the magnitude of this flow relative to that in the ELISA region (e.g., in segment A of FIG. 3A) will have an optimum value for a chosen electric field around the membrane interface. This optimum flow rate will be a result of the reduced distance the reporter molecules will need to travel in the flow zone before they enter the concentration region counteracted by the increased flow speed around the membrane interface. It may also be that the use of a more electrically conducting solution (relative to the ELISA buffer) may be advantageous in creating this focusing stream, since such solutions may further enhance the electric field around the membrane interface, which in turn will increase the trapping efficiency of the reporter molecules for a given applied voltage at electrode D.

The location of the detection zone in the system will be dependent on the method of detection chosen. The optimum location for this zone will certainly lie in the concentration region near the membrane surface, but in most cases will not be right at the membrane interface. This is because most membrane structures tend to generate a greater background noise than an open fluidic conduit. At the same time, having the detection zone far away from the membrane interface will also be less desirable, as the concentration of the reporter molecules will diminish sharply as the distance from this interface increases. In most situations, the best sensitivity for detection of the concentrated ELISA reaction product using particular embodiments will typically be attained by having the detection zone located away from the membrane interface at about a distance equal to its own size, e.g., by a distance roughly equal to the diameter of the light beam incident on the analyte molecules in the case of fluorescence. Finally, it will be desirable to use an electrode material in both electrodes D and G in the above described assembly that do not interact with the chemical species involved in the assay or take part in chemical reactions with the buffer solution, potentially affecting its pH and ionic strength. Of specific note in this regard is avoidance of the possibility that products of such chemical reactions at electrode G might migrate back through the channel due to electrokinetic forces. Although expensive, some of the best candidates for this purpose are platinum and gold, which are known to be inert in most immunoassay based applications.

In the present description, it is generally desirable to suppress electroosmotic flow (EOF) in the region where an electric-field is applied to accomplish the concentrating process. If this is not done, or if it is ineffectively done, a differential in the fluid flow rate at the membrane interface will automatically result, as most membranes have a tendency to block any EOF generated in the fluidic conduit. The net result is a generation of pressure-driven backflow to maintain a flow balance in the system, which in turn will disperse the reporter molecules in the concentration/trapping zone, leading to significant deterioration in the sensitivity of the method. The suppression of EOF around the concentration region can be accomplished for certain embodiments by coating the channel surface around it with a variety of chemical species that can neutralize the charged groups residing on the channel surface and/or increase the effective fluid viscosity in the electrical double layer around the channel walls. Examples of such species include poly(acrylamide), poly(vinyl alcohol), polysaccharides, etc. Such coatings may also comprise monomeric species capable of binding to the surface of the channel that provide a polar, yet uncharged surface. In the case of silicate based channels, these coatings may be established by exposure of the channel to solutions of compounds that incorporate di- or trialkoxysilane groups in addition to polar subgroups, such as N-(3-trialkoxysilylpropyl)formamide, N-(3-trialkoxysilylpropyl)acetamide, as well as polyethylene glycol groups.

The movement of reagents in the ELISA region of the above described devices can be most easily controlled using pressure-gradients, e.g., created through the use of syringe pumps, hydrostatic effects, etc. However, in conduits smaller that a micrometer it may be preferable to make use of other methods for generating flow. This is because the precise control of pressure-driven flows in sub-micrometer scale can be especially challenging and is poorly suited to automation. Control of flows using electrokinetic methods in these situations is often more preferable; flow rates can be modified by simple increases or decreases in voltage, can be reversed (if desirable) by reversing the potential, and are much better suited for automation in laboratories in which large number of ELISA determinations are carried out. In addition, when embodiments are implemented on a nanofluidic scale (e.g., implemented in channels smaller than a micrometer), control of flows by electrokinetic means may be considered nearly essential. Implementation of embodiments at the nanofluidic scale can be quite valuable for basic researchers interested in the ultra-low sample volumes that are encountered in single cell analyses. When an ultra-small sample is introduced into a microfluidic device it is inevitably subject to much greater dilution than would be the case in a nanofluidic device; there is simply more liquid in the former. This is not a good start to a trace analysis. For example, it might be the equivalent of taking a 1 pM sample of metabolite and then diluting it to 10 fM prior to analysis—certainly a counter-productive exercise. Particularly attractive applications of nanofluidic embodiments include "plugging" an inlet channel with a cell, and monitoring compounds released from it, or placing a cell in a channel and lysing it.

In implementing embodiments that make use of electrokinetic effects for controlling flows, one must carefully consider the nature of the substrates and detectable ELISA reaction products. Only compounds that carry a net electrical charge are subject to transport by electrokinetic means. This does not represent an especially stringent limitation to the present method. The antibodies and reporter antibody-enzyme conjugates naturally have some charge, and this charge can often be changed appropriately through variations in pH;

indeed, in "problem" cases molecules of these types could be subjected to conjugation with charge-altering molecules (e.g., poly amines). While charge will limit the scope of the assay to charged analytes it is fortunately the case that many of the biomolecules of interest in assays are naturally charged, so as to impart water solubility. These embodiments will also require that both the enzyme substrate and the detectable ELISA reaction product be charged—or capable of having a charge induced in them—but as discussed below, this feature is desirable even in methods involving pressure driven flows, and so appropriate substrates are already available for some enyzme/reaction types.

It is possible to use the same chip format described in FIG. 3A to arrive at an ELISA method that relies solely on electrokinetic transport. It should be mentioned that, in the context of scaling down device size, it is actually easier to make membranes in smaller channels using the strategy in which the precursor material is selectively retained in chosen region of the fluidic network via capillary forces. Thus, nanofluidic embodiments may enjoy advantages over microfluidic scale embodiments not only with respect to do the analytical targets, but with respect to fabrication. Much of the operation of an electrokinetically-driven ELISA device will be similar to that described in FIG. 3A. However, the movement of the species of interest in the actual assay will proceed quite differently in a number of the preferred embodiments. As noted below in the discussion on "Charge States," a particular embodiment involves the use of a substrate and detectable ELISA reaction product that not only differ in charge, but have opposite signs of charge (due to simplifications in separating the two subsequent to the enzyme catalyzed reaction). In the implementation of such substrates in an embodiment that involves electrokinetic driven flows, a cationic substrate will be moved electrokinetically from the reservoir in which G (cathode) resides towards reservoir H (anode). Importantly, there will be an additional cathode at reservoir D. When this substrate is converted by the immobilized enzymes to an anionic product, that anion will reverse its movement in the channel due to its attraction to the cathodes at reservoirs D and G. A buffer stream will again be drawn in through channel segment K to electrokinetically focus the anionic reporter molecules close to the membrane interface.

The ELISA Region. As was noted above, ELISA assays might properly be considered assays for the presence (and concentration) of enzymes that catalyze reactions producing detectable reaction products. Of course, the practical utility and motivation for implementing these methods is to use the presence of the enzyme to infer the presence of an analyte, and this means that one aspect of such assays is establishing some correlation between the enzyme concentration and that of the target analyte. This correlation is most commonly accomplished by conjugating the signal producing enzyme to some species that will bind the target analyte directly, or bind to something that is in turn bound to the analyte (the inclusion of intervening species can be carried on ad naseum). In this context, "conjugation" refers to covalent attachment of a binding group to an enzyme by any of a variety of methods known in the art. The classical implementation of this concept is the conjugation of a signal producing enzyme (henceforth, the ELISA enzyme) to an antibody (such conjugation commonly being accomplished by linking the two with some bifunctional organic molecule). Thus, a common form of ELISA assay involves an analyte specific binding group (often an antibody) attached to a surface that complexes the analyte to provide a binary complex attached to the surface: {surface-binding group}-(analyte). If the analyte has multiple epitopes, then it can then be further bound by the enzyme-antibody conjugate to give a ternary complex, {surface-binding group}-(analyte)-(antibody-enzyme). As described in methods of the present example, this is considered an ELISA surface. The enzyme substrate can then be introduced, and if properly designed, each enzyme reaction turnover will result in a signal producing molecule of product. If care has been taken to remove excess antibody-enzyme (ultimately, the reason for the surface is to provide for this removal, by wash steps) then there will be one enzyme for each target analyte, and the signal produced in the enzyme catalyzed reaction can be used (indirectly in fact, but directly in practical terms, as a result of empirically derived calibration curves) the amount of analyte present.

Instead of the above described ELISA surface {surface-antibody}-(analyte)-{antibody-enzyme}, one may have a different ordering of the components. For example an ELISA surface may be constructed by binding an antigen to a surface, and then contacting it with a sample containing some amount of an antibody of interest (e.g., an antibody to a virus that an individual may be infected with), followed by introduction of an enzyme-antibody conjugate that is known to bind to the antibody of interest, to give the ternary complex {surface-antigen}-(antibody)-{anti-antibody-enzyme}. As before, the rate of detectable ELISA product formation can then be used to infer the presence of the target antibody. Of course, it should be understood that the ELISA enzyme may be conjugated to substances other than antibodies. For example, instead of a specific anti-antibody or species specific anti-antibody, it may be bound to protein A/G, which is known to bind to a variety of antibody classes. In a particularly versatile class of ELISA methods the ELISA enzyme is conjugated to streptavidin, providing a composition that will bind to biotinylated compounds. For example, ELISA surfaces comprising quaternary complexes of the form {surface-antibody}-(analyte)-{antibody-biotin}-{streptavidin-enzyme} can be constructed by the methods described above, as can ELISA surfaces of the type {surface-antigen}-(antibody)-{anti-antibody-biotin}-{streptavidin-enzyme}, as well as other complexes. In fact, a particularly simple embodiment comprises the device of FIG. 3A, in which the semipermeable membrane is silica, the regions K, J and F have been coated with the anti-osmotic flow agent N-(3-triethoxysilylpropyl)formamide, the electrode potential at D has been set to positive, and the ELISA surface has been constructed by first establishing a biotinylated surface in region A (by successive coating with aminopropyl triethoxysilane, and then the N-hydroxysuccinimidoyl ester of biotin) and exposing it to a sample containing a horseradisih-streptavidin conjugate, followed by washing, thereby providing a surface made up of some large amount of surface bound biotin, and varying amounts of a biotin-streptavidin-horseradish peroxidase complex (the amount depending on the horseradish-streptavidin concentration in the sample). Introduction of the enzyme substrate Amplex Red® leads to a rapid development of signal in the trapping region that can be detected using a fluorescence microscope. Though select examples of enzyme conjugates and ELISA surfaces have been provided above, there are a multitude of possible conjugates and ELISA surfaces that are known, as well as methods for establishing them, and that these here-undescribed conjugates and surfaces would be equally applicable in embodiments. The methods and practices described herein can also readily be applied to competitive immunoassays.

The Detection Method. Depending on the nature of the detectable component of the detectable ELISA reaction product any of a number of detection methods may be used. The simplest methods may include UV-Vis methods and fluorescent methods, with the latter more often preferred due to its typically greater sensitivity. Though exemplary embodiments will provide inherently high levels of signal due to the rapid concentration of the detectable ELISA reaction product—and do so using relatively inexpensive fluorescence/UV-Vis technologies—there will nevertheless be some instances in which simple fluorescence (or UV-Vis) methods may not prove to be sufficient. In these cases, it may be desirable to employ one of the methods described below.

Compounds currently used in ELISA assays that are detected using time-resolved fluorescence can similarly be detected in embodiments that include instrumentation capable of time-resolved fluorescence measurements, provided of course that the detectable reaction product has a net charge, and ideally a net charge that is different from the ELISA substrate. However, this does not represent a particularly difficult requirement, since charged detectable ELISA reaction products are known, and others can be generated from substrates that have been modified by chemical synthesis so as to be charged after the ELISA reaction.

Another embodiment expected to provide for further increases in signal beyond that accruing from concentration effects is the use of polarization-resolved fluorescence. Polarization resolved fluorescence methods involve detecting only fluorescent molecules that are oriented in some way (e.g., those that may be rotating differently, or at a different rate) than other species in solution. As applied to certain embodiments, the semi-permeable trapping membrane of the detection device can be coated with an oriented layer of organic molecules, and then a substrate used that will produce a detectable ELISA reaction product that comprises both a net charge and a hydrophobic moiety. When transported to the detection channel by virtue of its charge, the hydrophobic portion of the detectable ELISA reaction products will be absorbed into the oriented layer at the semi-permeable membrane, and thereby be ordered themselves, allowing them to be detected preferentially by polarized fluorescence. A variety of organic molecules could be used to establish the oriented layer of organic molecules, one example of which is dodecylsulfate. Thus, prior to introduction of the analyte (and even possibly before establishment of the ELISA region) a solution of dodecyl sulfate can be introduced and attracted towards a cathodic electrode at D, wherein they will be trapped at the semi-permeable membrane surface. An ELISA substrate that will produce an anionic hydrophobic ELISA reaction product would then be employed in the assay.

The oriented organic surface described above may also be employed in other types of assays. For example, Erythrosin B has been used as an extraordinarily sensitive phosphorescent probe for rotational diffusion in membranes due to its high quantum yield for triplet formation. Since an isothiocyanate derivative of Erythrosin B is commercially available, this molecule can be directly and immediately used with the methods described herein by functionalization in the same way as described above for rhodamine isothiocyanate.

Chemiluminescence has been used as a very powerful tool for increasing the sensitivities of ELISA methods, and can be applied in embodiments described herein. Thus, the neutral ester of the isoluminol derivative shown in the reaction below can be used in combination with porcine liver esterase-antibody conjugates to provide a readily separable anionic ELISA product that will be concentrated as illustrated in FIG. 3A using a cathode at D; the neutral ester will be carried along with solvent to waste. After allowing the enzyme reaction/concentration to proceed for an appropriate length of time the substrate solution is replaced by buffer to flush away excess luminol. Finally, a solution of potassium persulfate will be introduced (most advantageously, through the auxiliary microfluidic channel K, so as to preserve the ELISA region if further data needs to be collected). The anionic persulfate is drawn into the concentration/trapping channel B where the anionic ELISA product is, leading to the desired chemiluminescent reaction. This reaction is extraordinarily sensitive, since persulfate oxidation of similar isoluminol derivatives has been shown (Schroeder and Yeager, Analytical Chemistry 1978, 50, 1114) to provide 10 pM sensitivities. The combined enzyme amplification and concentrating effects of certain embodiments are expected to greatly improve on this detection limit. A further virtue of this method is the ease with which the enzyme substrate for the reaction may be prepared, by reaction of the known 4-(4-aminopropylamino)-N-methylphthalimide with succinic anhydride, followed by conversion to the cyclic phthalylhydrazide with hydrazine, and finally Fisher esterification in methanol.

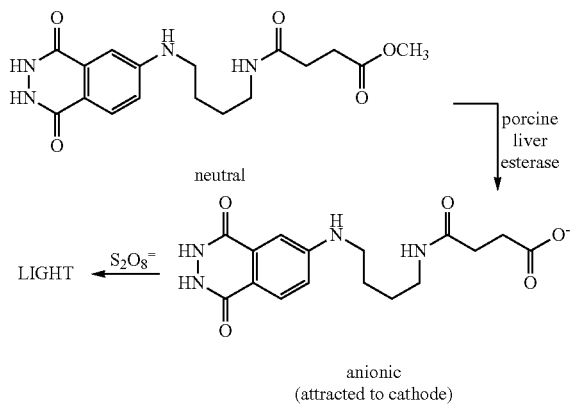

The methods and practices of this example are particularly well suited for the use of surface enhanced Raman scattering (SERS) spectroscopic methods for the detection of ELISA reaction products. The SERS effect provides extremely large enhancements of the Raman signal; when combined with the ability of particular embodiments to selectively direct and concentrate detectable ELISA reaction product at an appropriate surface, this embodiment will provide a three-fold set of amplifications of signal: that resulting from the repeated enzyme reaction, that from the charge/electric field induced concentration of the detectable ELISA reaction product, and that from the signal enhancing effect of the surface for the Raman spectrum. The SERS detection embodiment also provides advantages from the standpoint of analysis of multiple analytes, since the high information content inherent to vibrational spectroscopy allows spectral signatures associated with multiple analytes to be distinguished from one another and separately detected and quantified.

The requisite SERS surface for this embodiment may be formed before or after coating the ELISA region of the detection device. For example, in a device having the configuration described in FIG. 3A in which there is already an ELISA region established having the antibody-analyte-{antibody-enzyme conjugate} coating, one may introduce gold (or silver) colloid through the auxiliary microfluidic channel K, while applying a positive potential at electrode D. Assuming that the colloids used were produced by any of a number of reductive processes (e.g., involving citrate reduction) then the colloid will have a net negative surface charge, and will be attracted towards the microfluidic detection channel, B, where the colloid will be trapped at or near the surface of the semi-permeable membrane, C. After sufficient colloid is at the surface, introduction of the colloid can be stopped, and flow of substrate through the ELISA region initiated. In this example, substrate should be chosen so as to produce a net anionic detectable ELISA reaction product, so that it will be also drawn towards the microfluidic detection channel, B, where it will inevitably encounter the gold (or silver) surface, and will be detected using a Raman microscope or other appropriate Raman device. Many dyes and polar molecules have a reasonably high natural affinity for gold (or silver) colloid surfaces, and it will in most cases be sufficient to rely on this affinity for surface association. However, in some instances, and especially when particularly high detection sensitivities are desired, it may be desirable to include one or more groups as part of the detectable ELISA reaction product that has/have a high affinity for gold (or silver), most especially thiols and disulfides. Of course, many other molecular subunits have strong affinity for gold (or silver) as well (e.g., those incorporating a pyridine ring in some form), and could be used in place of, or in conjunction with a thiol or disulfide.

Figure 4:
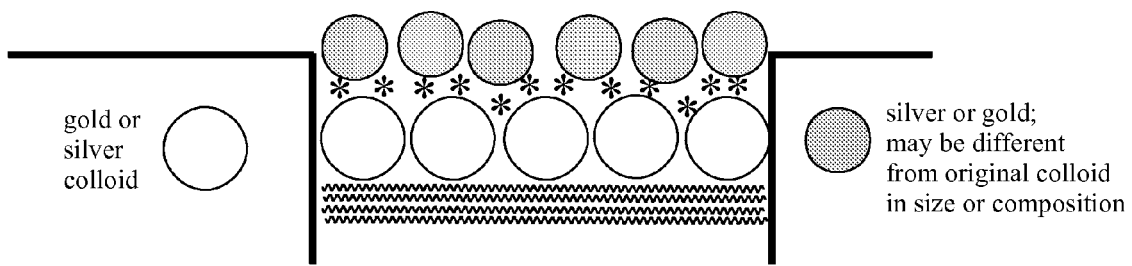
FIG. 4 provides a schematic illustration of a SERS detection embodiment utilizing colloids.

The above-described SERS detection embodiment may be readily modified to provide even greater detection sensitivities in some instances. It is well known to those familiar with SERS that there is a "mirror effect" in which analytes that are localized between gold (or silver) surfaces are subject to an even larger SERS signal enhancement than that found when the analyte is at a single silver (or gold) surface. This further enhancement of signal (and decrease in detection limit) may be exploited in exemplary embodiments by first operating an embodiment in the method described in the preceding paragraph to allow for the adsorption of analyte at the gold (or silver) surface to give a gold(silver)-analyte complex, then stopping the introduction of the substrate (with the optional step of passing non-substrate containing buffer through the ELISA region to remove excess substrate), and introducing additional gold (or silver) colloid through auxiliary microfluidic channel K, whereby the colloid will be deposited on top of the pre-existing gold(silver)-analyte complex, thereby giving a sandwich gold(silver)-analyte-gold(silver) complex that exhibits especially high levels of signal generation. A depiction of this sandwiching effect in the microfluidic detection channel is provided in FIG. 4. Indeed, under some conditions, it may be desirable to simultaneously introduce substrate through the ELISA region, while at the same time introducing colloid through auxiliary microfluidic channel K. Such embodiments will typically not involve ELISA substrates that have a high natural affinity for gold (or silver) colloids, since such substrates would encounter the colloids and bind, thereby providing an undesirable background signal; nevertheless, there may be circumstances under which this is acceptable (e.g., when the substrate produces a very small signal relative to the detectable ELISA reaction product).

There are numerous variations of the above described SERS detection embodiments. These include, but are not limited to variations in which the gold (or silver) colloid surface is established prior to establishment of the ELISA region (e.g., in the form of a device that is suitable for immediate use with a variety of antibodies and analyte targets, as desired by a user), variations in which the colloidal gold (or silver) is affixed to the semi-permeable membrane in some way (e.g., by prior treatment of the membrane surface with mercaptopropyltriethoxysilane, or 3-triethoxysilylpropylsulfonic acid, or similar compounds having affinity for gold/silver at one end and the membrane surface at the other), variations in which the gold (or silver) surface is prepared by means other than directing colloids to the semi-permeable membrane (e.g., chemical or electrochemical deposition).

Though gold and silver will generally preferred for these embodiments, it would also be possible to use copper. And, while there are advantages associated with the use of semi-permeable membranes, it may on occasion be desirable to have the microfluidic trapping channel terminated with a gold, silver or copper electrode instead, where the SERS effect can be taken advantage of at the electrode surface (as it was first observed when the effect was discovered). Other uses than SERS might also be made of the metal surfaces described above, such as detection methods based on surface plasmon resonance (SPR).

Optionally, the ELISA reaction product can be detected by electrochemical means. In some embodiments this will be a direct detection, but it may on occasion be desirable to make use of some cycling reaction to obtain a further amplification of the signal. For example, the sensitivity of this detection method may be increased by reducing/oxidizing a reporter molecule (e.g., a charged derivative of o-phenylenediamine) at one electrode and at the same time oxidizing/reducing the corresponding product (e.g., the corresponding derivative of 2,3-diaminophenazine) at a different electrode. The overall process in this situation had the potential to generate a large signal even with a small amount of the reporter molecule, provided these species can be localized between the two electrodes for a sufficient amount time, that necessary to repeat the redox cycle several times.

Charge States of the Substrate and Detectable ELISA Reaction Product. Another feature that is present in a number of embodiments is that the net charge of the substrate for the catalyzed reaction and the detectable ELISA reaction product be different (or can be made different, as noted below, for example by using post-ELISA pH changes). In exemplary embodiments, it is desirable that the net charge of the detectable ELISA reaction product be non-zero: that is, it is desirable in most cases for the net charge of the detectable ELISA reaction product be greater than zero or less than zero. The extreme desirability of having different net charges for the substrate and detectable ELISA reaction product follows from the fact that these different net charges will allow the two substances to be separated from each other by the use of electric fields. This separation has the effect of increasing the S/N for the detection of the detectable ELISA reaction product by removing background noise associated with the substrate. In those embodiments that do not involve generation of a new dye chromophore (that is, the enzyme catalyzed process does not substantially alter the chromophoric properties of what will be the detectable component of the detectable ELISA reaction product), the difference in net charge between substrate and detectable ELISA reaction product becomes an absolute requirement, and not simply an extremely desirable feature. In those instances in which the enzyme catalyzed reaction produces, or enhances the detectable component of the detectable ELISA reaction product, one may still have embodiments in which both the substrate and the detectable ELISA reaction product have the same (non-zero) net charge, since such embodiments can still take advantage of the concentrating effects afforded by having the combination of detectable ELISA reaction product with a non-zero charge, an appropriate electric field, and a semi-permeable membrane. However, as noted above, such embodiments will generally be less preferable than those in which the substrate and detectable ELISA reaction product have different net charge states, since, with the same net charge, the substrate will also be concentrated along with the detectable ELISA reaction product. Since it will typically be the case that the substrate is present in great excess, this will result in an especially undesirable level of background signal.

The desirability of having a non-zero net charge for the detectable ELISA reaction product follows from the fact that compounds having zero net charge are not readily manipulated (moved in a selective fashion) by electric fields, while those that have a non-zero charge are. As has been disclosed in the previous example, a useful embodiment involves directing the detectable ELISA reaction product to a semipermeable membrane where it will be trapped and concentrated, thereby allowing it to be detected after a lesser period of enzyme catalyzed reaction than would otherwise be required (i.e., than would be required by a method not employing electric fields).

Systems that satisfy the desirability criteria given above—that the substrate and detectable ELISA reaction product have different net charges, and that the charge of detectable ELISA reaction product be non-zero can be summarized as shown in Table 1, in which "S" represents the substrate for the catalyzed reaction, while P* represents the detectable ELISA reaction product, with the asterisk "*" indicating the presence of a detectable component. The letters "n" and "m" are non-zero integers indicating the magnitude of a given charge type in the substrate and product, respectively. Also provided in Table 1 is the nature of the electrode at D (reference FIG. 3A) most appropriate for the reaction type shown. In FIG. 3A this electrode is shown as the cathode, but this was for the sake of illustration for a hypothetical anionic detectable ELISA reaction product: in other applications it will be the anode, with electrode G as the cathode. It should be noted that in Table 1, the charges indicated are net charges. Thus, the designation $^{(1-)}P^*$ could indicate a detectable ELISA reaction product having a single negative charge, but could also indicate a molecule having two negative and one positive charges, or three negative and two positive charges, etc.

TABLE 1

| Entry | Catalyzed Reaction | State of Electrode D in FIG. 1 |
|---|---|---|
| 1 | $^{(n+)}S \rightarrow {}^{(m-)}P^*$ | cathode (+) |
| 2 | $^{(n-)}S \rightarrow {}^{(m+)}P^*$ | anode (−) |
| 3 | $S \rightarrow {}^{(m-)}P^*$ | cathode (+) |
| 4 | $S \rightarrow {}^{(m+)}P^*$ | anode (−) |
| 5 | $^{(n+)}S \rightarrow {}^{(m+)}P^*$ | anode (−)# |
| 6 | $^{(n-)}S \rightarrow {}^{(m-)}P^*$ | cathode (+)# |
| 7 | $^{(n+)}S \rightarrow P^*$ | anode (−) |
| 8 | $^{(n-)}S \rightarrow P^*$ | cathode (−) | additional trapping channel may be required depending on specifics of assay design.

Embodiments employing reactions of the type in entries 1 and 2 of Table 1 will commonly be amongst the most desirable. As noted previously, assay sensitivity can often be increased as much through decreasing background noise as through increasing signal from a detectable species. In exemplary embodiments, the detectable ELISA reaction products are actively drawn by electrical forces into a microfluidic side channel blocked by a semi-permeable membrane, where they are trapped and concentrated. While a neutral substrate (as in entries 3 and 4 of Table 1) is not actively drawn into the side channel (and instead will move with the bulk of the solvent flow), there will inevitably be some contamination of the detection region by components of the solution. This will contribute some noise in the case of ELISA substrates that are transformed in the catalyzed reaction to more detectable ELISA reaction products, but in the case of reactions in which the catalyzed reaction does not change or enhance the signal from the detectable component of the ELISA reaction product, such "noise" would make very large contributions to the signal. In embodiments that employ reactions of the type in entries 1 and 2 of Table 1, substrate will be actively drawn away from the detection zone. This will result in improvements of S/N for all the categories of catalyzed reactions, and will be particularly effective in improving assay accuracy in the case of substrates in which there is no change/enhancement of the chromophore on going from substrate to product.

Reactions of the type illustrated in entries 3 and 4 in Table 1, in which a neutral substrate is transformed into a negatively (or positively) charged detectable ELISA reaction product will be satisfactory for many assays, and may be chosen in some cases, especially if synthesis of the substrates, or versatility in the choice of catalyzed reactions happens to be an attractive feature. As noted above, assays involving neutral substrates may be subject to some level of background noise associated with diffusion of the substrate into the detection zone. However, if the reaction catalyzed is one that involves modification of the chromophore, or an essential bond of the chromophore, such that the substrate is poorly detectable, while the ELISA reaction product is very readily detectable, then the background noise afforded by diffusion of the substrate into the detection zone will be sufficiently small that the assay may have satisfactory accuracy and sensitivity. The problem of passive diffusion of sample into the detection zone can be addressed, in part, by increasing the distance of the semipermeable membrane and detection zone from the main channel of the device, since diffusion over a greater distance will be less pronounced. It may also be possible in some cases to decrease such passive diffusion by use of a microfluidic side channel located on the same side of the main microfluidic channel as the microfluidic trapping region (e.g., opposite to channel K of FIG. 3A). Introduction of buffer through this additional channel will pinch the main flow (having the substrate and product) away from the microfluidic trapping zone; provided a sufficiently high voltage potential, along with an appropriately low flow rate and downstream channel (J) length, it will often be possible to draw the ionic detectable ELISA reaction product through the pinching stream to the trapping region.

In some instances, it may prove to be desirable to choose a reaction of the type depicted in entries 5 and 6 of Table 1, in which a charged substrate is transformed by the catalyst into a detectable ELISA reaction product having the same sign of charge (though differing in magnitude). The charged detectable ELISA reaction product and the charged substrate may still be separable, by relying on appropriately balanced solvent flows, potentials, and the distance between the ELISA region and the microfluidic trapping side channel. Regardless of which of the two species has the greater charge, the greater the magnitude of the charge difference, the more readily this embodiment will be to carry out. In effect, the device will be operated in a fashion similar to a mass spectrometer, with the effect of bulk solvent flow rate being comparable to the effect of kinetic energy in a mass spectrometer. The probability of a molecule being trapped in the detection zone will be increased by a higher charge on the molecule, by a higher voltage potential at electrode D of FIG. 3A, and by a greater distance between the ELISA region and the microfluidic side channel (since there will be more opportunity for movement towards the side channel before the compound is carried out to waste by the passive solvent flow). The probability of trapping a molecule will decrease if its charge is small, if the distance between the ELISA region and the side channel is short, and especially by a high solvent flow. In embodiments of this type in which the detectable ELISA reaction product has a higher charge than the substrate, the design of the detection system can be the same as that shown in FIG. 3A. The distance between the ELISA region and the microfluidic side channel (that is, the length of the downstream channel J) will be made fairly short, the flow rate of solvent will be fairly high, and the potential at electrode D will be relatively low, such conditions being appropriate only for trapping the most readily trapped species (that is, those with higher charges). If, for some reason, there are compelling reasons to carry out the particular embodiments using a reaction of the types shown in entries 5 and 6 of Table 3A in which the charge on the substrate is higher than that on the detectable ELISA reaction product, it will generally be desirable to include an additional microfluidic channel between the trapping side channel and the ELISA region. For example, an electrode having the same potential as D can be placed in auxiliary channel K. In this case, with appropriate solvent flows and potentials, unreacted substrate would be drawn into the auxiliary channel K (due to the greater attractive force exerted on the more highly charged substrate), while the detectable ELISA reaction product would largely overshoot side channel K, to be eventually trapped in the trapping side channel, B, that will be placed sufficiently distant (downstream channel J is long) from the ELISA region and auxiliary channel K to allow the more gradual movement of the lesser charged product to occur.

Entries 7 and 8 of Table 1 illustrate less commonly desirable embodiments, although still useful, in which a charged substrate produces a neutral detectable ELISA reaction product. Though embodiments that use such reactions may in some instances be used, they are generally less attractive, since there is no provision for concentration of the detectable ELISA reaction product; instead, detection can occur as the neutral ELISA product flows past a point (with the signal integrated over time), or the flow collected in some fashion. In the latter instance, it will likely be advantageous to collect the flow in a way that provides for an ever-increasing path length for some optical means of detection, thereby providing increasing sensitivity as the product is collected. The advantage of this embodiment over current ELISA methods lies with the removal of substrate that could cause background noise (that decreases S/N by providing a higher N). For those instances in which an ELISA substrate is employed in which there is a detection-optimized dye present that is not integrally involved in the enzyme catalyzed reaction, this embodiment provides a very substantial improvement over current ELISA methods.

In the discussions above, there has been an implicit assumption that the detectable ELISA reaction product is "automatically" produced in the desired final net charge state. For example, a neutral substrate might produce a negatively charged detectable ELISA reaction product: $S \rightarrow {}^{(-)}P^*$. This is not, however, a requirement of all embodiments. There may be circumstances in which the optimal pH of the enzyme/catalyst catalyzed reaction is not optimal with respect to the spectroscopic characteristics of a given ELISA product, or that in order to make the detectable ELISA reaction product separable from the substrate, some sort of change in the charge states of the detectable ELISA reaction product, or the substrate (or a reaction by-product) needs to be induced by a change in pH. Thus, in the context of the example just given, one might preferentially have $S \rightarrow P^* \rightarrow {}^{(-)}P^*$, or $S \rightarrow P \rightarrow {}^{(-)}P^*$. Accordingly, another embodiment includes the step of changing pH after the enzyme/catalyst catalyzed reaction.

There are examples of pH changes occurring at the end of ELISA assays. These changes are typically made to improve the detection of the detectable component of the detectable ELISA reaction product, as was described for one of the two motivations given in the preceding paragraph. Such pH changes in current ELISA methods, while sometimes necessary, have the undesirable effect of stopping the assay at that point (since the pH change will alter, or even stop, the enzyme catalyzed reaction). This is undesirable because it may be that insufficient signal has developed for an accurate measure of enzyme (and by inference, analyte), and because assays in which signal can be measured repeatedly as a function of time are generally much more reliable and sensitive than single point assays. In the post-ELISA pH change embodiment, there is no necessity to stop the assay; data can be collected on a continuous or semi-continuous basis for as long as the operator desires.

A post-ELISA pH change embodiment makes use of one or more auxiliary microfluidic channels, and will be illustrated using the device of FIG. 3A. Following establishment of an ELISA surface that includes analyte and the corresponding antibody-enzyme complex, enzyme substrate is introduced in a buffer that is optimized with respect to affording maximal enzyme catalysis. At the same time, a solution containing a pH-changing agent is introduced through auxiliary microfluidic channel K. Because mixing at a microfluidic level is often inefficient, it will often be advantageous to employ a charged pH-changing agent that is drawn towards the electrode D. For example, if one wishes to increase pH downstream of the ELISA region in the downstream channel J in an assay involving a cathodic electrode at D, a solution of trisodium phosphate can be introduced through channel K. The highly charged phosphate anions will be move electrophoretically through the main stream of solvent coming from the ELISA region A, thereby changing the pH of the stream. Other anionic bases (e.g., potassium carbonate, sodium borate to name just two) are also useful for this purpose depending on the magnitude of the pH change desired. The magnitude of the pH change induced will be influenced by the pH and concentration of the buffer solution used in the enzyme catalyzed reaction, as well as by the concentration of the pH-changing agent, and the basicity of this agent. For example, with electrode D as the cathode, the following compounds will all be drawn electrophoretically across the stream emerging from the ELISA region and thus be will mixed with that stream, and represent a series of compounds having increasing potency in changing pH: sodium dihydrogen phosphate, sodium acetate, disodium hydrogen phosphate, trisodium phosphate, sodium hydroxide. Similarly, the pH can be made more acidic in the post-ELISA region. Once again, especially effective mixing will be achieved by use of a charged pH-changing reagent that is drawn electrophoretically across the stream of solvent exiting the ELISA region, and in many cases such reagents would be drawn towards an anode. An example of a series of compounds having increasing acid strength that can be electrophoretically directed towards an anode is: trimethylammonium bromide, pyridinium chloride, trimethylglycine hydroiodide. Of course, by appending a negatively charged group (e.g., sulfate, sulfonate, phosphate, phosphonate, carboxylate) to an acid, it is possible to draw the acid to a cathode (e.g., the monosodium salt of sulfoacetic acid), and similarly, appending a positively charged group to a base (e.g., trialkylammonium) it is possible to draw the base to an anode (e.g., 4-trimethylammonium1-dimethylaminobutane).

As noted above, there are two circumstances in which a post-ELISA pH change are likely to be most commonly desired: a change in pH to improve the detectability of an ELISA product, and a change in pH to make the separation of the enzyme substrate and ELISA reaction product possible. A simple example of the first case is exemplified by a modification of a particular embodiment, in which the substrate Amplex Red® is converted to resorufin anion by horseradish peroxidase. Horseradish peroxidase is known to exhibit a pH rate maximum between pH 5 and 6, yet assays involving Amplex Red® are routinely carried out at pH values closer to pH 7.3. This is because resorufin fluorescence is highly pH dependent (only the anion is strongly fluorescent), and it reaches a maximum at close to pH 8. Thus, the assays in current use represent a compromise in which enzyme activity is sacrificed to some degree in order to (mostly) maximize the signal produced by the ELISA reaction product. Since the enzyme is not operating at its pH rate maximum, this compromise results in fewer turnovers than otherwise would be possible, and thus the sensitivity of the assay will be lower than theoretically possible due to the lower amplification accruing from the ELISA reaction. The pH change embodiment allows the maximum theoretically possible sensitivity to be achieved, while still allowing for a continuous measurement of signal to be made. Thus, the conditions for the example given previously, in which the concentration of mouse anti-BSA is measured, can be modified as follows while still using the same device depicted in FIG. 3A. Instead of supplying the substrate for the ELISA reaction in a pH 7.5 buffer (as described previously), it is supplied in a pH 5.5 buffer, essentially at the pH maximum for horseradish peroxidase. Though at least some of the resorufin produced under these conditions will be anionic, the bulk will be present in the neutral, poorly fluorescent form (see the below scheme). Concurrent with the flow of buffer/Amplex Red®, a sodium borate buffer at pH 9 is introduced through auxiliary channel K. This buffer is drawn across the stream of reaction buffer exiting the ELISA region, thereby raising its pH so that essentially complete conversion of the resorufin to its highly detectable anionic form is achieved, and it is subsequently trapped, concentrated, and detected as described previously. In the example given previously for the detection of mouse anti-BSA, operating the assay system with a pH of 7.4 for the enzyme reaction and a pinching flow of pH7.4 buffer from reservoir K provided a >10-fold increase in signal production over the static ELISA measured in the ELISA region A in the absence of an electric field. When the electric field was combined with introduction of a high pH borate buffer (pH 9.2), the increase in signal production was >3000× that of the static ELISA. This extraordinarily large signal enhancement likely derives from a combination of fluorescence enhancement and an increase in trapping efficiency, both of which are associated with the complete formation of the electrophoretically- and fluorescently-active anion of resorufin.

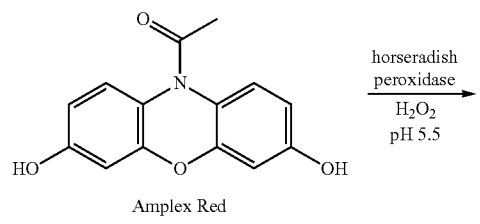

Amplex Red

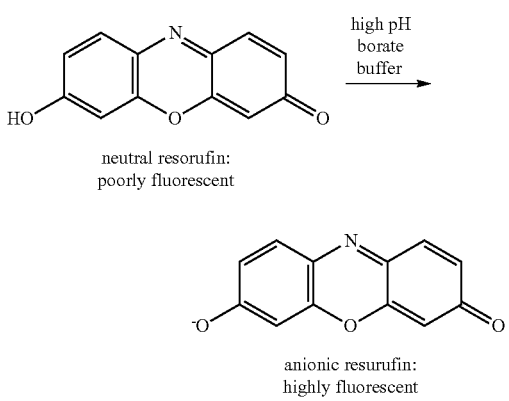

neutral resorufin: poorly fluorescent anionic resurufin: highly fluorescent

An example of a pH-change embodiment in which a pH change is employed to allow separation and concentration of the detectable ELISA reaction product is shown in the below scheme. The substrate for this reaction is attractive for a number of reasons. The detectable chromophore comprises a derivative of methylene blue, having excitation and emission maxima in the 650-700 nm range. It is also readily synthesized from commercially available starting materials (by reaction in DMF of Azure B with the tert-butyldimethylsilyl ether of 3-bromomethylphenol, followed by deprotection and phosphorylation). Use of this substrate in assays in which alkaline phosphatase is employed at its pH rate maximum (about pH 9.5) produces a mixture of unreacted substrate and a phenolate ELISA product. This ELISA product has a net charge of zero, and is thus not subject to the electrokinetic manipulation and concentration that is at the heart of many embodiments. However, when a concentrated solution of imidiazolium hydrochloride is provided through auxiliary channel K it will be drawn towards an anodic electrode at D, thereby causing it to cross the stream of substrate and ELISA product emerging from the ELISA region and effecting a change in the pH.

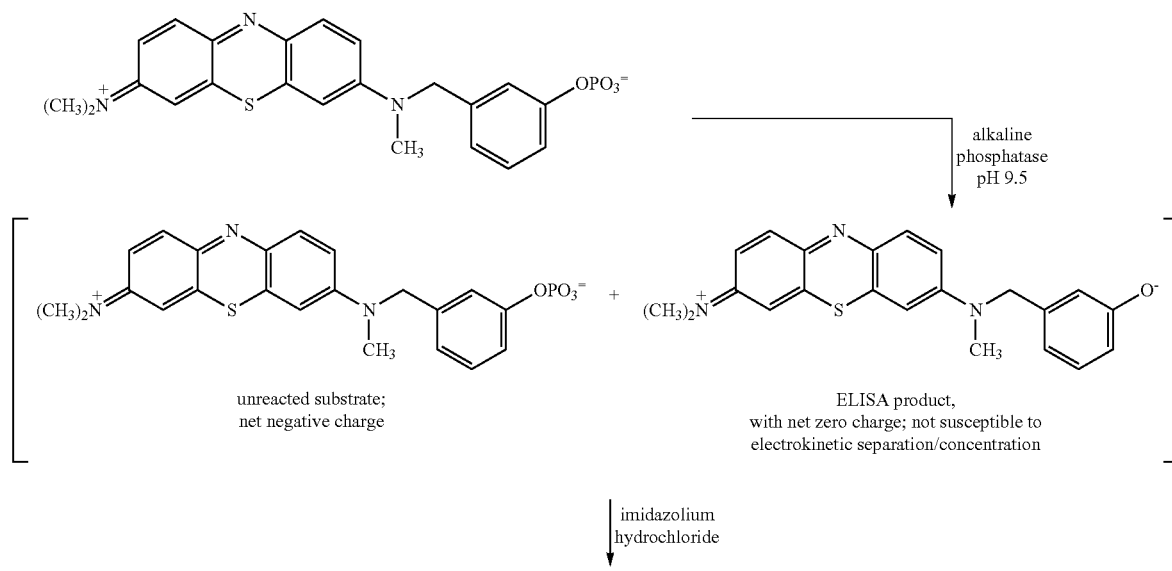

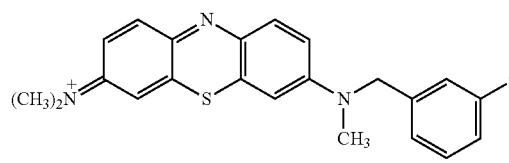

unreacted substrate;
with net zero charge; not susceptible to
electrokinetic separation/concentration

+

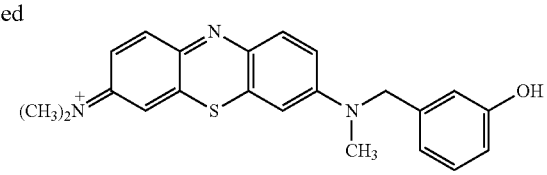

ELISA product,
with net poisitive charge; electrokinetically
directed/concentrated to anode → anode The pKa of imidazolium (about 7) is such that it is sufficiently acidic to convert the phenolate of the ELISA product to the neutral phenol (leaving behind the net positive charge of the thiazolium ring) and the phosphate dianion to the phosphate monoanion. However, imidazolium is not so acidic that it will further convert the phosphate of the substrate to an uncharged phosphate group. The overall result of this process is to convert a mixture that comprises a mixture of substrate and product that are in a very undesirable set of charge states into a mixture in which the substrate will be unaffected by electrokinetic forces, while the ELISA product is readily separated from it, and at the same time is concentrated.

In the examples above, the auxiliary channel K is used to introduce acid or base so as to modify the spectral, or charge characteristics of the compounds leaving the ELISA region. The auxiliary channel K is also useful for introducing a post-ELISA region derivatizing agent, provided of course that the ELISA reaction has produced a product that has a sufficiently different reactivity from the starting substrate.

The Enzyme and Reaction Catalyzed in the ELISA Reaction. The change in charge state on going from substrate to detectable ELISA reaction product is integrally tied to the catalysts, and corresponding reactions, involved in this process. It should be noted at this juncture that, while in the discussions above and those that follow, the term "enzyme" is used (as well, by implication, in the term ELISA), it is not necessarily a naturally occurring protein catalyst (and enzyme) that is necessary for the operation of certain embodiments; other catalysts may be equally effective, since what is of importance is that there is signal amplification in a process in which a single catalyst (e.g., enzyme) can process many substrates to detectable products, thereby giving signal amplification. However, while it should be clear that any appropriate catalyst can serve this role, for the sake of simplicity in describing the present embodiments the term "enzyme" (and its variants) is intended to cover all appropriate catalysts.

As discussed above, most current ELISA methods make use of just a few enzymes, and even fewer reaction types in their signal amplifying reactions: oxidation reactions (almost always catalyzed by horseradish peroxidase) that convert a non-dye to a dye, and hydrolytic bond cleavage reactions that involve an atom (generally an oxygen) that is an integral part of the detectable chromophore. The latter reactions rely on some dramatic change in chromophoric properties associated with the C—O-dye bond cleaving reaction, that are generally afforded by the conversion of the neutral oxygen to a much more strongly donating anion, dye-O—. Embodiments may also take advantage of many of these common currently used ELISA reactions/substrates, but as should have become clear, the suitability of the reactions will vary since embodiments described here differ from current ELISA methodology in their dependence on the change in charge state upon going from substrate to detectable ELISA reaction product—a change that does not necessarily have any influence on the dye chromophore (though this may be a side benefit). Some currently employed reactions that can illustrate the varying degree of utility are shown below in Table 2. Not all examples of ELISA reactions producing a charge state change are shown in this Table (e.g., reactions involving conversion of the neutral NADH to cationic NAD$^+$).

TABLE 2

| Entry | Substrate and reaction | Change in charge state |
|---|---|---|
| 1 | 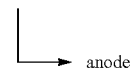 horseradish peroxidase, H$_2$O$_2$ → | −1 (0 → −1) |
| 2 | β-galactosidase → | −1 (0 → −1) |

TABLE 2-continued

| Entry | Substrate and reaction | Change in charge state |
|---|---|---|
| 3 | 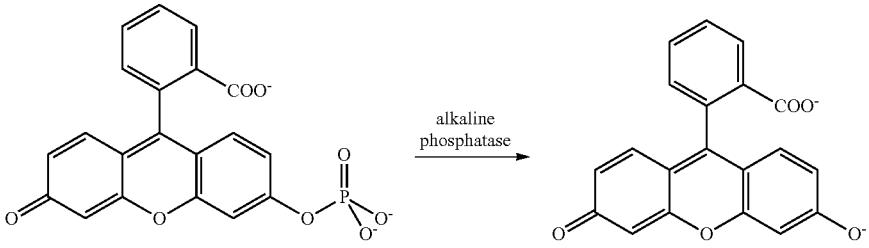 | +1 (−3 → −2) |
| 4 | 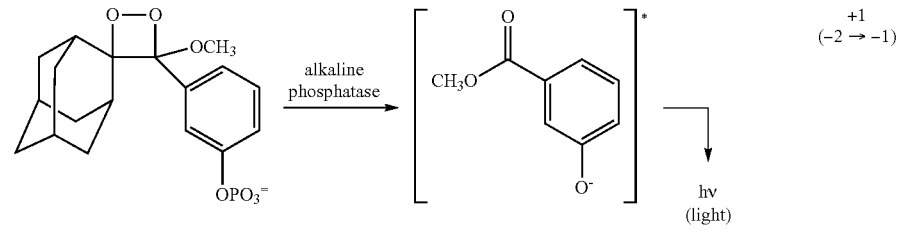 | +1 (−2 → −1) |

The reactions of entries 1 and 2 in Table 2 correspond to the charge state changes of entry 3 in Table 1, neutral substrate→anionic product. As such, these reactions are quite well suited for use in many embodiments, since the neutral substrate will be carried along with the bulk of the solvent, while the anionic detectable ELISA reaction product will be attracted to a detection channel that incorporates a cathodic electrode, and thereby be separated from the substrate (while at the same time be concentrated). In contrast, entries 3 and 4 of Table 2, though they each provide charge state changes of the same magnitude as those of entries 1 and 2 of Table 2, are less easily adaptable for particular embodiments. Entries 3 and 4 of Table 2 correspond to the charge state change described in Table 1, entry 6, in which a negatively charged substrate is converted to a negatively charged product. Thus, in each of the reactions of entries 3 and 4 from Table 2, both substrate and product would be attracted to the cathodic terminal in the device described in FIG. 3A. While the dramatic change in chromophoric properties attendant on the enzyme catalyzed cleavage reactions, it would nevertheless be the case that the sensitivity of the assay would be degraded due to background noise associated with the substrate. Though this disadvantage could be dealt with through the use of a more complicated microfluidic device (as discussed above for reactions of this charge-change type, in which use of an additional microfluidic side channel is described), this will often be an unattractive solution, making reactions of the types shown in entries 1 and 2 of Table 2 more desirable.

The reaction of entry 3 in Table 2 can serve to illustrate both some of the differences between the methods described herein and current ELISA methods, as well as a broad strategy for adapting otherwise unattractive enzyme/reactions used in current ELISA methods for use in the methods described herein. Shown in Table 3 are a series of compounds that can be synthesized by those adept in the art from commercially available fluorescein isothiocyanate and a variety of known amine compounds. Each successive entry in Table 3 represents a compound having an additional positive charge. In each case (and with comparable ease), alkaline phosphatase will cleave the phosphate group of the substrates providing detectable ELISA products with drastically improved chromophoric properties relative to the corresponding substrate, and there will be essentially no difference between the detectability of the products. And, in each case, the overall change in the net charge state on going from substrate to detectable ELISA reaction product is the same: +1. All of these substrates would give essentially the same results in current ELISA methods employing alkaline phosphatase. However, the various compounds in Table 3 would be of widely varying utility in the methods described herein. Entries 1 and 2 of Table 3 correspond to the charge state change illustrated by entry 6 in Table 1, with a negatively charged substrate going to a negatively charged detectable ELISA reaction product. As discussed in the context of both Tables 1 and 2, these substrates/reactions could be employed in certain embodiments, for example by use of more complicated microfluidic devices than might be desired, or at the expense of lower S/N associated with a lack of separation of substrate and ELISA product.

TABLE 3

| Entry | Substrate and reaction | Change in charge state |
|---|---|---|
| 1 | 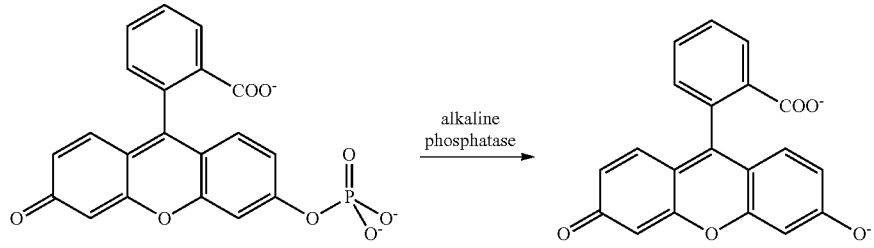 | +1 (−3 → −2) |
| 2 | 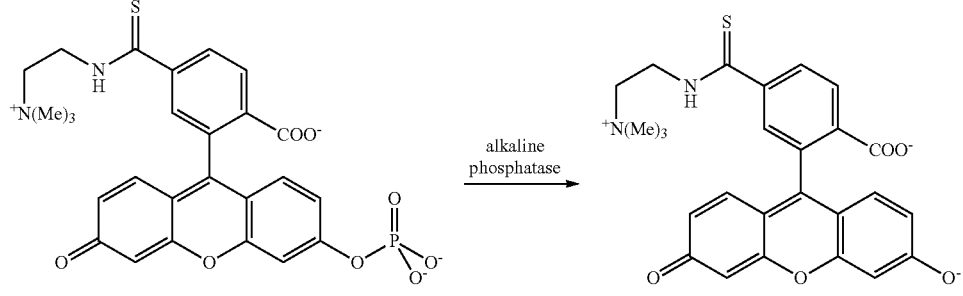 | +1 (−2 → −1) |
| 3 | 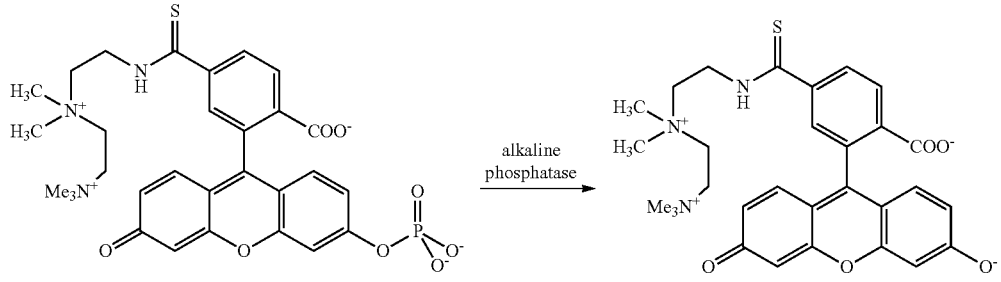 | +1 (−1 → 0) |
| 4 | 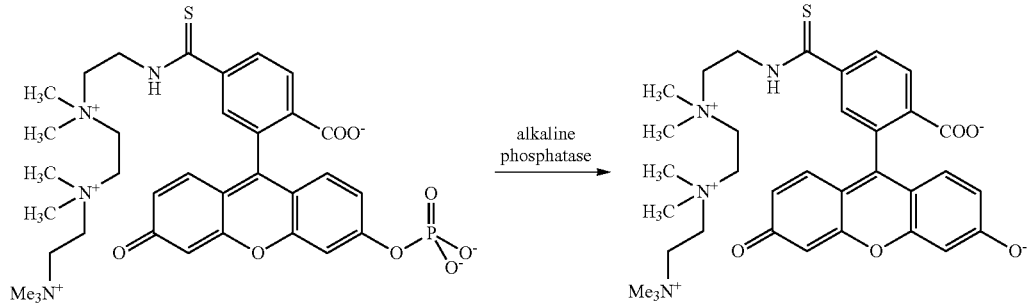 | +1 (0 → +1) |

Introduction of an additional positive charge to the base structure of the substrate leads to entry 3 in Table 3, and corresponds to the charge state change described in the context of entry 8 of Table 1, with a negatively charged substrate being converted to a neutral detectable ELISA reaction product. As discussed in the context of Table 1, though such embodiments may still have some advantage over current ELISA methods, they may be less desirable embodiments, since they give up the very large signal enhancement that is associated with a charge-based concentration of the ELISA product. Finally, when one adds yet another positive charge to the substrate, as shown in entry 4 of Table 3, one arrives at a substrate/reaction that represents exemplary embodiments.

The reaction shown in entry 4 of Table 3 corresponds to the charge state change of entry 4 in Table 1, with a neutral substrate going to a positively charged (and hence readily separable) detectable ELISA reaction product. It is worth noting that if yet another positive charge were to be added to the substrate, this would generally be considered counterproductive, since it would lead to a charge state change corresponding to entry 5 of Table 1, in which a positive substrate produces a positively charged detectable ELISA product. Thus, from the examples given here, it is clear that the operation of certain embodiments depends critically on both changes in charge state and the absolute charge states of substrate/products, but this dependence does not relate to how the change in charge state influences the chromophore of the detectable ELISA reaction product. These examples also illustrate that, by relatively simple and straightforward manipulations of the charge state of an initial substrate—manipulations and changes that occur far from the site of reaction of the enzyme, and far from the chromophore of the reaction product—it is possible to modify a currently employed ELISA substrate so as to make it conform to one of the most desirable of embodiments (e.g., those corresponding to the charge state changes of entries 1-4 in Table 1).

A significant difference between the methods described herein and current ELISA methods lies with the number and types of enzymes that can be employed. In current ELISA methods, only reactions that can transform a non-dye to a dye, or that can produce a dramatic change in chromophoric properties as a consequence of a bond cleavage reaction are suitable. This is because if a chromophore similar to that in the ELISA product is also present in the substrate, their signals will be indistinguishable, regardless of how much substrate is transformed to ELISA product; thus, it will not be possible to tell whether a catalyzed reaction has taken place, and in turn not possible to determine how much enzyme (and, by inference, analyte) is present. The limitation of current ELISA methods to classes of reactions of these types is undesirable. In particular, it would be advantageous to have a variety of enzyme/enzyme catalyzed reactions available that would accommodate a wide range of substrate types, thereby allowing multiple assays to be performed simultaneously. In fact, aspects of the present embodiments readily allow for a much wider range of enzyme catalyzed reactions to be employed in the ELISA component of the assay, and therefore allow embodiments in which multiple analytes can be detected with significantly greater ease and scope than current ELISA methodology.

Figure 5:
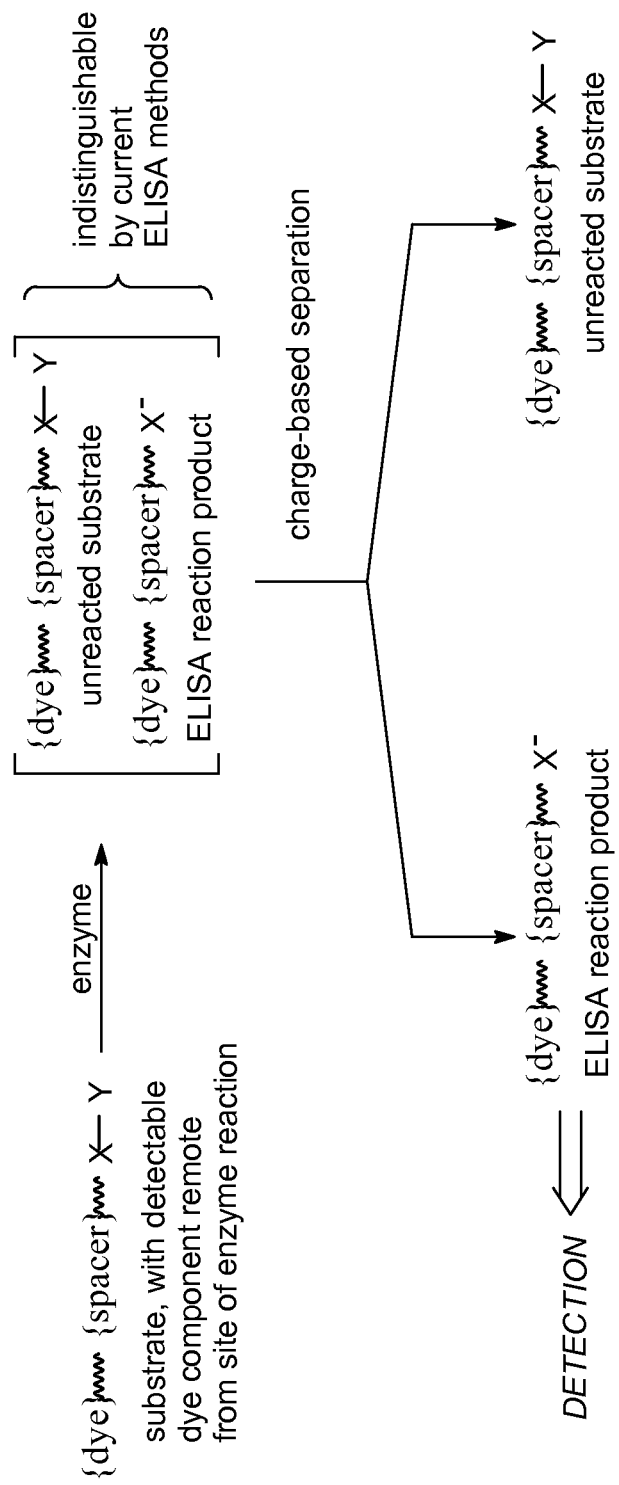
FIG. 5 provides an overview of an exemplary method embodiment identifying a charged-based separation step for separating ELISA reaction product from unreacted substrate.

The methods and practice described herein are more suited to the use of multiple enzymes as a consequence of the charge-based separation of the detectable ELISA reaction products. This rapid and convenient separation means that the same detectable component present in the detectable ELISA reaction product may be present, in unaltered form, in the substrate for the enzyme reaction. The important consequence of this with respect to the scope of certain embodiments is that, in contrast to current ELISA methodology, the enzymes used in the ELISA component of certain embodiments do not need to act at, or near, the detectable component of the substrate. Indeed, the only requirement of the enzyme/enzyme reaction in certain embodiments is that it produces a change in the charge state of the detectable ELISA reaction product relative to the starting enzyme substrate, so that the two can be separated. This is illustrated in FIG. 5, for a generalized bond cleaving reaction that results in a net negative charge formation in the portion of the cleaved molecule that includes the detectable dye component; note that the bond cleaved (and where the charge is formed) is separated by some significant distance (indicated by "spacer") from the dye. Other generalized examples are given below. Of course, it is still necessary that an enzyme be capable of being bound as some sort of conjugate to a surface, and that the detectable component of the substrate/ELISA reaction product not interfere substantially with the catalyzed reaction, but these do not represent overly onerous restrictions: many enzymes have been covalently modified (e.g., for attachment to surfaces, or for attachment of markers or probes), and the chromophore can be attached quite remotely to the site of enzyme action, thereby making it unlikely that it would interfere.

The generalized example of an enzyme catalyzed reaction suitable for embodiments is but one example of the type of transformation that can be employed. Once again, the charge based separation with subsequent detectable ELISA product concentration only requires a different charge state between substrate and product, though it is certainly the case that some of the charge state changes will generally be more preferred than others, as discussed above in the context of Tables 1-3. Other examples of generalized enzyme catalyzed reactions that could be used in various embodiments are illustrated in Table 4 (which also includes the example given in FIG. 5). In Table 4, only the portion of the detectable ELISA reaction product is shown; that is, side products are ignored. It should be clear from the discussion above in the context of Table 3 that, depending on the charge state of the remainder of the molecule (e.g., charges associated with the dye or spacer group), the detectable ELISA reaction product might be drawn to either a cathode or anode; the change in charge state given simply refers to the change in relative charge between the substrate and the detectable ELISA reaction product. It is also the case the change in charge states given represent a simple indication of the difference in charge; that is, depending on the specific reactions involved, "+" can mean an increase in positive charge (or a less negative charge) by one, or by two, or by three, etc. charge units. It is also the case that in Table 4, that the symbols "X" and "Y" may represent discreet atoms, or may be specific atoms having further groups attached to them (e.g., alkyl, cycloalkyl, alkenyl, cycloalkenyl, aryl, heteroalkyl, heterocycloalkyl, heteroaryl), and that these further groups attached to them may include charged groups that are positive (including, but not limited to ammonium, phosphonium, sulfonium, complexed cations) or negative (including, but not limited to carboxylate, phosphonates, phosphates and their esters, sulfonates, sulfates). It should also be understood that X and Y may comprise molecular subunits having multiple atoms; that is, X and/or Y may be an aromatic ring or heteroaromatic ring. The "spacer" in these reactions will typically be one to sixty atoms (not including hydrogens) and serves to separate the "dye" from the site of reaction at X and/or Y. This "spacer" may be entirely carbon, or include heteroatoms chosen from oxygen, nitrogen, sulfur and phosphorous, but will usually not include oxygen-oxygen or nitrogen-oxygen bonds. The "spacer" may be a linear ordering of atoms, or may include one or more rings (cycloalkyl, aryl, heteorcycloalkyl, heteroaryl) and may be substituted with groups as described above for X and Y that confer varying desirable properties to the substrate and/or resulting detectable ELISA reaction product, including water solubility, groups that enhance the binding and/or rate of reaction of the substrate with the enzyme chosen, and most especially groups that allow the overall charge of the substrate to be adjusted according to the charge-state change expected in the enzyme catalyzed reaction. The term "dye" is used, in part, for convenience. It should be understood to comprise any source of detectabililty in the molecule, and as such includes the dye precursors in use with current ELISA methods. In addition to dye precursors for current ELISA methods, the "dye" may in fact be a dye in the conventional sense of the word, including but not limited to azo dyes, xanthene dyes, anthraquinone dyes, acridine dyes, oxazine dyes, thiazene dyes, triarylmehtane dyes, diarylmethane dyes, quinoline styryl dyes, phthalocyanine dyes, squarene dyes and polyalkene dyes. The "dye" may also be a precursor to a chemiluminescent molecule that can be activated to emit light at a time controlled by the user. The "dye" may also be a compound that is capable of being oxidized or reduced in some facile process that can be detected electrochemically. The "dye" may also comprise a radioactively labeled subunit (e.g., by $^{32}P$ or $^{3}H$ or other common radioactive labels common in the art).

TABLE 4

| Entry | Reaction | Change in charge state |
|---|---|---|
| 1 | {dye}∼∼{spacer}∼∼ X—Y →enzyme→ {dye}∼∼{spacer}∼∼ X⁻ | − |
| 2 | {dye}∼∼{spacer}∼∼ X—Y →enzyme→ {dye}∼∼{spacer}∼∼ X⁺ | + |
| 3 | {dye}∼∼{spacer}∼∼ X →enzyme→ {dye}∼∼{spacer}∼∼ X—Y⁻ | − |
| 4 | {dye}∼∼{spacer}∼∼ X →enzyme→ {dye}∼∼{spacer}∼∼ X—Y⁺ | + |
| 5 | {dye}∼∼{spacer}∼∼ X →enzyme→ {dye}∼∼{spacer}∼∼ Y⁻ | − |
| 6 | {dye}∼∼{spacer}∼∼ X →enzyme→ {dye}∼∼{spacer}∼∼ Y⁺ | + |
| 7 | {dye}∼∼{spacer}∼∼ X →enzyme→ {dye}∼∼{spacer}∼∼ X⁻ | − |
| 8 | {dye}∼∼{spacer}∼∼ X →enzyme→ {dye}∼∼{spacer}∼∼ X⁺ | + |

The general outline of enzyme reactions given in this paragraph should not be assumed to be inclusive, but merely as an indication of some of the types of reactions that would produce the changes in charge state given in Table 4. Entries 1 and 2 in Table 4 represent bond cleaving reactions that result in a change in charge state. Entry 1 in Table 4 can be exemplified by reactions catalyzed by esterases (e.g., $RCOOCH_3$ undergoing hydrolysis to the corresponding carboxylate $RCOO^-$ catalyzed by porcine liver esterase, or by a lipase). Entry 2 in Table 4 can be exemplified by action of a phosphatase (as discussed in greater detail below), or by other reactions that remove a negative charge from a molecule (e.g., some transaldolase reactions in which the side product not bearing the dye includes a phosphate group), or by reactions involving hydrolysis of an amide (e.g., an endopepetidase, or an amide acylase that catalyzes $R—NHC(O)CH_3 \rightarrow RNH_3^+$). Entry 3 in Table 4 illustrates an increase in charge due to coupling of two molecular subunits, as might be seen in a kinase reaction (adding a phosphate group) or an aldolase reaction run with an excess of aldol substrate. Similarly, entry 4 in Table 4 involves generation of positive charge, for example by a methylation reaction. Entries 5 and 6 in Table 4 correspond to reactions in which there is some type atom replacement reaction, for example in a reaction catalyzed by a transaminase in which a carbonyl is first converted to a positively charged iminium ion and then an amine/ammonium group (corresponding to entry 6 in Table 4), or the reverse process in which an amine/ammonium group is converted to a carbonyl (corresponding to entry 5 in Table 4). The entries 7 and 8 in Table 4 include reactions in which reductions and oxidations of a functional group or grouping of atoms occur. For example interconversions of $NAD^+$ and NADH would correspond to entries 7 and 8, respectively in Table 4. Similarly, reduction of a quinone to a hydroquinone would (under conditions of high pH) produce a product with an additional negative charge (entry 7 in Table 4), while oxidation of any of a number of aromatic systems (e.g., by horseradish peroxidase) would produce a positive charge (note that this is regardless of whether the positive charge so-produced was part of the detectable chromophore of the molecule). Entry 7 in Table 4 can also be exemplified by enzymes involved in the oxidation of thiols to sulfites.

Table 5 provides more specific examples of enzymes that will provide changes in charge state in ELISA reactions employed for various embodiments. The focus of this Table is reactions that occur remotely to the detectable component of the substrate/product. Thus, for example, the many reactions of horseradish peroxidase that lead to changes in charge state of a pro-dye to dye are not included, though of course they will be useful in a variety of embodiments. The examples of Table 5 are given because they illustrate, in brief, a wide range of charge state changes that can be accomplished for ELISA substrates using reactions that are not commonly employed in current ELISA methods (or have been employed differently, wherein reaction occurs at the detectable component). The examples are also chosen because the enzymes involved have either demonstrated applicability in ELISA reactions, or have at least been reported to have been conjugated in ways that are applicable to making enzyme conjugates desirable for exemplary embodiments, while still demonstrating high levels of enzyme activity. The initial number given in the "change in charge state" column represents the change that would result under ELISA conditions that are roughly at the pH rate maximum for the enzyme; numbers given in parentheses represent the change in charge state that would result using some simple pH-change embodiment (that is, by addition of acid or base through auxiliary channel K). It should be understood that when enzymes are shown in Table 5 (and in preceding Tables), the actual species used in certain embodiments will be the enzymes indicated conjugated to an appropriate binding group (e.g., an antibody or biotin or the like).

TABLE 5

| Entry | Reaction | Change in charge state |
|---|---|---|
| 1 | {dye}∼{spacer}∼R—OPO$_3^=$ →(alkaline phosphatase)→ {dye}∼{spacer}∼R—OH | +2 |
| 2 | {dye}∼{spacer}∼Ar—OPO$_3^=$ →(alkaline phosphatase)→ {dye}∼{spacer}∼Ar—O$^-$ | +1 (+2) |
| 3 | {dye}∼{spacer}∼C(=O)OR →(porcine liver esterase)→ {dye}∼{spacer}∼C(=O)O$^-$ | −1 |
| 4 | {dye}∼{spacer}∼C(=O)NH-CH(CH$_2$CH$_2$CH$_2$CH$_2$NH$_3^+$)-C(=O)O$^-$ →(carboxypeptidase B)→ {dye}∼{spacer}∼C(=O)O$^-$ | −1 |
| 5 | {dye}∼{spacer}∼C(=O)O-CH$_2$CH$_2$-N$^+$(CH$_3$)$_3$ →(butyryl cholinesterase)→ {dye}∼{spacer}∼C(=O)O$^-$ | −2 (−1) |

In the example of entry 1 of Table 5, alkaline phosphatase hydrolyzes an alkyl phosphate ester to provide an alcohol product and an overall change in charge state of +2. Alkyl phosphates are not common substrates in ELISA reactions, since the product has a neutral alcohol (rather than a phenolic anion) that does not represent a significant perturbation to a dye chromophore. Of course, for certain embodiments, this doesn't matter; it is solely the change in charge state that is made use of, as a means for separating the product from starting substrate, and then concentrating it for detection. Alkaline phosphatase shows extremely broad substrate specificity, and thus this ELISA reaction will be applicable to a wide range of substrates. The example of entry 2 in Table 5 involves the cleavage of an aryl phosphate to give an anionic phenolate product, and is similar to both the first entry of Table 5, as well as reactions catalyzed by alkaline phosphatase in many current ELISA methods. However, it differs from entry 1 in Table 5 in that it will produce a +1 change in the net charge under the conditions of the enzyme reaction (though by use of a post-ELISA pH change this can become a net +2 change in charge). And, as has been illustrated in prior examples, with the methods and practices described herein, the oxygen involved in the oxygen-phosporous bond being cleaved does not have to be attached to the detectable component of the substrate (though it certainly can be). Thus, embodiments that use this reaction are of much broader scope than current ELISA methods.

Both entries 3 and 4 of Table 5 produce changes in charge state of −1, and illustrate the use of enzymes that are not commonly employed in current ELISA methods. In entry 3 in Table 5, in which a porcine liver esterase conjugate is employed, the ester group R may be aryl or alkyl, but will most commonly be methyl, since porcine liver esterase exhibits high reaction rates with such substrates; rabbit liver esterase would be more appropriately employed with aryl esters. An antibody-porcine liver esterase has been reported in a patent, and it is known that the enzyme can be conjugated to polyethyleneglycol derivatives while still retaining activity; thus, it should be effective in assays described herein when conjugated to appropriate binding agents. In some instances it may be preferable to employ a lipase (or other esterases) as an alternative to PLEase. The reaction of entry 4, in which a carboxypeptidase B conjugate is used for the ELISA reaction, is noteworthy by virtue of the fact that an extraordinarily low background rate would be expected for the uncatalyzed reaction. Carboxypepetidase B has been conjugated to antibodies that have then been used in certain experimental drug therapy applications. It does not appear to have been used in ELISA reactions, presumably because the nature of the reaction catalyzed is such that no significant change in a chromophore can reasonably be envisioned—making it useless for current ELISA methods. Of course, for embodiments described herein, the fact that the reaction results in a change in charge state makes the reaction of high utility. The enzyme is an exopeptidase that is highly specific with respect to the terminal amino acids it will cleave, being limited to unmodified lysine, arginine and ornithine; thus, when conjugated to proteins (e.g., antibodies or streptavidin) it is important that they not have terminal carboxy terminal lysine, arginine or ornithine, though this potential limitation has been addressed by chemically modifying these groups. In fact, the high substrate specificity of the enzyme is what makes it possible to conjugate it to proteins—something that, on the face of it, would seem to be unwise (since it is designed to digest proteins). Of course, for suitable conjugates, it may be possible to use other carboxypeptidases (e.g., carboxypeptidase A, with a preference for carboxy terminus amino acids having aromatic side chains) provided that there is compatibility between the protease and the component to which it is being conjugated.

Entry 5 in Table 5 illustrates the potential use of the enzyme butyryl cholinesterase to produce a change in charge state of −2 (or −1 if a pH-change embodiment is implemented in such assays). This enzyme does not appear to have been used in ELISA reactions, presumably for the same reasons that carboxypeptidase B has not been used: no plausible substrate exists that would produce a dramatic change in chromophoric properties upon hydrolysis. Though the "true" purpose of butyryl cholinesterase is still unknown, it appears to be useful in hydrolyzing/detoxifying esters having positive charge near the ester bond to be cleaved. So, in addition to being active with butyryl choline, the enzyme shows activity towards cocaine. In this context, the enzyme has been conjugated to a variety of small molecules (while retaining activity) for the purpose of treating cocaine toxicity. That such conjugation can be carried out while retaining enzymatic activity strongly suggests this enzyme can be successfully employed in the form of a conjugate in certain embodiments.

EXAMPLE 4

Simultaneous Measurement of Two Analytes

This example serves to illustrate many useful features of the methods and devices described above, both in terms of their utility, as well as its distinction from prior art in the ELISA field. Thus, it is possible to assay two analytes simultaneously using substrates having the same detectable component, and in which each substrate is converted to detectable ELISA reaction products having the same detectable component. Such a dual assay could not be accomplished using conventional ELISA methods, since these require a change in the chromphoric properties between substrate and catalytic ELISA reaction product; furthermore, any conventional dual ELISA assay would require the detectable component of the detectable catalytic ELISA reaction products to be distinguishable. However, the methods and practices described above make this dual assay in which the same detectable component is comprised in both substrates and in both detectable ELISA reaction products relatively straightforward. This example also illustrates the versatility with respect to choice of enzyme and enzyme reactions that are conferred through the various embodiments: in one case, a conventional ELISA enzyme is employed, but in a reaction that occurs remotely from the detectable component, while in the other case an enzyme is employed that has not been commonly used in ELISA assays.

Compound A in the following scheme is a substrate for alkaline phosphatase (APase) that comprises a highly detectable rhodamine moiety attached to a phosphate group by way of a water solubilizing, bio-compatible polyethylene glycol tether. The quaternary dimethylammonium group is present so that the overall charge of the molecule at >pH 8 will be overall neutral, with the doubly negative charge of the phosphate group balanced by the cationic rhodamine and the quaternary ammonium. Upon hydrolysis by alkaline phosphatase-antibody conjugate, the neutral compound A is converted to the dicationic compound $A^{2+}$, that will be attracted towards a ground (negatively charged) electrode, while the neutral substrate A will be substantially unaffected by the electric field. Compound B in the following scheme is a zwitterionic, overall neutral substrate for pig liver esterase (PLEase) that also comprises a highly detectable rhodamine moiety, in this case further attached to a carboxylic ester by way of a water solubilizing, bio-compatible polyethyleneglycol tether. On hydrolysis by a pig liver esterase-antibody conjugate, the neutral B is converted to anionic $B^-$ which is attracted to an electrode at high voltage (positive), while the neutral B is substantially unaffected.

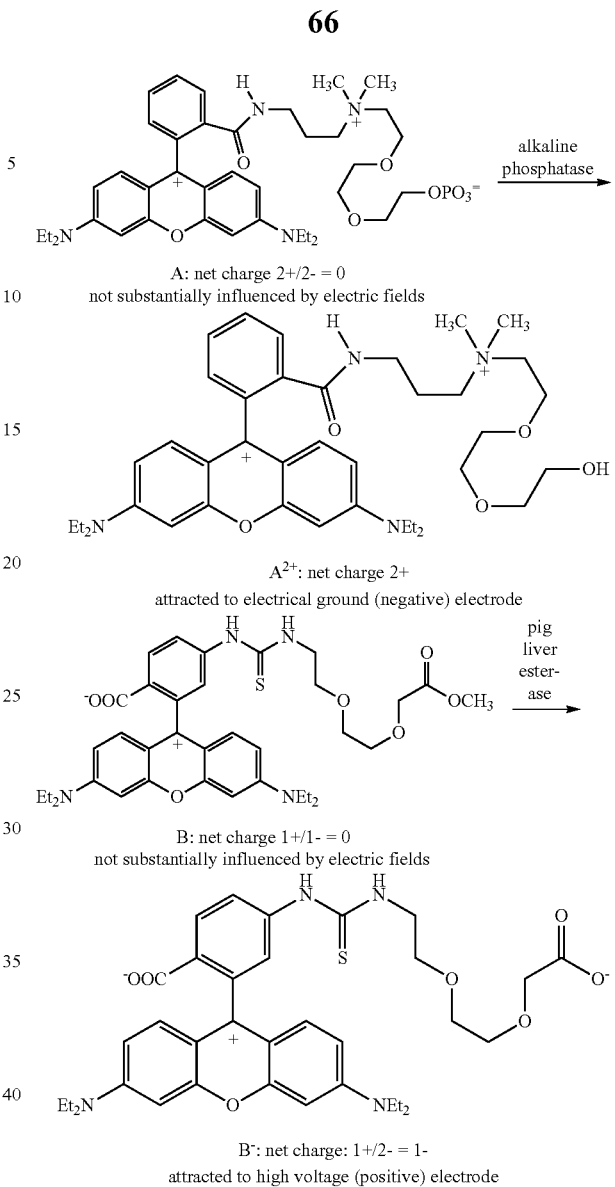

The two substrates, A and B can be employed in a simultaneous assay for two analytes α and β in the following manner using the more elaborate microfluidic device shown in FIG. 6. An ELISA surface is prepared in region A as described above, but by using a mixture of two capture antibodies for analytes α and β. In practice, it is desirable to empirically determine the relative proportions of the two antibodies that provide optimal detection sensitivities, since this may depend on the relative amounts of the two analytes. Following introduction of the sample containing analytes α and β, incubation, and washing, a mixture of two different antibody-enzyme conjugates is introduced. The first antibody-enzyme conjugate comprises an antibody for analyte α conjugated to alkaline phosphatase, while the second antibody-enzyme conjugate comprises an antibody for analyte β conjugated to pig liver esterase. After incubation and washing, a mixture of the two substrates at pH 8.5 is introduced through reservoir 1, this pH being chosen as a compromise between optimal pH-rate maxima of the two enzymes. It will usually be desirable to also introduce a flow of buffer from reservoirs 2a and 2b. These flows provide a "pinching" action to compress the flow from the ELISA region A, thereby decreasing intrusion of unreacted substrates A and B into the microfluidic trapping regions E and F; due to the potential established between electrodes at reservoirs 3 and 4, the catalytic reaction products $A^{2+}$ and $B^-$ are transported electrophoretically to trapping zones 4 and 3, respectively, where the build-up in concentration is monitored at one or more known time intervals, thereby allowing the concentrations of analytes α and β to be inferred.

Substrate A is synthesized, as summarized in the below scheme, in a straightforward fashion by successive reaction of rhodamine B base with phosphorus oxychloride and excess N,N-dimethyl-1,3-propanediamine (as per Dujols, V.; Ford, F.; Czarnik, A. W., J. Am. Chem. Soc. 1997, 119, 1565) to give Aa, which is in turn alkylated with 2-(2-(iodoethoxy)ethoxy) ethanol to provide the quaternary ammonium salt Ab. This is phosphorylated by standard phosphoramidite methodology (Perich, J. W.; Johns, R. B., Tetrahedron Lett. 1987, 28, 101) to the bis-methyldiphenylsilylethyl phosphate using excess N,N-diisopropylamino-bis(2-methyldiphenylsilylethoxy) phosphoramidate in the presence of benzylthiotetrazole, followed by oxidation with hydrogen peroxide, and the phosphate product immediately deprotected to A by treatment with hydrofluoric acid in acetonitrile (Ross, K. C.; Rathbone, D. L.; Thomson, W.; Freeman, S., J. Chem. Soc. Perkin Trans. I, 1995, 421). Compound B is prepared by N-deprotecting (aqueous piperidine) the methyl ester of commercially available (Aldrich Chemical Co.) 1-(9H-fluoren-9-yl)-3-oxo-2,7,10-trioxa-4-azadodecan-12-oic acid (FmocNH(CH2CH2O)2CH2COOH) and coupling the resulting amine with rhodamine B isothiocyanate.

EXAMPLE 5

Electrochemical Detection Strategies

Figure 7:
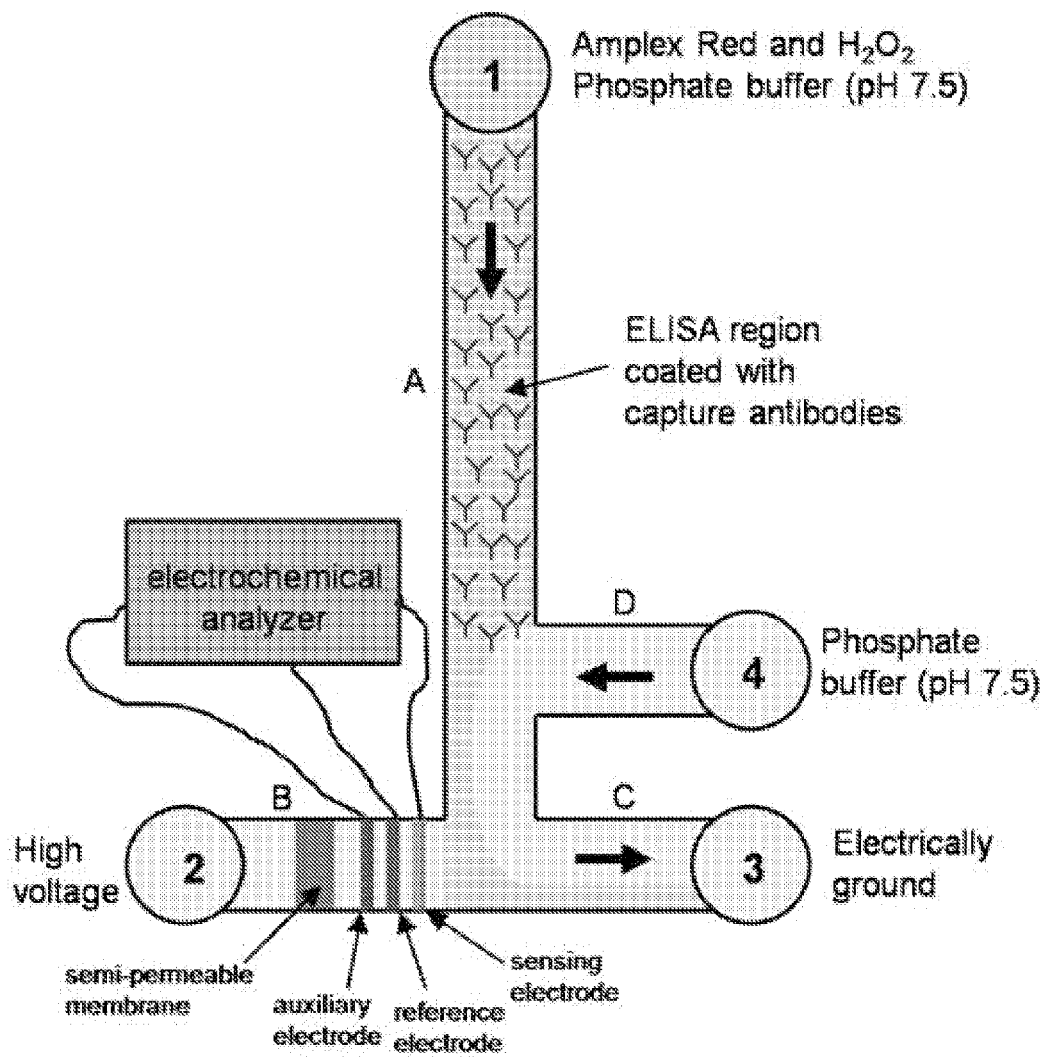
FIG. 7 provides a schematic illustration of an exemplary microfluidic device embodiment utilizing an electrochemical detection scheme.

There are methods for detection of the catalytic reaction product(s) that do not rely on optical methods (that is chromophoric moieties in the product), and it will generally be possible to apply these alternate detection methods to the methods and devices described above. One mode of detection that is of particular interest in this regard is electrochemical sensing. Electrochemical sensing can be one of the most sensitive detection methods and can be readily coupled to ELISA assays. In this method of detection, the ELISA reaction product undergoes an electrochemical reaction at the sensing electrode producing an electrical signal that can be correlated to the concentration of this electroactive species. A straightforward implementation of this detection method involves placement of one or more microelectrodes in the trapping zone on the same side of the semi-permeable membrane as the main microfluidic channel, where the concentration of the ELISA reaction product is expected to be the maximum (see FIG. 7). In one preferred embodiment there are three microelectrodes in the microfluidic trapping zone. Two of these (the sensing and auxiliary electrodes) are involved in the electrochemical oxidation reactions, while a reference electrode (optionally located in another channel of the device) serves as a reference/control standard for accomplishing the electrochemical reactions. Additionally in this preferred embodiment, there is an electrode placed behind the semi-permeable membrane, in reservoir 2. A steady DC elec-

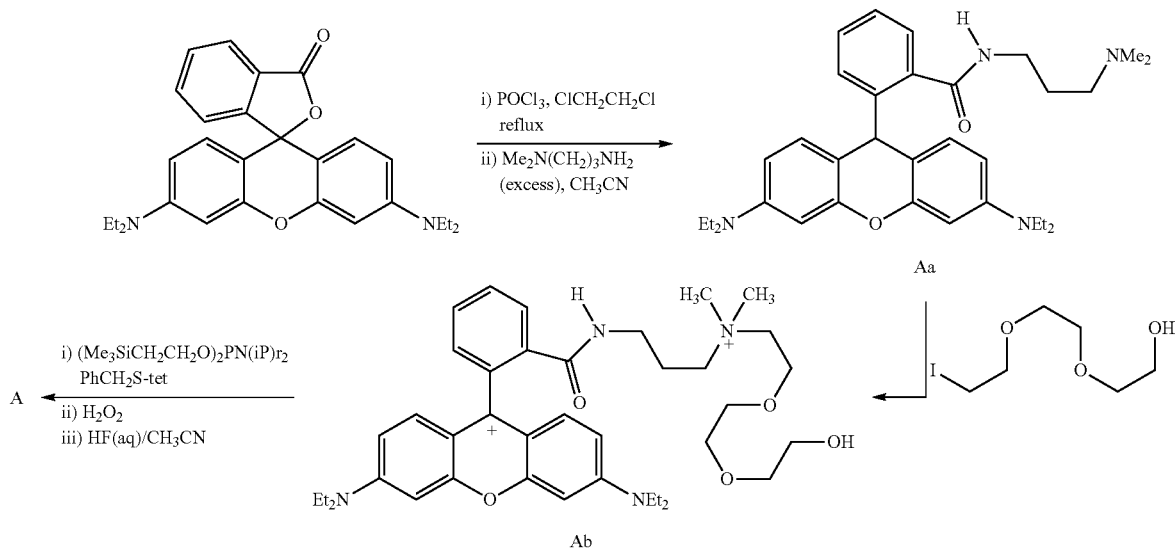

Figure 6:
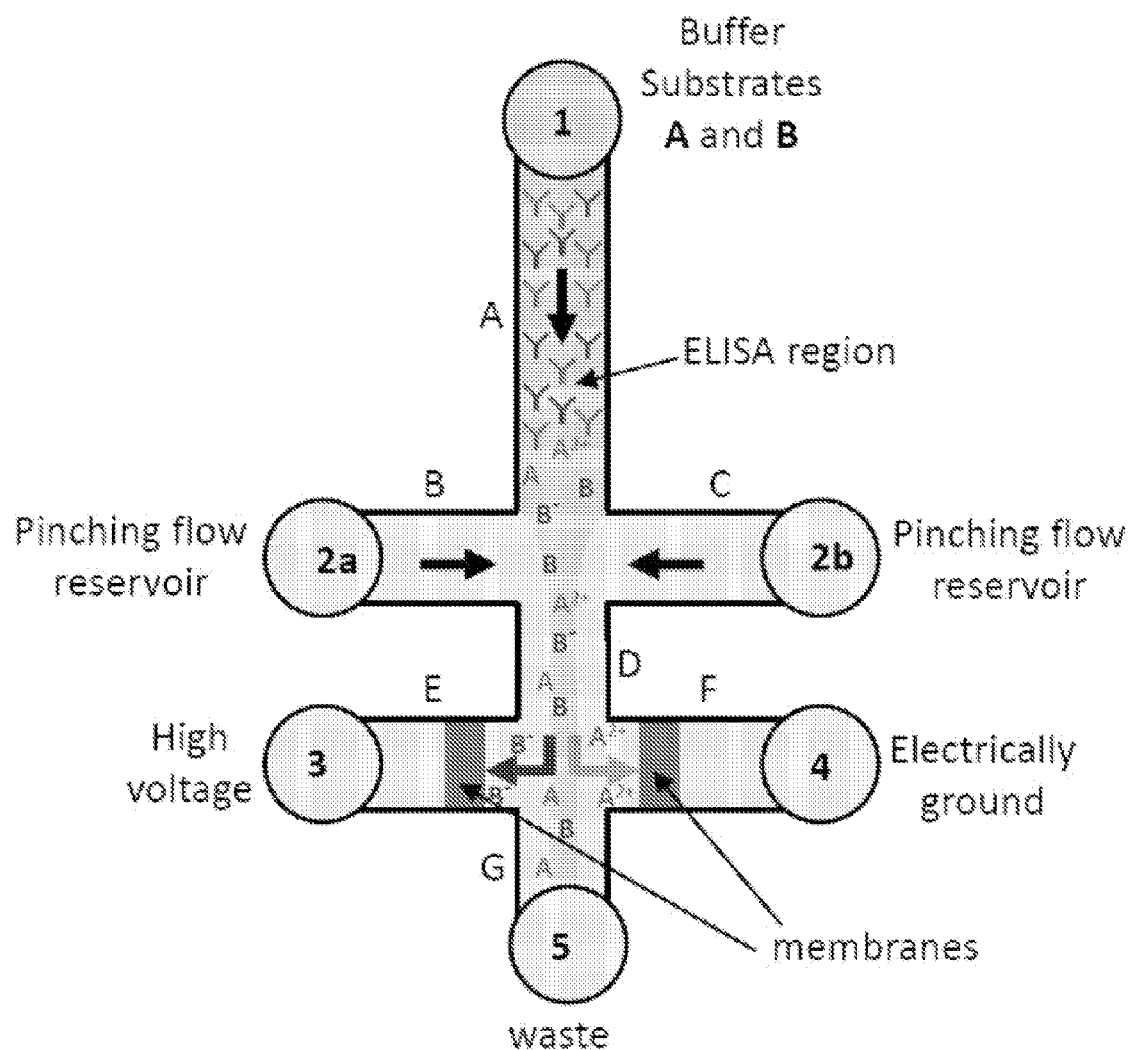
FIG. 6 provides a schematic illustration of an exemplary microfluidic device embodiment for simultaneous detection of multiple analytes.

Caption for FIG. 6: FIG. 6 illustrates a microfluidic device embodiment for carrying out multiplex ELISA assays. Enzyme substrates A and B are introduced to an ELISA region and transformed in part by enzyme-antibody conjugates to catalytic ELISA reaction products $A^{2+}$ and $B^-$, which are transported to microfluidic trapping regions F and E, respectively as a consequence of a voltage potential between reservoirs 3 and 4. The neutral substrates A and B are substantially unaffected by the voltage potential and are carried to waste. Optional "pinching" flows from reservoirs 2a and 2b concentrate the stream from the ELISA region, lessening contamination of the microfluidic trapping regions by substrate.

tric field is applied from this later electrode in reservoir 2 that draws the catalytic ELISA reaction products into the trapping zone, while the voltages applied at the sensing/reference/auxiliary electrode system drive the electrochemical detection process. The decoupling of the voltages applied at reservoir 2 from that at the sensing electrode system will allow the use of both DC and AC voltametric/amperometric techniques in assays that will allow independent optimization of the detection system from the pre-concentration methods previously described. Moreover, the applicability of AC voltametric/amperometric techniques may allow further amplification in the signal to the noise ratio in the device through the use of a reversible redox couple as the electroactive reporter species. The electrochemical cycling of such species allows the detection of the same reporter molecules multiple times, enhancing their detectablity even more than what could be possible using optical sensing methods. In fact, such signal amplification has been already demonstrated for immunoassays using the catalytic enzyme β-galactosidase in conjunction with the substrate species p-aminophenol.

An alternate embodiment employing electrochemical detection may be less broadly applicable, but may offer substantial advantages in some microfluidic device embodiments. If the length of the channels in the microfluidic device are sufficiently short, then it is possible to generate large electric fields using small voltages. This combination—large field with low voltage—may allow the same electrode to serve a dual purpose of transporting the catalytic ELISA reaction products (that is best accomplished by a large field) while at the same time providing a sufficiently small voltage that a controllable electrochemical detection cycle can be established. In general, this dual purpose will best be accomplished using an AC current with a DC bias, the latter aspect serving the pre-concentration role. In addition to the simplicity of design associated with fewer electrodes, this embodiment will not generally make use of a semi-permeable membrane, providing a substantial simplification of device fabrication.

REFERENCES

"Enzyme Immunoassays: from concept to product development", Chapman and Hall, New York, 1996, ISBN0-412-05601-1.

Kricka, L. J.; Wild, D. in Wild, D. "The Immunoassay Handbook," Elsevier, New York, 2005, Chapter 11, "Signal Generation and Detection Systems (Excluding Homogeneous Assays)," pp. 192-211.

U.S. Patent Application Publication Numbers US 2009/0123336, US 2007/0074972, US 2009/0242429, US 2006/0252143, US 2007/0111353, US 2008/0012007, US 2006/0105449, US 2010/0075340, US 2008/0108095, US 2003/0153024, US 2004/0115709, US 2004/0115838, US 2004/0202994, US 2005/0000811, US 2008/0274493.

U.S. Pat. No. 6,342,347, 6,027,890, 6,815,212, 7,312,060, 7,749,445.

European Patent Application Publication Numbers EP 1199558, EP 0962464.

Japanese Patent Application Publication JP 2004-219103.

International Patent Application Publication Numbers WO 2008/072153.

Chinese Patent Application Publication Number CN 101201350.

Cheow, L. F.; Ko, Sung Hee; Kim, Sung Jae; Kang, Kwan Hyoung; Han, J., Increasing the Sensitivity of Enzyme-Linked Immunosorbent Assay Using Multiplexed Electrokinetic Concentrator, Anal. Chem. 2010, 82(8), 3383-8.

Reyes, D. R., Lossifidis, D., Auroux, P. A., Manz, A., Anal. Chem. 2002, 74, 2623-2636.

H. Y. Wang., R. S. Foote., S. C. Jacobson., J. H. Schneibel., J. M. Ramsey. Sens. Actuators B, 1997, 45, 199-207.

Thomas J H, Kim S K, Hesketh P J, Halsall H B, Heineman W R, "Bead based electrochemical immunoassay for bacteriophage MS2" Anal. Chem. 2004, 76: 2700-2707.

Kraus et al. (Mar. 19, 2010) "Quantitative measurement of human anti-HCV Core immunoglobulins on an electrical biochip platform" Biosensors and Bioelectronics doi:10.1016/j.bios.2010.03.026 1-7

Yang et al (2010) "Lab-on-a-chip for carbon nanotubes based immunoassay detection of Staphylococcal Enterotoxin B (SEB)" Lab Chip10:1011-1017

Liu et al. (Sep. 14, 2009) Microchip-based ELISA strategy for the detection of low-level disease biomarker in serum Analytica Chimica Acta Volume 650, Issue 1,: 77-82

He et al. (2009) "Design and testing of a microfluidic biochip for cytokine enzyme-linked immunosorbent assay" Biomicrofluidics 3: 022401-022401-17

Miyaguchi et al. (Jan. 30, 2009) "Rapid analysis of methamphetamine in hair by micropulverized extraction and microchip-based competitive ELISA" Forensic Science International 184(1-3): 1-5

Bothara et al. (August 2008) "Nanomonitors: electrical immunoassays for protein biomarker profiling" Nanomedicine 3(4): 423-436

Heyries et al. (Jul. 15, 2008) "Microfluidic biochip for chemiluminescent detection of allergen-specific antibodies" Biosensors and Bioelectronics 23(12): 1812-1818

Stratis-Cullum et al (July 2008) "Intensified biochip system using chemiluminescence for the detection of *Bacillus globigii* spores" Analytical and Bioanalytical Chemistry 391 (5): 1655-1660

Myong (Apr. 1, 2004) "Miniature biochip system for detection of *Escherichia coli* O157:H7 based on antibody-immobilized capillary reactors and enzyme-linked immunosorbent assay" Analytica Chimica Acta 507(1): 115-121

Albers (October 2003) "Electrical biochip technology—a tool for microarrays and continuous monitoring" Analytical and Bioanalytical Chemistry 377(3): 521-527

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

When a group of substituents is disclosed herein, it is understood that all individual members of those groups and all subgroups and classes that can be formed using the substituents are disclosed separately. When a Markush group or other grouping is used herein, all individual members of the group and all combinations and subcombinations possible of the group are intended to be individually included in the disclosure. As used herein, "and/or" means that one, all, or any combination of items in a list separated by "and/or" are included in the list; for example "1, 2 and/or 3" is equivalent to "'1' or '2' or '3' or '1 and 2' or '1 and 3' or '2 and 3' or '1, 2 and 3'".

Every formulation or combination of components described or exemplified can be used to practice the invention, unless otherwise stated. Specific names of materials are intended to be exemplary, as it is known that one of ordinary skill in the art can name the same material differently. One of ordinary skill in the art will appreciate that methods, device elements, starting materials, and synthetic methods other than those specifically exemplified can be employed in the practice of the invention without resort to undue experimentation. All art-known functional equivalents, of any such methods, device elements, starting materials, and synthetic methods are intended to be included in this invention. Whenever a range is given in the specification, for example, a temperature range, a time range, or a composition range, all intermediate ranges and subranges, as well as all individual values included in the ranges given are intended to be included in the disclosure.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The invention illustratively described herein suitably may be practiced in the absence of any element or elements, limitation or limitations which is not specifically disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method for detecting a target analyte, the method comprising the steps of:
    providing a microfluidic device comprising a binding surface in fluid communication with a microfluidic trapping region and at least two electrodes, wherein the microfluidic trapping region comprises a semi-permeable membrane and wherein the binding surface comprises binding molecules capable of selectively binding to the target analyte;
    providing to the binding surface a first solution comprising the target analyte molecules, wherein at least a number of the target analyte molecules selectively bind to the binding molecules of the binding surface to provide a binding surface having bound target analyte molecules;
    providing to the binding surface having the bound target analyte molecules a second solution comprising catalyst molecules, wherein at least a number of the catalyst molecules further binds directly or indirectly to the target analyte molecules bound to the binding surface;
    providing to the binding surface having the bound target analyte molecules and the catalyst molecules a third solution comprising substrate molecules, wherein at least a number of the substrate molecules undergo a catalytic chemical reaction with the catalyst molecules bound directly or indirectly to the target analyte molecules bound to the binding surface, thereby directly or indirectly producing reaction product molecules having an ionic charge different from an ionic charge of the substrate molecules;
    transporting at least a number of the reaction product molecules into the microfluidic trapping region by applying an electrical potential between the at least two electrodes, wherein at least one electrode is positioned in the microfluidic trapping region and wherein the electrical potential provides a force attracting the reaction product molecules toward the microfluidic trapping region;
    concentrating the reaction product molecules in the microfluidic trapping region in front of, at a surface of and/or within the semi-permeable membrane; and
    detecting an amount of the concentrated reaction product molecules in the microfluidic trapping region in front of, at the surface of and/or within the semi-permeable membrane.

2. The method of claim 1, further comprising the step of determining an amount of the catalyst molecules bound to the binding surface from the detected amount of the concentrated reaction product molecules after one or more time intervals.

3. The method of claim 2, further comprising the step of determining an amount of the target analyte in the first solution from the determined amount of the catalyst molecules bound to the binding surface after one or more time intervals.

4. The method of claim 1, wherein the binding surface comprises: antigens of antibodies, antibodies, biotin, streptavidin, aptamers, nucleic acids, peptide nucleic acids; conjugates between antigens of antibodies, antibodies, biotin, streptavidin, aptamers, nucleic acids, peptide nucleic acids; or any combination of these.

5. The method of claim 1, wherein the catalyst molecules comprise a catalytically active group, antigens of antibodies, antibodies, biotin, streptavidin, aptamers, nucleic acids, peptide nucleic acids, alkaline phosphatase, acid phosphatase, horseradish peroxidase, beta-galactosidase, glucose oxidase, carboxypeptidase B, porcine liver esterase, rabbit esterase, lipase, butyryl cholinesterase, arginase, a catalyst for a bond cleavage reaction, a catalyst for a bond forming reaction, a catalyst for an oxidation reaction, a catalyst for a reduction reaction or any combination of these.

6. The method of claim 1, wherein the substrate molecules are Amplex red, galactose-ONP, fluroescein phosphate,

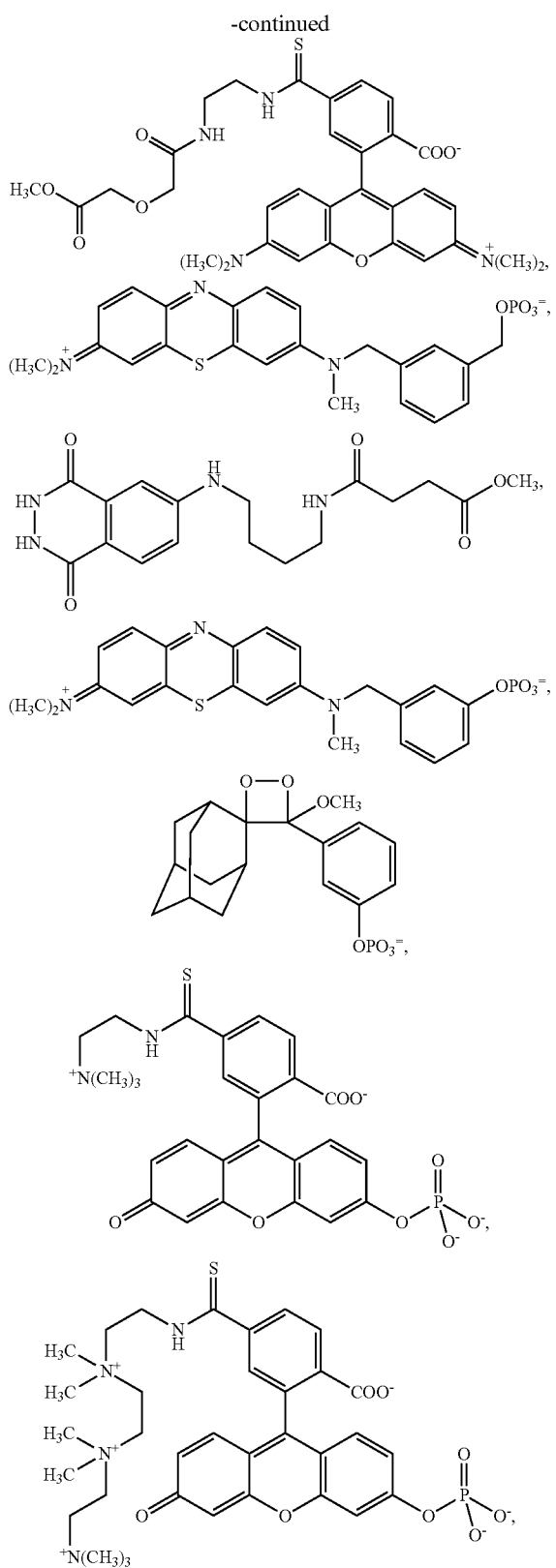
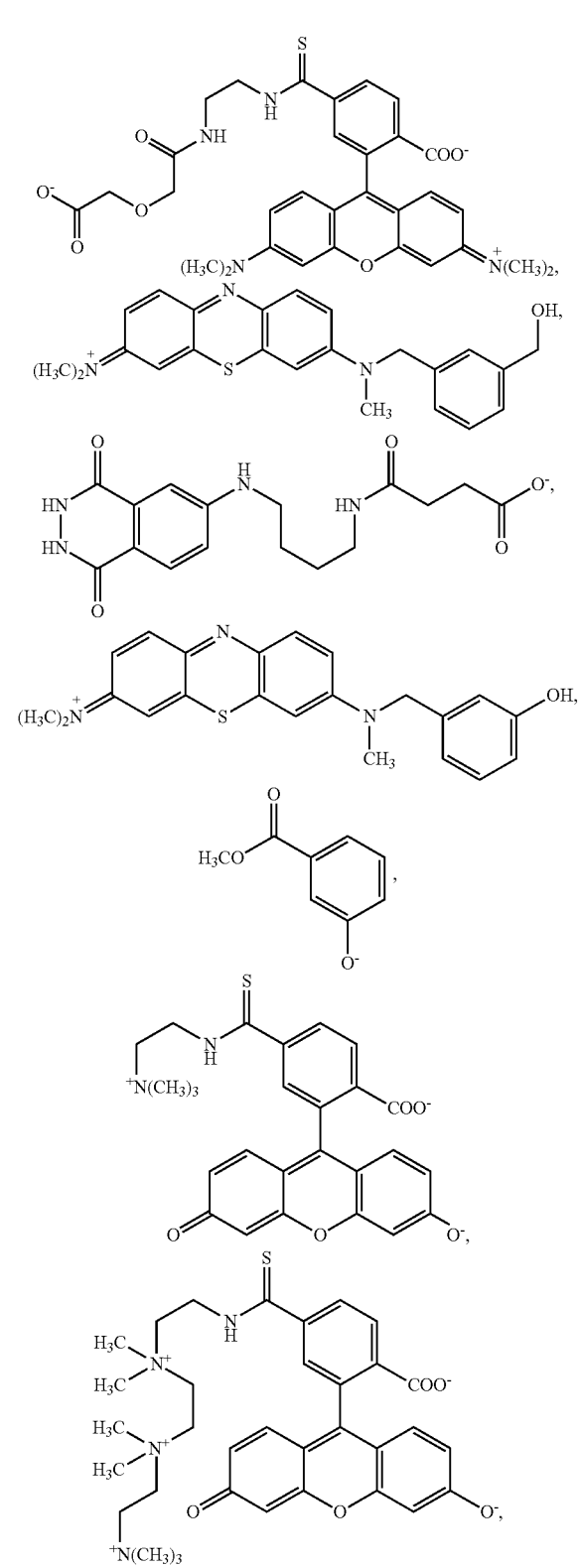

or any variant of these or any combination of these.

7. The method of claim 1, wherein the reaction product molecules are resorufin anion, o-nitrophenolate, fluorescine anion, substituted coumarin anion, or any variant of these or any combination of these.

8. The method of claim 1, wherein the reaction product molecules comprise a chromophore; or wherein the substrate molecules comprise a chromophore and the reaction product molecules comprise the same chromophore; or wherein the reaction product molecules comprise a moiety capable of undergoing a chemiluminescent reaction; or wherein the reaction product molecules comprise a moiety capable of being reversibly oxidized/reduced between two oxidation states; or any combination of these.

9. The method of claim 8, wherein the reaction product molecules comprise a chromophore selected from the group consisting of an azo dye, a xanthene dye, an anthraquinone dye, an acridine dye, an oxazine dye, a thiazene dye, a triarylmehtane dye, a diarylmethane dye, a quinoline styryl dye, a phthalocyanine dye, a squarene dye, a polyalkene dye and any combination of these.

10. The method of claim 1, wherein the microfluidic device further comprises a main microfluidic channel and a microfluidic side channel in fluid communication with the main microfluidic channel, wherein the binding surface is positioned in the main microfluidic channel and the microfluidic trapping region is positioned in the microfluidic side channel.

11. The method of claim 10, wherein the microfluidic device further comprises one or more additional microfluidic side channels positioned in fluid communication with the main microfluidic channel.

12. The method of claim 11, further comprising the step of providing one or more additional solutions to at least one of the one or more additional microfluidic side channels, at least one of the solutions comprising a reagent selected from the group consisting of: an acid, a base, an oxidizing agent, a reducing agent, a proton, a carboxylic acid, a phosphoric acid or mono- or di-ester of a phosphoric acid, bisulfate, a sulfonic acid, an ammonium or subsituted ammonium, phenol or substituted phenol, hydroxide, a carboxylate anion, phosphate, a mono-ester of a phosphate, a di-ester of a phosphate, an amine or substituted amine, a borate, a borate ester anionpersulfate, hypochlorite, hydroperoxide and any combination of these.

13. The method of claim 12, wherein the reagent reacts with the reaction product molecules, thereby establishing the ionic charge of the reaction product molecules.

14. The method of claim 12, wherein the reagent comprises an acid, a base, an oxidizing agent or a reducing agent or is selected from the group consisting of: a proton, a carboxylic acid, a phosphoric acid or mono- or di-ester of a phosphoric acid, bisulfate, a sulfonic acid, an ammonium or subsituted ammonium, phenol or substituted phenol, hydroxide, a carboxylate anion, phosphate or mono- or di-ester of a phosphate, an amine or substituted amine, a borate or borate ester anionpersulfate, hypochlorite, hydroperoxide and any combination of these.

15. The method of claim 1, wherein the concentrating step comprises allowing time to pass, whereby unreacted substrate molecules continue to catalytically react with the catalyst molecules bound directly or indirectly to target analyte molecules bound to the binding surface to directly or indirectly produce reaction product molecules which concentrate in the microfluidic trapping region.

16. The method of claim 1, wherein the semi-permeable membrane is positioned between the binding surface and the electrode in the microfluidic trapping region.

17. A method for detecting a target analyte, the method comprising the steps of:
providing a microfluidic device comprising a binding surface in fluid communication with a microfluidic trapping region and at least two electrodes, wherein the microfluidic trapping region comprises a semi-permeable membrane, wherein the microfluidic trapping region comprises a semi-permeable membrane and wherein the binding surface comprises binding molecules capable of selectively binding to the target analyte;
providing to the binding surface a first solution comprising target analyte molecules, wherein at least a number of the target analyte molecules selectively bind to the binding molecules of the binding surface, thereby creating an analyte activated binding surface;
providing to the analyte activated binding surface a second solution comprising catalyst molecules, wherein at least a number of the catalyst molecules further binds directly or indirectly to the analyte activated binding surface, thereby creating a catalytic binding surface;
providing to the catalytic binding surface a third solution comprising substrate molecules, the substrate molecules comprising a chromophore, wherein at least a number of the substrate molecules undergo a catalytic chemical reaction at the catalytic binding surface, thereby producing reaction product molecules, the reaction product molecules comprising the chromophore in the same or a substantially unaltered form as in the substrate molecules and wherein an ionic charge of the reaction product molecules is different from an ionic charge of the substrate molecules;
transporting at least a number of the reaction product molecules into the trapping region by applying an electrical potential between the at least two electrodes, wherein at least one electrode is positioned in the microfluidic trapping region and wherein the electrical potential provides a force attracting the reaction product molecules toward the microfluidic trapping region;
concentrating reaction product molecules in the microfluidic trapping region in front of, at a surface of and/or within the semi-permeable membrane; and
detecting an amount of concentrated reaction product molecules in the microfluidic trapping region in front of, at a surface of and/or within the semi-permeable membrane.

18. The method of claim 17, wherein the semi-permeable membrane impedes movement of the reaction product molecules toward the at least one electrode positioned in the microfluidic trapping region.

19. The method of claim 17, wherein the step of detecting an amount of concentrated reaction product molecules in front of, at a surface of and/or within the semi-permeable membrane comprises detecting an amount of concentrated reaction product molecules as a function of time or after one or more time intervals.

20. The method of claim 1 or 17, wherein detecting said amount of concentrated reaction product molecules comprises a step selected from the group consisting of:
exposing at least a portion of the concentrated reaction product molecules to electromagnetic radiation and detecting scattering, absorption or emission of electromagnetic radiation;
exposing at least a portion of the concentrated reaction product molecules to a reagent that induces chemiluminescence and detecting emitted electromagnetic radiation; and
measuring a voltage or a current required to change the oxidation state of at least a portion of the concentrated reaction product molecules.

21. The method of claim 1 or 17, wherein detecting said amount of concentrated reaction product molecules is carried out using a technique selected from the group consisting of ultraviolet-visible spectrometry, fluorescence spectrometry, Raman spectrometry (SERS), infrared spectrometry, detection of radioactive decay from radiolabeled reaction product molecules, amperometry and voltametry.

* * * * *